United States Patent
Kumar et al.

(10) Patent No.: US 7,320,826 B2
(45) Date of Patent: Jan. 22, 2008

(54) PHOTOCHROMIC ARTICLES WITH REDUCED TEMPERATURE DEPENDENCY AND METHODS FOR PREPARATION

(75) Inventors: Anil Kumar, Allegheny County, PA (US); Barry Van Gemert, Westmoreland County, PA (US); Forrest R. Blackburn, Allegheny County, PA (US); Clara E. Nelson, Allegheny County, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 129 days.

(21) Appl. No.: 10/393,174

(22) Filed: Mar. 20, 2003

(65) Prior Publication Data

US 2004/0191520 A1 Sep. 30, 2004

(51) Int. Cl.
B32B 17/10 (2006.01)
B32B 27/20 (2006.01)
B32B 27/36 (2006.01)
B32B 33/00 (2006.01)
G02C 7/10 (2006.01)

(52) U.S. Cl. .............. 428/411.1; 428/423.1; 428/426; 428/457; 428/480; 428/500; 428/522; 428/537.1; 428/537.5; 428/913; 359/738; 351/163

(58) Field of Classification Search .......... 428/411.1, 428/426, 457, 412, 413, 537.1, 537.5, 688, 428/522, 423.1, 500, 533, 480, 913; 351/163; 359/581, 738
See application file for complete search history.

(56) References Cited

U.S. PATENT DOCUMENTS

| | | | | |
|---|---|---|---|---|
| 3,212,898 | A | 10/1965 | Cerreta | 96/90 |
| 3,361,706 | A | 1/1968 | Meriwether et al. | 260/39 |
| 3,666,352 | A | 5/1972 | Wagner et al. | 350/160 |
| 4,166,043 | A | 8/1979 | Uhlmann et al. | 252/300 |
| 4,289,497 | A | 9/1981 | Hovey | 8/506 |
| 4,360,653 | A * | 11/1982 | Stevens et al. | 526/301 |
| 4,367,170 | A | 1/1983 | Uhlmann et al. | 252/586 |
| 4,720,356 | A | 1/1988 | Chu | 252/586 |
| 4,931,220 | A | 6/1990 | Haynes et al. | 252/586 |
| 5,000,878 | A | 3/1991 | Chu | 252/587 |
| 5,166,345 | A | 11/1992 | Akashi | 544/71 |
| 5,191,367 | A * | 3/1993 | Salibello et al. | 351/243 |
| 5,236,958 | A | 8/1993 | Miyashita | 518/121 |
| 5,252,742 | A | 10/1993 | Miyashita | 548/121 |
| 5,330,686 | A | 7/1994 | Smith et al. | 252/586 |
| 5,359,085 | A | 10/1994 | Iwamoto | 548/468 |
| 5,488,119 | A | 1/1996 | Fischer-Reimann et al. | 552/201 |
| 5,645,767 | A | 7/1997 | Van Gemert | 252/586 |
| 5,658,501 | A | 8/1997 | Kumar et al. | 252/586 |
| 5,698,141 | A | 12/1997 | Kumar | 252/586 |
| 5,723,072 | A | 3/1998 | Kumar | 252/586 |
| 5,728,189 | A | 3/1998 | Kerko et al. | 65/32.1 |
| 5,730,911 | A * | 3/1998 | Cano et al. | 264/1.1 |
| 5,753,146 | A | 5/1998 | Van Gemert et al. | 252/586 |
| 5,821,287 | A | 10/1998 | Hu et al. | 524/89 |
| 5,955,520 | A | 9/1999 | Heller et al. | 524/87 |
| 5,959,761 | A | 9/1999 | Perrott et al. | 359/244 |
| 5,961,892 | A | 10/1999 | Gemert et al. | 252/586 |
| 5,973,039 | A | 10/1999 | Florent et al. | 524/100 |
| 6,084,702 | A | 7/2000 | Byker et al. | 359/288 |
| 6,099,283 | A * | 8/2000 | Soane et al. | 425/123 |
| 6,113,814 | A | 9/2000 | Gemert et al. | 252/586 |
| 6,146,554 | A | 11/2000 | Melzig et al. | 252/586 |
| 6,150,430 | A | 11/2000 | Walters et al. | 522/79 |
| 6,153,126 | A | 11/2000 | Kumar | 252/586 |
| 6,296,785 | B1 | 10/2001 | Nelson et al. | 252/586 |
| 6,306,316 | B1 | 10/2001 | Mann et al. | 252/586 |
| 6,348,604 | B1 | 2/2002 | Nelson et al. | 549/389 |
| 6,353,102 | B1 | 3/2002 | Kumar | 544/60 |
| 6,555,028 | B2 | 4/2003 | Walters et al. | 252/586 |

FOREIGN PATENT DOCUMENTS

| | | | | |
|---|---|---|---|---|
| US | 2002/0169315 | 11/2002 | | 544/60 |
| US | 2003/0008958 | 1/2003 | | 524/368 |
| WO | 97/05213 | 2/1997 | | |
| WO | 01/70719 A2 | 9/2001 | | |

OTHER PUBLICATIONS

Kirk-Othmer Encyclopedia of Chemical Technology, Fourth Edition, vol. 6, pp. 322-325.
Kirk-Othmer Encyclopedia of Chemical Technology, Fourth Edition, vol. 6, pp. 669-760.
Photochromic Ocular Devices, U.S. Appl. No. 10/393,178, filed Mar. 20, 2003.

* cited by examiner

*Primary Examiner*—Ramsey Zacharia
(74) *Attorney, Agent, or Firm*—Deborah M. Altman; Frank P. Mallak; Linda Pingitore

(57) ABSTRACT

Described are photochromic articles that include a substrate, a temperature dependent reducing amount of at least one organic photochromic material (b) that changes from more absorbing to less absorbing of radiation in its activating spectral absorbance as the temperature increases from 10° C. to 35° C. and at least one other photochromic material (c) that is different from photochromic material (b). In the article, photochromic material (b) is interposed between photochromic material (c) and a source of activating radiation. The photochromic article demonstrates a more consistent photochromic response, for example, an optical density response loss of 50 percent or less over a temperature range of from 10° C. to 35° C. as measured in the Photochromic Temperature Dependence Test. Methods for producing the aforedescribed articles are also disclosed.

56 Claims, 1 Drawing Sheet

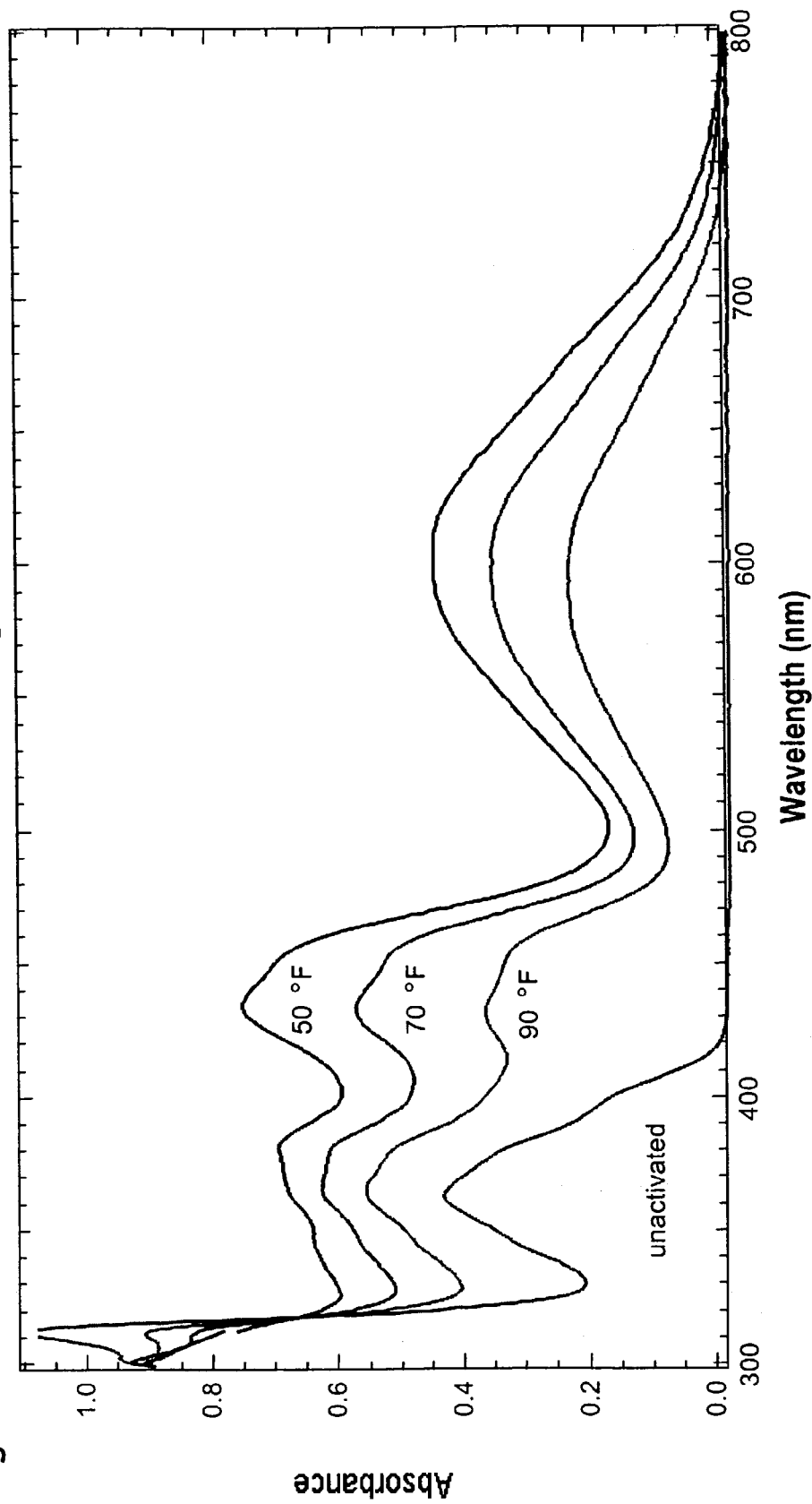

PHOTOCHROMIC ARTICLES WITH REDUCED TEMPERATURE DEPENDENCY AND METHODS FOR PREPARATION

BACKGROUND OF THE INVENTION

The present invention relates to novel photochromic articles demonstrating a more consistent photochromic response over a broad temperature range and methods for preparing such articles. More particularly, this invention relates to photochromic articles having reduced temperature dependency. Temperature dependency is a particular problem in photochromic articles, e.g., spectacle lenses. The coloration of the photochromic article is effected by the temperature at which it is used. Typically, a photochromic article demonstrating the temperature dependency effect will not get dark enough when it is hot and/or will get too dark when it is cold.

All photochromic materials exhibit a change in absorbance, very typically with an observable change in color when exposed to electromagnetic radiation containing ultraviolet rays, such as the ultraviolet radiation in sunlight or the light of a mercury lamp. When the ultraviolet radiation is discontinued, thermally fading photochromic materials will return to their original (typically colorless) state. In such photochromic materials represented by, but not limited to, oxazines and naphthopyrans, the coloration reaction is largely photochemical while the decoloration (or fading) reaction is primarily thermal in nature. Photochromic materials that are operative in such a manner, will display what is called the "temperature dependency effect" in articles using these compounds.

Temperature dependency is a result of a shift in the equilibrium concentrations of the ground state or closed form (typically colorless) and activated state or open form (typically colored). At higher temperatures, the equilibrium will be shifted towards the ground (typically colorless) state while at lower temperatures, the equilibrium will be shifted towards the activated (typically colored) state. Articles will therefore present a different response depending on the ambient temperature.

In one approach, the temperature dependency of photochromic compositions and articles was reduced by switching to all naphthopyran photochromic compounds from the earlier used oxazines or mixtures of oxazines and naphthopyrans. While this improvement was substantial and welcomed, there remains a need to improve these and other photochromic systems by further reducing the temperature dependency effect.

BRIEF DESCRIPTION OF THE FIGURE

FIG. 1 shows the absorbance of the activated species as compared to the unactivated species of Photochromic Compound A as a function of the temperature of the compound in solution for a wavelength range from 300 to 800 nanometers.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The phrase "an at least partial coating" means an amount of coating covering from a portion to the complete surface of the substrate. The phrase "an at least partially cured coating" refers to a coating in which the curable or crosslinkable components are at least partially cured, crosslinked and/or reacted. In alternate non-limiting embodiments of the present invention, the degree of reacted components can vary widely, e.g., from 5% to 100% of all the possible curable, crosslinkable and/or reactable components.

The phrase "an at least partially abrasion resistant coating or film" refers to a coating or film that demonstrates a resistance to abrasion that is greater than the standard reference material, typically a plastic made of CR-39® monomer available from PPG Industries, Inc, as tested in a method comparable to ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the uncoated surface. Put another way, the percent transmittance of the coated surface can range from a percentage greater than the uncoated surface up to 99.9.

In one non-limiting embodiment, the use of at least one photochromic material having a temperature dependent variable absorbance within it's activating spectral absorbance in a photochromic article can adapt the article to be less temperature dependent. The photochromic material having the temperature dependent variable absorbance is referred to as a TDVA material herein.

The TDVA material has an activated form and an unactivated form, the activated form of which changes from more absorbing to less absorbing of radiation in the absorption region of its unactivated form as the temperature increases. The magnitude of the change in absorption of the TDVA material can depend on the difference between the temperatures at which it is tested and the activity of the TDVA material. The temperature range over which the TDVA material can change from more absorbing to less absorbing of radiation can vary widely. In one non-limiting embodiment, the temperature range can be from 10° C. to 35° C.

In one non-limiting embodiment, at least one TDVA material can be used to adapt a photochromic article to exhibit an activated optical density response loss of 50 percent or less as measured in the Photochromic Temperature Dependence Test. In an alternate non-limiting embodiment, at least one TDVA material can be used to adapt a photochromic article to exhibit an unactivated state luminous transmittance of greater than 70 percent at 23° C. and a difference of 20 percent or less between the activated state luminous transmittance at saturation measured at 10° C. and the activated state luminous transmittance at saturation measured at 35° C., said photochromic article being activated by simulated sunlight from a xenon arc lamp set at 6.7 Watts/meter$^2$ UVA and 50,000 lumens/meter$^2$. In the aforementioned alternate non-limiting embodiment, the photochromic articles typically reach saturation within 30 minutes of exposure to the simulated sunlight at 10° C. and within 15 minutes of exposure to the simulated sunlight at 35° C. The term "activated luminous state transmittance at saturation" means that the transmittance of the photochromic article has reached a point where it will not substantially change due to continued exposure to simulated sunlight.

In various non-limiting embodiments, the TDVA material can be deposited on or near the surface of the article, between the source of radiation and the other photochromic materials, or the TDVA material can be dispersed throughout the article with or without other photochromic materials. In further non-limiting embodiments, the TDVA material can demonstrate a greater absorbance within its own activating spectral absorbance and/or within the activating spectral absorbance of other photochromic material when the article is at low temperatures, and conversely a lower absorbance at higher temperatures.

In another non-limiting embodiment, the temperature dependency effect can be lessened in a photochromic article containing a mixture of photochromic materials by including at least one TDVA material that creates a temperature dependent switchable screen of the activation spectral absorbance for itself and/or for the other photochromic materials different from the TDVA material. Such other photochromic materials can have an activating spectral absorbance within a 300 to 450 nanometer (nm) wavelength range.

In one non-limiting embodiment, the other photochromic material can also be TDVA materials that demonstrate this property to a lesser extent than the main TDVA material. Whatever photochromic materials, including other TDVA materials, that are used in conjunction with the TDVA materials in the photochromic article, the photochromic article of the present invention, in one non-limiting embodiment, is adapted to demonstrate an optical density response loss of 50 percent or less as measured in the Photochromic Temperature Dependence Test described in Example 43 herein. In an alternate non-limiting embodiment, the photochromic article is adapted to exhibit a difference of 20 percent or less between the activated state luminous transmittance at saturation measured at 10° C. and the activated state luminous transmittance at saturation measured at 35° C., the photochromic article being activated by simulated sunlight and exhibiting an unactivated state luminous transmittance of greater than 70 percent at 23° C.

In a further non-limiting embodiment, the TDVA material can be used alone or combined with the other photochromic materials in the substrate, in a coating or film on the surface of the substrate or both, or the TDVA material can be interposed between the other photochromic materials and the source of radiation. This can be accomplished, in one non-limiting embodiment, by adding the TDVA materials and other optional photochromic materials to the ingredients used to form the substrate, coating or film and/or by imbibing the TDVA materials and other optional photochromic materials into the substrate, coating or film.

In a still further non-limiting embodiment, the TDVA materials can have additional absorbances outside the activating spectral absorbance of themselves or the other photochromic materials of the article. In one non-limiting embodiment, the TDVA material can have an absorbance within the visible range from 400 to 800 nanometers or from 450 to 800 nm, as shown in FIG. 1.

The Photochromic Temperature Dependence Test is described in Example 43 herein. Basically, test samples containing TDVA material with or without other photochromic compounds are tested for photochromic response, e.g., the change in optical density, at 50° F. (10° C.) and 95° F. (35° C.). The optical density response loss is calculated by using the following formula:

$$\% \Delta OD \text{ Loss} = 100 \times (1 - \Delta OD@95° F./\Delta OD@50° F.)$$

In one non-limiting embodiment, photochromic articles of the present invention demonstrate an optical density response loss (% ΔOD loss) of 50 percent or less. In another contemplated non-limiting embodiment, the % ΔOD loss is 40 percent or less. In a further contemplated non-limiting embodiment, the % ΔOD loss is 20 percent or less, e.g., 0. The % ΔOD loss can range between any of the aforestated values, e.g., from 0 to 50 percent, and their inclusive values, e.g., from 1 to 49 percent.

In an alternate non-limiting embodiment, photochromic articles of the present invention demonstrate an unactivated state luminous transmittance of greater than 70 percent at 23° C. and a difference of 20 percent or less between the activated state luminous transmittance at saturation measured at 10° C. and the activated state luminous transmittance at saturation measured at 35° C. In another non-limiting embodiment, photochromic articles of the present invention demonstrate an unactivated state luminous transmittance of greater than 80 percent at 23° C. and a difference of 10 percent or less between the activated state luminous transmittance at saturation measured at 10° C. and the activated state luminous transmittance at saturation measured at 35° C. The difference between the activated state luminous transmittance at saturation measured at 10° C. and the activated state luminous transmittance at saturation measured at 35° C. can range between any of the aforestated values, e.g., from 0 to 20, and their inclusive values, e.g., from 1 to 9 or from 1 to 19. The unactivated state luminous transmittance at 23° C. can range between any of the aforestated values, e.g., from 70.1 to 100 percent or from 80.1 to 100 percent, and their inclusive values, e.g., from 71 to 99 percent or from 81 to 99 percent.

In a series of alternate non-limiting embodiments, TDVA materials of the present invention include photochromic materials adapted to change from an unactivated form to an activated form upon exposure to actinic radiation and the activated form changing from more absorbing to less absorbing of radiation in the absorption region of the unactivated form as the temperature increases. In one non-limiting embodiment, the TDVA materials are chosen from the following naphthopyrans and mixtures thereof. In the definitions of the substituents shown in formulae I to VIII, like symbols have the same meaning unless stated otherwise.

In one non-limiting embodiment, the naphthopyran can be represented by the following graphic formula I:

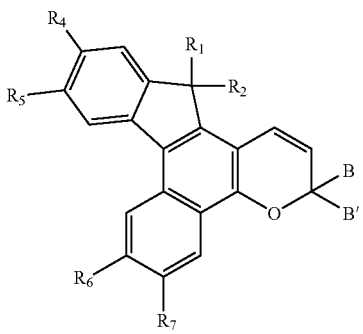

wherein, (a) $R_1$ and $R_2$ are each independently chosen from:
  (i) hydrogen, hydroxy, $C_1$-$C_6$ alkyl, amino, mono- or di-substituted amino, $C_1$-$C_8$ haloalkyl, $C_3$-$C_7$ cycloalkyl, allyl, benzyl, mono-substituted benzyl, halogen, the group, —C(O)W, wherein W is hydroxy, $C_1$-$C_6$ alkyl, $C_1$-$C_6$ alkoxy, phenyl, mono-substituted phenyl, amino, mono($C_1$-$C_6$)alkylamino, di($C_1$-$C_6$)alkylamino, morpholino, piperidino or pyrrolidyl, said amino substituents being chosen from $C_1$-$C_6$ alkyl, phenyl, benzyl or naphthyl, said benzyl and phenyl substituents being $C_1$-$C_6$ alkyl or $C_1$-$C_6$ alkoxy;
  (ii) the unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in (a) (ii) being chosen from halogen, $C_1$-$C_6$ alkyl or $C_1$-$C_6$ alkoxy;
  (iii) mono-substituted phenyl, said substituent located at the para position being a linking group, —(CH$_2$)$_t$— or —O—(CH$_2$)$_t$—, wherein t is the integer 1, 2, 3, 4, 5 or 6, said linking group being connected to an aryl group which is on another photochromic material, e.g. an organic photochromic material such as chromene which includes benzopyrans and naphthopyrans;
  (iv) the group, —OR$_8$ wherein R$_8$ is $C_1$-$C_6$ alkyl, $C_1$-$C_6$ acyl, $C_1$-$C_8$ haloalkyl, triarylsilyl, e.g., triphenylsilyl, triarylsilyloxy, e.g., triphenylsilyloxy, tri($C_1$-$C_6$)alkylsilyl, e.g., trimethylsilyl, tri($C_1$-$C_6$)alkylsilyloxy, e.g., trimethylsilyloxy, tri($C_1$-$C_6$)alkoxysilyl, e.g., trimethoxysilyl, tri($C_1$-$C_6$)alkoxysilyloxy, e.g., trimethoxysilyloxy, di($C_1$-$C_6$)alkyl($C_1$-$C_6$ alkoxy)silyl, e.g., dimethylmethoxysilyl, di($C_1$-$C_6$)alkyl($C_1$-$C_6$ alkoxy)silyloxy, e.g., dimethylmethoxysilyloxy, di($C_1$-$C_6$)alkoxy($C_1$-$C_6$ alkyl) silyl, e.g., dimethoxymethylsilyl, di($C_1$-$C_6$)alkoxy($C_1$-$C_6$ alkyl)silyloxy, e.g., dimethylmethoxysilyloxy, phenyl($C_1$-$C_3$)alkyl, mono($C_1$-$C_6$) alkyl substituted phenyl($C_1$-$C_3$)alkyl, mono($C_1$-$C_6$) alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ haloalkyl, allyl, benzoyl, monosubstituted benzoyl, naphthoyl or monosubstituted naphthoyl, said benzoyl and naphthoyl group substituents being $C_1$-$C_6$ alkyl or $C_1$-$C_6$ alkoxy; or R$_8$ is the group —CH(R$_9$)Q, wherein R$_9$ is hydrogen or $C_1$-$C_3$ alkyl and Q is —CN, —CF$_3$, or —COOR$_{10}$, and R$_{10}$ is hydrogen or $C_1$-$C_3$ alkyl; or R$_8$ is the group, —C(O)V, wherein V is hydrogen, $C_1$-$C_6$ alkoxy, phenoxy, mono- or di-($C_1$-$C_6$)alkyl substituted phenoxy, mono- or di-($C_1$-$C_6$)alkoxy substituted phenoxy, the unsubstituted, mono- or di-substituted aryl groups, phenyl and naphthyl, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, said aryl group substituents being $C_1$-$C_6$ alkyl or $C_1$-$C_6$ alkoxy;
  (v) the group —CH(Q')$_2$ wherein Q' is —CN or —COOR$_{11}$, wherein R$_{11}$ is hydrogen, $C_1$-$C_1$alkyl, $C_3$-$C_7$ cycloalkyl, phenyl($C_1$-$C_3$)alkyl, mono($C_1$-$C_6$) alkyl substituted phenyl($C_1$-$C_3$)alkyl, mono($C_1$-$C_6$) alkoxy substituted phenyl($C_1$-$C_3$)alkyl, or the unsubstituted, mono- or di-substituted aryl groups phenyl or naphthyl, each of said phenyl and naphthyl group substituents being $C_1$-$C_6$ alkyl or $C_1$-$C_6$ alkoxy;
  (vi) the group —CH(R$_{12}$)G, wherein R$_{12}$ is hydrogen, $C_1$-$C_6$ alkyl or the unsubstituted, mono- or di-substituted aryl groups, phenyl or naphthyl, and G is —COOR$_{11}$, —COR$_{13}$ or —CH$_2$OR$_{14}$, wherein R$_{13}$ is hydrogen, $C_1$-$C_6$ alkyl, the unsubstituted, mono- or di-substituted aryl groups phenyl or naphthyl, amino, mono($C_1$-$C_6$)alkylamino, di($C_1$-$C_6$)alkylamino, phenylamino, mono- or di-($C_1$-$C_6$)alkyl substituted phenylamino, mono- or di-($C_1$-$C_6$)alkoxy substituted phenylamino, diphenylamino, mono- or di($C_1$-$C_6$)alkyl substituted diphenylamino, mono- or di($C_1$-$C_6$)alkoxy substituted diphenylamino, morpholino, or piperidino, wherein R$_{14}$ is hydrogen, —C(O)R$_{11}$, $C_1$-$C_6$ alkyl, $C_1$-$C_3$ alkoxy($C_1$-$C_6$)alkyl, phenyl($C_1$-$C_3$)alkyl, mono ($C_1$-$C_6$)alkoxy substituted phenyl($C_1$-$C_3$)alkyl, or the unsubstituted, mono- or di-substituted aryl groups phenyl or naphthyl, each of said phenyl and naphthyl group substituents being $C_1$-$C_6$ alkyl or $C_1$-$C_6$ alkoxy; or
  (vii) the group T represented by the formula:

-Z[(OC$_2$H$_4$)$_x$(OC$_3$H$_6$)$_y$(OC$_4$H$_8$)$_z$]Z' or

—[(OC$_2$H$_4$)$_x$(OC$_3$H$_6$)$_y$(OC$_4$H$_8$)$_z$]Z' wherein -Z is —C(O)— or —CH$_2$—, Z' is $C_1$-$C_3$ alkoxy or a polymerizable group defined herein as any functional group capable of participating in a polymerization reaction, x, y and z are each a number between 0 and 50, and the sum of x, y and z is between 2 and 50.

In one non-limiting embodiment, polymerization of the photochromic polymerizable compounds can occur by mechanisms described in the definition of "polymerization" in *Hawley's Condensed Chemical Dictionary*, Thirteenth Edition, 1997, John Wiley & Sons, pages 901-902. Those mechanisms include by "addition", in which free radicals are the initiating agents that react with the double bond of the monomer by adding to it on one side at the same time producing a new free electron on the other side, by "condensation", involving the splitting out of water molecules by two reacting monomers and by so-called "oxidative coupling". Non-limiting examples of the polymerizable groups are hydroxy, (meth)acryloxy, 2-(methacryloxy)ethylcarbamyl, or epoxy, e.g., oxiranylmethyl. When there are 2 or more polymerizable groups on the naphthopyran, they may be the same or different.

The group, —(OC$_2$H$_4$)$_x$—, in the group T formulae, can represent poly(ethylene oxide); —(OC$_3$H$_6$)$_y$—, can represent poly(propylene oxide); and, (OC$_4$H$_8$)$_z$—, can represent poly(butylene oxide). When used in combination, the poly(ethylene oxide), poly(propylene oxide) and poly(butylene oxide) groups of T can be in a random or block order within the T moiety. The letters x, y and z are each a number between 0 and 50 and the sum of x, y and z is between 2 and 50. The sum of x, y and z can be any number that falls within the range of 2 to 50, e.g., 2, 3, 4 . . . 50. This sum can also range from any lower number to any higher number within the range of 2 to 50, e.g., 6 to 50, 31 to 50. The numbers for x, y, and z are average values and can be partial numbers, e.g., 9.5.

Alternatively, $R_1$ and $R_2$ together form $R_3$ chosen from an oxo group, a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$-$C_6$ alkyl.

(b) $R_4$ and $R_7$ are each independently chosen from hydrogen, provided that both are not hydrogen, the group T, —$OR_7$, wherein $R_7$, is chosen from $C_1$-$C_6$ alkyl, phenyl($C_1$-$C_3$)alkyl or $C_1$-$C_6$ alkoxy($C_1$-$C_6$)alkyl, or $R_4$ and $R_7$ are each independently chosen from a nitrogen-containing group chosen from:

(i) —$N(R_{15})R_{16}$ wherein $R_{15}$ and $R_{16}$ are each independently chosen from hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl or $R_{15}$ and $R_{16}$ come together with the nitrogen atom to form a $C_3$-$C_{20}$ hetero-bicycloalkyl ring or a $C_4$-$C_{20}$ hetero-tricycloalkyl ring;

(ii) a nitrogen containing ring represented by the following graphic formula:

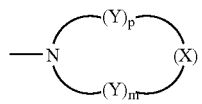

wherein each Y is independently chosen for each occurrence from —$CH_2$—, —$CH(R_{17})$—, —$C(R_{17})(R_{17})$—, —CH(aryl)-, —$C(aryl)_2$-, or —$C(R_{17})$(aryl)-, and X is chosen from —Y—, —O—, —S—, —S(O)—, —$S(O_2)$—, —NH—, —$N(R_{17})$— or —N(aryl)-, wherein $R_{17}$ is $C_1$-$C_6$ alkyl, said aryl is phenyl or naphthyl, m is the integer 1, 2 or 3, and p is the integer 0, 1, 2, or 3 and when p is 0, X is Y; or (iii) a group represented by the following graphic formulae:

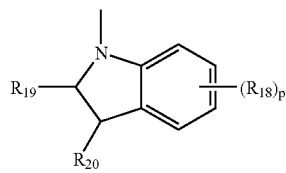

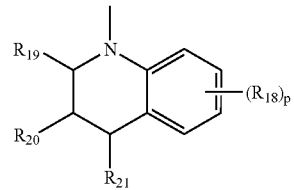

wherein $R_{19}$, $R_{20}$ and $R_{21}$ are each independently chosen for each occurrence in each formula from hydrogen, $C_1$-$C_6$ alkyl, phenyl or naphthyl, or the groups $R_{19}$ and $R_{20}$ together form a ring of 5 to 8 carbon atoms and each $R_{18}$ is independently chosen for each occurrence in each formula from $C_1$-$C_6$ alkyl, $C_1$-$C_6$ alkoxy, fluoro or chloro and p is the integer 0, 1, 2 or 3;

(c) $R_5$ and $R_6$ are each independently chosen from hydrogen, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$)alkoxyaryl($C_1$-$C_6$)alkyl, $C_1$-$C_6$ haloalkyl, mono($C_1$-$C_6$)alkoxy($C_1$-$C_4$)alkyl, the group T, described hereinbefore in (a) (vii) —$OR_7$, described hereinbefore in (b), or nitrogen-containing group (b) (i), (ii) or (iii); and (d) B and B' are each independently chosen from:

(i) mono-T-substituted phenyl; said group T being the same as described hereinbefore in (a) (vii);

(ii) the unsubstituted, mono-, di-, or tri-substituted aryl group, phenyl or naphthyl, each of said aryl substituents being chosen from hydroxy, aryl, mono($C_1$-$C_6$)alkoxyaryl, di($C_1$-$C_6$)alkoxyaryl, mono($C_1$-$C_6$)alkylaryl, $C_1$-$C_8$ alkoxy ($C_1$-$C_8$) alkoxy, di($C_1$-$C_6$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_6$) alkyl, $C_3$-$C_7$ cycloalkyloxy($C_1$-$C_6$)alkoxy, aryl($C_1$-$C_6$) alkyl, aryl($C_1$-$C_6$)alkoxy, aryloxy, aryloxy($C_1$-$C_6$) alkyl, aryloxy($C_1$-$C_6$)alkoxy, mono- or di-($C_1$-$C_6$) alkylaryl($C_1$-$C_6$)alkyl, mono- or di-($C_1$-$C_6$)alkoxyaryl ($C_1$-$C_6$)alkyl, mono- or di-($C_1$-$C_6$)alkylaryl($C_1$-$C_6$) alkoxy, mono- or di-($C_1$-$C_6$)alkoxyaryl($C_1$-$C_6$)alkoxy, $C_1$-$C_6$ alkyl, $C_1$-$C_6$ haloalkyl, $C_1$-$C_6$ alkoxy, $C_1$-$C_6$ acyl, $C_1$-$C_6$ acyloxy, mono($C_1$-$C_6$)alkoxy($C_1$-$C_4$)alkyl, acryloxy, methacryloxy, halogen, —$CF_3$, —CN, —$SR_{11}$, —$S(O)R_{11}$, —$S(O_2)R_{11}$ or —$COOR_{11}$;

(iii) mono-substituted phenyl, said substituent at the para position being a linking group, —$(CH_2)_t$— or —O—$(CH_2)_t$—, wherein t is the integer 1, 2, 3, 4, 5 or 6, said linking group being connected to an aryl group on another photochromic material; or (iv) $C_1$-$C_6$ alkyl, $C_1$-$C_6$ haloalkyl, $C_1$-$C_6$ alkoxy($C_1$-$C_4$) alkyl, $C_3$-$C_6$ cycloalkyl, mono($C_1$-$C_6$)alkoxy($C_3$-$C_6$) cycloalkyl, mono($C_1$-$C_6$)alkyl($C_3$-$C_6$)-cycloalkyl, halo($C_3$-$C_6$)cycloalkyl or $C_4$-$C_{12}$ bicycloalkyl; or (f) B and B' taken together form fluoren-9-ylidene, mono-, or di-substituted fluoren-9-ylidene, saturated $C_3$-$C_{12}$ spiro-monocyclic hydrocarbon ring, saturated $C_7$-$C_{12}$ spiro-bicyclic hydrocarbon ring, or saturated $C_7$-$C_{12}$ spiro-tricyclic hydrocarbon ring, each of said fluoren-9-ylidene substituents being chosen from $C_1$-$C_4$ alkyl, $C_1$-$C_4$ alkoxy, or halogen, said halo or halogen groups herein are chloro, fluoro, iodo or bromo.

In another non-limiting embodiment, the substituents of the naphthopyran represented by graphic I include:

(a) $R_1$ and $R_2$ are each independently chosen from:
(i) hydrogen, hydroxy, $C_1$-$C_6$ alkyl, $C_1$-$C_6$ haloalkyl, $C_3$-$C_7$ cycloalkyl, benzyl or mono-substituted benzyl, said benzyl substituent being $C_1$-$C_6$ alkyl or $C_1$-$C_6$ alkoxy;
(ii) phenyl or mono-substituted phenyl, said phenyl substituent in (a) (ii) being halogen, $C_1$-$C_6$ alkyl or $C_1$-$C_6$ alkoxy;
(iii) mono-substituted phenyl, said substituent at the para position being a linking group, —O—$(CH_2)_t$—, wherein t is the integer 1, 2, 3, or 4, said linking group being connected to an aryl group on another photochromic material;
(iv) the group, —$OR_8$ wherein $R_8$ is $C_1$-$C_6$ alkyl, $C_1$-$C_6$ acyl, phenyl($C_1$-$C_3$)alkyl, or $C_1$-$C_6$ alkoxy($C_2$-$C_4$) alkyl, or $R_8$ is the group —CH($R_9$)Q, wherein $R_9$ is hydrogen or $C_1$-$C_3$ alkyl and Q is —$COOR_{10}$, and $R_{10}$ is $C_1$-$C_3$ alkyl;
(v) the group —CH(Q')$_2$ wherein Q' is —$COOR_{11}$, wherein $R_{11}$ is $C_1$-$C_6$ alkyl;
(vi) the group —CH($R_{12}$)G, wherein $R_{12}$ is hydrogen or $C_1$-$C_6$ alkyl, and G is —$COOR_{11}$, or —$CH_2OR_{14}$, wherein $R_{11}$ is $C_1$-$C_6$ alkyl, $R_{14}$ is $C_1$-$C_6$ alkyl or $C_1$-$C_3$ alkoxy($C_1$-$C_6$)alkyl; or
(vii) the group T represented by the formula:

-Z[(OC$_2$H$_4$)$_x$(OC$_3$H$_6$)$_y$(OC$_4$H$_8$)$_z$]Z' or

—[(OC$_2$H$_4$)$_x$(OC$_3$H$_6$)$_y$(OC$_4$H$_8$)$_z$]Z' wherein -Z is —$CH_2$—, Z' is $C_1$-$C_3$ alkoxy or a polymerizable group, such as epoxy, (meth)acryloxy, e.g., acryloxy or methacryloxy, or 2-(methacryloxy)ethylcarbamyl, x, y and z are each a number between 0 and 50, and the sum of x, y and z is between 2 and 50; or
(viii) $R_1$ and $R_2$ together form $R_3$ chosen from an oxo group, a substituted or unsubstituted spiro-carbocyclic ring containing 3 to 6 carbon atoms, said spiro-carbocyclic ring being annellated with 0, 1 or 2 benzene rings, said substituents being hydrogen or $C_2$-$C_6$ alkyl;
(b) $R_4$ and $R_7$ are each independently chosen from hydrogen (provided that both are not hydrogen), the group —$OR_{7'}$ wherein $R_{7'}$ is chosen from $C_1$-$C_3$ alkyl, phenyl($C_1$-$C_2$)alkyl or $C_1$-$C_3$ alkoxy($C_1$-$C_3$)alkyl or a nitrogen-containing group chosen from:
(i) —N($R_{15}$)$R_{16}$ wherein $R_{15}$ and $R_{16}$ are each independently chosen from $C_1$-$C_8$ alkyl, phenyl, $C_1$-$C_8$ alkylaryl, or $C_3$-$C_{20}$ cycloalkyl, wherein said aryl group is phenyl or naphthyl;
(ii) a nitrogen containing ring represented by the following graphic formula:

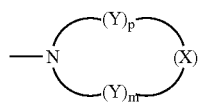

wherein each Y is independently chosen for each occurrence from —$CH_2$—, or —CH($R_{17}$)—, and X is chosen from —Y—, —O—, —S—, —NH—, —N($R_{17}$)— or —N(aryl)-, wherein $R_{17}$ is $C_1$-$C_6$ alkyl, said aryl being phenyl or naphthyl, m is the integer 1, 2 or 3, and p is the integer 0, 1, 2, or 3 and when p is O, X is Y; or (iii) a group represented by the following graphic formulae:

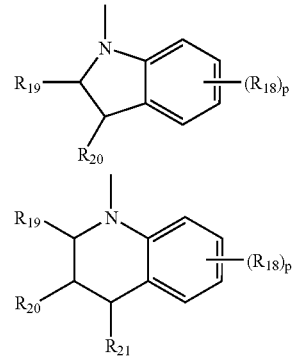

wherein $R_{19}$, $R_{20}$ and $R_{21}$ are each independently chosen for each occurrence in each formula from hydrogen or $C_1$-$C_6$ alkyl each $R_{18}$ is independently chosen for each occurrence in each formula from $C_1$-$C_3$ alkyl, $C_1$-$C_3$ alkoxy or fluoro and p is the same as described hereinbefore in (b) (ii);
(c) $R_5$ and $R_6$ are each independently chosen from hydrogen, $C_1$-$C_6$ alkyl, $C_3$-$C_7$ cycloalkyl, aryloxy($C_1$-$C_6$)alkyl, the group T, described hereinbefore in (a) (vii), —$OR_{7'}$, described hereinbefore in (b), or nitrogen-containing group (b) (i), (ii) or (iii); and
(d) B and B' are each chosen from:
(i) mono-T-substituted phenyl; said T-group being the same as described hereinbefore in (a) (vii);
(ii) the unsubstituted, mono-, or di-substituted aryl groups, phenyl or naphthyl, each of said aryl substituents being chosen from aryl, $C_1$-$C_6$ alkyl, $C_1$-$C_6$ haloalkyl, $C_1$-$C_6$ alkoxy, acryloxy, methacryloxy, halogen, —$CF_3$, —CN or —$COOR_{11}$;
(iii) monosubstituted phenyl, said substituent located at the para position being a linking group, —$(CH_2)_t$— or —O—$(CH_2)_t$—, wherein t is the integer 1, 2, 3, 4, 5 or 6, said linking group being connected to an aryl group on another photochromic material;
(iv) $C_1$-$C_6$ alkyl, $C_1$-$C_6$ haloalkyl, $C_3$-$C_6$ cycloalkyl, mono($C_1$-$C_6$)alkoxy($C_3$-$C_6$)cycloalkyl or $C_4$-$C_{12}$ bicycloalkyl; or
(f) B and B' taken together form fluoren-9-ylidene, monosubstituted fluoren-9-ylidene, saturated $C_3$-$C_{12}$ spiro-monocyclic hydrocarbon ring, saturated $C_7$-$C_{12}$ spiro-bicyclic hydrocarbon ring, or saturated $C_7$-$C_{12}$ spiro-tricyclic hydrocarbon ring, each of said fluoren-9-ylidene substituents being chosen from $C_1$-$C_4$ alkyl, $C_1$-$C_4$ alkoxy, or halogen, said halo or halogen groups being chloro, fluoro, iodo and bromo.

Non-limiting examples of photochromic materials represented by graphic formula I include:
(a) 3-(4-methoxyphenyl)-3-phenyl-6,7,10,11-tetramethoxy-13-ethyl-13-hydroxy-13H-3H-indeno[2,'3,'3,4]naphtho[1,2-b]pyran;
(b) 3,3-di(4-methoxyphenyl)-6,11-dimethoxy-13-butyl-13-ethoxy-13H-3H-indeno[2,'3,'3,4]naphtho[1,2-b]pyran;
(c) 3-(4-methoxyphenyl)-3-phenyl-6,11-dimethoxy-13-methyl-13-(2-(2-hydroxyethoxy)ethoxy)-13H-3H-indeno[2,'3,'3,4]naphtho[1,2-b]pyran;
(d) 3,3-di(4-methoxyphenyl)-11-morpholino-13,13-dimethyl-13H-3H-indeno[2,'3,'3,4]naphtho[1,2-b]pyran;

(e) 3-(4-morpholinophenyl)-3-phenyl-11-morpholino-13,13-dimethyl-13H-3H-indeno[2,'3,'3,4]naphtho[1,2-b]pyran;

(f) 3-(4-methoxyphenyl)-3-phenyl-10,11-dimethoxy-13,13-dimethyl-13H-3H-indeno[2,'3,'3,4]naphtho[1,2-b]pyran;

(g) 3-(4-methoxyphenyl)-3-phenyl-13,13-dimethyl-13H-3H-indeno[2,'3,'3,4]naphto[1,2-b]pyran;

(h) 3,3-di(4-methoxyethoxyphenyl)-11-morpholino-13,13-dimethyl-13H-3H-indeno[2,'3,'3,4]naphtho[1,2-b]pyran;

(i) 3,3-diphenyl-6,11-dimethoxy-13-acetoxy-13H-3H-indeno[2,'3,'3,4]naphtho[1,2-b]pyran;

(j) 3-(4-methoxyphenyl)-3-phenyl-6,10,11-trimethoxy-13-methyl-13-hydroxy-13H-3H-indeno[2,'3,'3,4]naphtho[1,2-b]pyran;

(k) 3-(4-morpholinophenyl)-3-(4-methoxyphenyl)-11-morpholino-13,13-dimethyl-13H-3H-indeno[2,'3,'3,4]naphtho[1,2-b]pyran;

(l) 3-(3,4-dimetethoxyphenyl)-3-(4-methoxyphenyl)-11-morpholino-13,13-dimethyl-13H-3H-indeno[2,'3,'3,4]naphtho[1,2-b]pyran;

(m) 3-(4-methoxyphenyl)-3-phenyl-6,7,10,11-tetramethoxy-13-13-dimethyl-13H-3H-indeno[2,'3,'3,4]naphtho[1,2-b]pyran;

(n) 3-(4-methoxyphenyl)-3-phenyl-6,7,10,11-tetramethoxy-13-trifluromethyl-13-hydroxy-13H-3H-indeno[2,'3,'3,4]naphtho[1,2-b]pyran;

(o) 3-(4-methoxyphenyl)-3-phenyl-6,10,11-trimethoxy-13-butyl-13-hydroxy-13H-3H-indeno[2,'3,'3,4]naphtho[1,2-b]pyran;

(p) 3-(4-morpholinophenyl)-3-phenyl-6,11-dimethoxy-13-methoxy-13-methyl-13H-3H-indeno[2,'3,'3,4]naphtho[1,2-b]pyran;

(q) 3,3-di (4-dimethoxyphenyl)-6,7,10,11-tetramethoxy-13,13-dimethyl-13H-3H-indeno[2,'3,'3,4 ]naphtho[1,2-b]pyran;

(r) 3,3-diphenyl-13,13-dimethyl-13H-3H-indeno[2,'3,'3,4]naphtho[1,2-b]pyran;

(s) 3-(4-methoxyphenyl)-3-phenyl-6,11-dimethoxy-13-ethyl-13-hydroxy-13H-3H-indeno[2,'3,'3,4]naphtho[1,2-b]pyran; or (t) mixtures thereof.

The materials represented by graphic formula I can be produced by methods known to those skilled in the art, for example, as disclosed in U.S. Pat. Nos. 5,645,767, 5,698,141, 5,723,072, 5,955,520, 5,961,892, 6,113,814, 6,146,554, 6,296,785B1 and EP1184379.

In one non-limiting embodiment, the naphthopyran can be represented by the following graphic formula II:

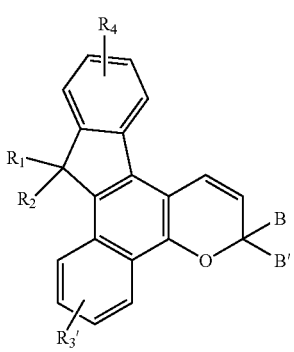

II wherein;

$R_1$, $R_2$, $R_4$, B and B' are the same groups described hereinbefore for graphic formula I; $R_{3'}$ is —$OR_{8'}$, wherein $R_{8'}$ is $C_1$-$C_6$ alkyl, phenyl($C_1$-$C_3$)alkyl, or $C_1$-$C_6$ alkoxy($C_2$-$C_4$)alkyl; or $R_{3'}$ is chosen from hydrogen, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$) alkyl, aryloxy($C_1$-$C_6$)alkyl, mono- or di-($C_1$-$C_6$)alkylaryl ($C_1$-$C_6$)alkyl, mono- or di-($C_1$-$C_6$)alkoxyaryl($C_1$-$C_6$)alkyl, $C_1$-$C_6$ haloalkyl, or mono($C_1$-$C_6$)alkoxy($C_1$-$C_4$)alkyl.

In another non-limiting embodiment, the substituents of the naphthopyran represented by graphic formula II include: $R_1$, $R_2$, $R_4$, B and B' which are the same groups described hereinbefore for another non-limiting embodiment of the naphthopyran represented by graphic formula I; $R_{3'}$ is —$OR_{8'}$, wherein $R_{8'}$ is $C_1$-$C_3$ alkyl, phenyl($C_1$-$C_2$)alkyl, or $C_1$-$C_3$ alkoxy($C_2$-$C_4$)alkyl; or $R_{3'}$ is hydrogen, $C_1$-$C_6$ alkyl, $C_3$-$C_7$ cycloalkyl, or $C_1$-$C_6$ haloalkyl.

Non-limiting examples of photochromic materials represented by graphic formula II include:

(a) 3,3-diphenyl-9-methyl-11-methoxy-3H-9H-indeno[3',2':3,4]naphtho [1,2-b]pyran;

(b) 3,3-diphenyl-9,9-dimethyl-11,6-dimethoxy-3H-9H-indeno[3',2':3,4]naphtho[1,2-b]pyran;

(c) 3-(4-methoxyphenyl)-3-phenyl-9,9-dimethyl-11,6-dimethoxy-3H-9H-indeno[3',2':3,4]naphtho [1,2-b]pyran;

(d) 3-(3-trifluoromethylphenyl)-3-phenyl-9-methyl-9-phenyl-11-dimethoxy-3H-9H-indeno[3',2':3,4]naphtho[1,2-b]pyran;

(e) 3,3diphenyl-9-phenyl-3H-9H-indeno[3',2':3,4]naphtho [1,2-b]pyran; or (f) mixtures thereof.

The materials represented by graphic formula II can be produced by methods known to those skilled in the art, for example, as disclosed in U.S. Pat. No. 6,018,059, U.S. patent application Ser. No. 10/039,984 filed Oct. 29, 2001 and Japan Unexamined Patent Publication P2000-327675A.

In one non-limiting embodiment, the naphthopyran can be represented by the following graphic formula III:

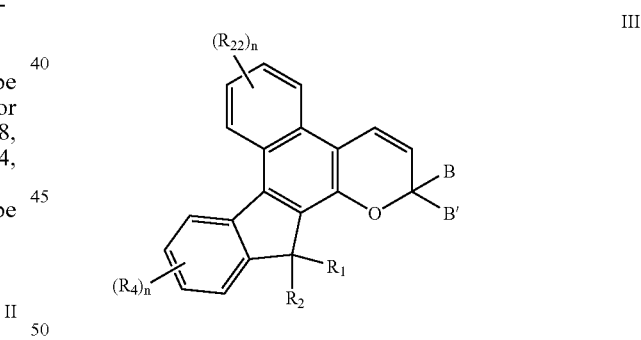

III wherein;

$R_1$, $R_2$, $R_4$, B and B' are the same groups described hereinbefore in one non-limiting embodiment of the naphthopyran represented by graphic formula I; each $R_{22}$ is independently chosen for each occurrence from hydrogen, $C_1$-$C_6$ alkyl, $C_3$-$C_7$ cycloalkyl, $C_3$-$C_7$ cycloalkyloxy($C_1$-$C_6$) alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$) alkoxyaryl($C_1$-$C_6$)alkyl, $C_1$-$C_6$ haloalkyl, mono($C_1$-$C_6$) alkoxy($C_1$-$C_4$)alkyl or —$OR_{8'}$, which was defined hereinbefore in one non-limiting embodiment of the naphthopyran represented by graphic formula II, and n is the integer 0, 1, 2, or 3.

In another non-limiting embodiment, the substituents of the naphthopyran represented by graphic formula III include: $R_1$, $R_2$, $R_4$, B and B' which are the same groups described hereinbefore in another non-limiting embodiment of the naphthopyran represented by graphic formula I; each $R_{22}$ is independently chosen for each occurrence from hydrogen, $C_1$-$C_6$ alkyl, $C_3$-$C_7$ cycloalkyl, or —$OR_8$, which was described hereinbefore in another non-limiting embodiment of the naphthopyran represented by graphic formula II, and n is the integer 0, 1, 2, or 3.

Non-limiting examples of photochromic materials represented by graphic formula III include:
(a) 2,2-diphenyl-6,7-dimethoxy-2H-13H-indeno[1',2':4,3]naphtho[2,1-b]pyran;
(b) 2,2-diphenyl-6,7-dimethoxy-13-methyl-2H-13H-indeno[1',2':4,3]naphtho[2,1-b]pyran;
(c) 2,2-diphenyl-6-methoxy-13,13-dimethyl-2H-13H-indeno [1',2':4,3]naphtho[2,1-b]pyran;
(d) 2-(3-trifluromethylphenyl)-2-phenyl-6-methoxy-13,13-dimethyl-2H-13H-indeno[1',2':4,3]naphtho[2,1-b]pyran;
(e) 2-(3-methoxyphenyl)-2-phenyl-6,7,11-trimethoxy-13-methyl-13-hydroxy-2H-13H-indeno[1',2':4,3]naphtho[2,1-b]pyran;
(f) 2-(3-methoxyphenyl)-2-phenyl-6,7-dimethoxy-13,13-dimethyl-2H-13H-indeno[1',2':4,3]naphtho[2,1-b]pyran;
(g) 2-(3-methoxyphenyl)-2-phenyl-6,7-dimethoxy-13-methyl-13-hydroxy-2H-13H-indeno[1',2':4,3]naphtho[2,1-b]pyran; or
(h) mixtures thereof.

The materials represented by graphic formula III can be produced by methods known to those skilled in the art, for example, as disclosed in U.S. Pat. Nos. 5,869,658 and 6,315,928.

In one non-limiting embodiment, the naphthopyran can be represented by the following graphic formula IV:

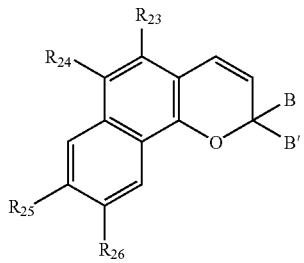

wherein;
(a) $R_{23}$ is —C(O)L, or —C($R_{27}$)($R_{28}$)$OR_{11}$, wherein L is —$OR_{11}$, —N($R_{15}$)$R_{16}$ or an unsubstituted, mono-substituted or di-substituted heterocyclic ring chosen from 1-indolinyl, morpholino, piperidino, 1-pyrrolidyl, 1-imidazolidyl, 2-imidazolin-1-yl, pyrazolidyl, pyrazolinyl or 1-piperazinyl, said heterocyclic ring substituents being $C_1$-$C_6$ alkyl or $C_1$-$C_6$ alkoxy, wherein $R_{11}$, $R_{15}$, and $R_{16}$ are the same as defined hereinbefore in one non-limiting embodiment of the naphthopyran represented by graphic formula I; $R_{27}$ and $R_{28}$ are each independently chosen from hydrogen, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$)alkoxyaryl($C_1$-$C_6$)alkyl, $C_1$-$C_6$ haloalkyl, mono($C_1$-$C_6$)alkoxy($C_1$-$C_4$)alkyl, phenyl or naphthyl said aryl group being phenyl or naphthyl;
(b) $R_{24}$ is hydrogen, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$)alkoxyaryl($C_1$-$C_6$)alkyl, mono-or di-($C_1$-$C_6$) alkylaryl, mono-or di-($C_1$-$C_6$) alkoxyaryl, $C_1$-$C_6$ haloalkyl, mono($C_1$-$C_6$)alkoxy($C_1$-$C_4$)alkyl or the aryl groups, phenyl or naphthyl;
(c) $R_{25}$ and $R_{26}$ are each independently chosen from hydrogen, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$)alkyl, aryloxy($C_1$-$C_6$)alkyl, mono- or di-($C_1$-$C_6$)alkylaryl($C_1$-$C_6$)alkyl, mono- or di-($C_1$-$C_6$)alkoxyaryl($C_1$-$C_6$)alkyl, $C_1$-$C_6$ haloalkyl, mono($C_1$-$C_6$)alkoxy($C_1$-$C_4$)alkyl, the group T, described hereinbefore for graphic formula I, —$OR_8$, described hereinbefore for graphic formula II, or a nitrogen-containing group described hereinbefore for graphic formula I as (b) (i), (ii) or (iii); or $R_{25}$ and $R_{26}$ together form one of the following graphic formula:

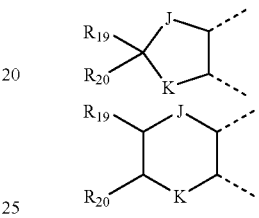

wherein J and K are each independently chosen for each occurrence in each formula from oxygen or the group —N($R_{15}$)—, $R_{15}$, $R_{19}$ and $R_{20}$ being the same groups described hereinbefore for graphic formula I (b) (i) and (iii); and
(d) B and B' are the same groups defined hereinbefore for graphic formula I.

In another non-limiting embodiment, the substituents of the naphthopyran represented by graphic formula IV include:
(a) $R_{23}$ is —C(O)L, or —C($R_{27}$) ($R_{28}$)$OR_{11}$, wherein L is —$OR_{11}$ or —N($R_{15}$)$R_{16}$; $R_{11}$, $R_{15}$, and $R_{16}$ are the same as defined hereinbefore for graphic formula I; $R_{27}$ and $R_{28}$ are each independently chosen from $C_1$-$C_6$ alkyl, $C_3$-$C_7$ cycloalkyl, aryl($C_1$-$C_6$)alkyl, mono- or di-($C_1$-$C_6$)alkylaryl ($C_1$-$C_6$)alkyl or phenyl;
(b) $R_{24}$ is hydrogen, $C_1$-$C_6$ alkyl, $C_3$-$C_7$ cycloalkyl, aryloxy($C_1$-$C_6$)alkyl, $C_1$-$C_6$ haloalkyl or phenyl;
(c) $R_{25}$ and $R_{26}$ are each independently chosen from hydrogen, $C_1$-$C_6$ alkyl, $C_1$-$C_6$ haloalkyl, mono($C_1$-$C_6$) alkoxy($C_1$-$C_4$)alkyl, the group —$OR_8$, described hereinbefore for graphic formula II, or a nitrogen-containing group defined hereinbefore for graphic formula I as (b) (i), (ii) or (iii); and
(d) B and B' are the same groups defined hereinbefore for graphic formula I.

Non-limiting examples of photochromic materials represented by graphic formula IV include:
(a) 2,2-diphenyl-5-(2-hydroxy)propyl)-8-methoxy-2H-naphtho[1,2-b]pyran;
(b) 2,2-phenyl-5-(2-(hydroxy)propyl)-6-phenyl-8,9-dimethoxy-2H-naphtho[1,2-b]pyran;
(c) 2,2-phenyl-5-carbomethoxy-6-phenyl-8,9-dimethoxy-2H-naphtho[1,2-b]pyran;
(d) 2-(3-trifluoromethylphenyl)-2-phenyl-5-carbomethoxy-6-methyl-9-methoxy-2H-naphtho[1,2-b]pyran;
(e) 2-phenyl-2-t-butyl-5-(2-(hydroxy)propyl)-8,9-dimethoxy-2H-naphtho[1,2-b]pyran;
(f) 2-phenyl-2-t-butyl-5-carbomethoxy-8,9-dimethoxy-2H-naphtho[1,2-b]pyran;

(g) 2,2-diphenyl-5-carbocyclohexyloxy -8-methoxy-2H-naphtho[1,2-b]pyran;
(h) 2,2-di(3-trifluoromethylphenyl)-5-carbomethoxy-6-methyl-9-methoxy-2H-naphtho[1,2-b]pyran;
(i) 2,2-diphenyl-5-carbomethoxy-6-(4-methoxyphenyl)-9-methoxy-2H-naphtho[1,2-b]pyran;
(j) 2,2-di(4-fluorophenyl)-5-carbomethoxy-6-methyl-9-methoxy-2H-naphtho[1,2-b]pyran;
(k) 2,2-di(3-trifluoromethylphenyl)-5-(2-(hydroxy)propyl)-6-methyl-9-methoxy-2H-naphtho[1,2-b]pyran;
(l) 2,2-diphenyl-5-carbomethoxy-6-phenyl-9-methoxy-2H-naphtho[1,2-b]pyran;
(m) 2,2-diphenyl-5-(2-(2-hydroxyethoxy)ethoxy) carbonyl-6-(4-methoxyphenyl)-9-methoxy-2H-naphtho[1,2-b]pyran; or
(n) mixtures thereof.

The materials represented by graphic formula IV can be produced by methods known to those skilled in the art, for example, as disclosed in U.S. Pat. Nos. 5,458,814; 5,573,712; 5,656,206; 6,248,264; 6,113,814; 5,961,892; and 6,348,604B1.

In one non-limiting embodiment, the naphthopyran can be represented by the following graphic formula V:

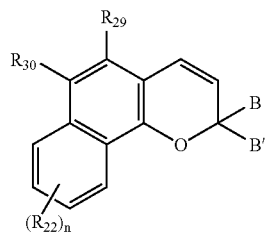

wherein;

(a) $R_{22}$ and n are the same as defined hereinbefore for graphic formula III; $R_{29}$ is hydroxy, $C_1$-$C_6$ alkyl, $C_3$-$C_7$ cycloalkyl, $C_3$-$C_7$ cycloalkyloxy($C_1$-$C_6$)alkyl, aryl($C_1$-$C_6$) alkyl, aryloxy($C_1$-$C_6$)alkyl, mono- or di-($C_1$-$C_6$)alkylaryl ($C_1$-$C_6$)alkyl, mono- or di-($C_1$-$C_6$)alkoxyaryl($C_1$-$C_6$)alkyl, $C_1$-$C_6$ haloalkyl, mono($C_1$-$C_6$)alkoxy($C_1$-$C_4$)alkyl, aryl, mono($C_1$-$C_6$)alkoxyaryl, di($C_1$-$C_6$)alkoxyaryl, mono($C_1$-$C_6$)alkylaryl, di($C_1$-$C_6$)alkylaryl, haloaryl, $C_3$-$C_7$ cycloalkylaryl, aminoaryl, mono($C_1$-$C_6$)alkylaminoaryl, di($C_1$-$C_6$) alkylaminoaryl, phenylaminoaryl, mono- or di-($C_1$-$C_6$)alkyl substituted phenylaminoaryl, mono- or di-($C_1$-$C_6$)alkoxy substituted phenylaminoaryl, diphenylaminoaryl, mono- or di($C_1$-$C_6$)alkyl substituted diphenylaminoaryl, mono- or di($C_1$-$C_6$)alkoxy substituted diphenylaminoaryl, the group T, described hereinbefore for graphic formula I(a) (vii), —$OR_{8'}$, described hereinbefore for graphic formula II, or a nitrogen-containing group described hereinbefore for graphic formula I as (b) (i), (ii) or (iii);

(b) $R_{30}$ is hydrogen or $R_{23}$ described hereinbefore for graphic formula IV (a); and (c) B and B' are the same groups defined hereinbefore for graphic formula I.

In another non-limiting embodiment, the substituents on the naphthopyran represented by graphic formula V include:

(a) $R_{22}$ and n are the same as defined hereinbefore for graphic formula III, $R_{29}$ is hydroxy, $C_1$-$C_6$ alkyl, $C_3$-$C_7$ cycloalkyl, aryloxy($C_1$-$C_6$)alkyl, $C_1$-$C_6$ haloalkyl, aryl, mono($C_1$-$C_6$)alkoxyaryl, di($C_1$-$C_6$)alkoxyaryl, haloaryl, aminoaryl, mono($C_1$-$C_6$)alkylaminoaryl, di($C_1$-$C_6$)alkylaminoaryl, phenylaminoaryl, mono- or di-($C_1$-$C_6$)alkoxy substituted phenylaminoaryl, diphenylaminoaryl, the group T, —$OR_{8'}$ or a nitrogen-containing group described hereinbefore for graphic formula I as (b) (i), (ii) or (iii);

(b) $R_{30}$ is hydrogen or $R_{23}$ described hereinbefore for graphic formula IV (a); and (c) B and B' are the same groups defined hereinbefore for graphic formula I.

Non-limiting examples of photochromic materials represented by graphic formula V include:
(a) 2,2-phenyl-5-methyl-2H-naphtho[1,2-b]pyran;
(b) 2,2-phenyl-5-phenyl-2H-naphtho[1,2-b]pyran;
(c) 2,2-phenyl-6-carbomethoxy-5-(4-morpholinophenyl)-2H-naphtho[1,2-b]pyran;
(d) 2,2-phenyl-6-carbomethoxy-5-hydroxy-2H-naphtho[1,2-b] pyran;
(e) 2,2-phenyl-6-carbomethoxy-5-methoxy-2H-naphtho[1,2-b] pyran;
(f) 2,2-phenyl-6-carbomethoxy-5-8-dimethoxy-2H-naphtho[1,2-b] pyran;
(g) 2-phenyl-2-(3-trifluorophenyl)-6-phenyl-5-hydroxy-2H-naphtho[1,2-b]pyran;
(h) 2-phenyl-2-(4-methoxyphenyl)-6-(2-(hydroxy)propyl)-5-morpholino-2H-naphtho[1,2-b]pyran;
(i) 2-phenyl-2-(4-methoxyphenyl)-6-(2-(hydroxy)propyl)-5-(4-morpholinophenyl)-2H-naphtho[1,2-b]pyran;
(j) 2-phenyl-2-t-butyl-6-(2-(hydroxy)propyl)-5-(4-morpholinophenyl)-2H-naphtho[1,2-b]pyran; or
(k) mixtures thereof.

The materials represented by graphic formula V can be produced by methods known to those skilled in the art, for example, as disclosed in U.S. Pat. No. 6,353,102B1.

In one non-limiting embodiment, the naphthopyran can be represented by the following graphic formula VI:

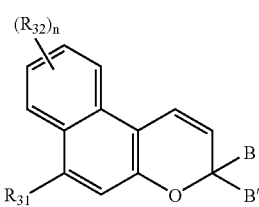

wherein;

(a) $R_{31}$ is hydrogen or $R_{29}$ described hereinbefore for graphic formula V(a);

(b) $R_{32}$ is $C_1$-$C_6$ alkyl, $C_1$-$C_6$ alkoxy, $C_3$-$C_7$ cycloalkyl, or $C_1$-$C_6$ haloalkyl, and (c) B and B' and n are the same groups described hereinbefore for graphic formulae I and III.

In another non-limiting embodiment, the substituents of the naphthopyran represented by graphic formula VI include: $R_{32}$ is hydrogen, n is O; $R_{31}$ is hydrogen or $R_{29}$, wherein $R_{29}$ is hydroxy, $C_1$-$C_6$ alkyl, $C_3$-$C_7$ cycloalkyl, aryloxy($C_1$-$C_6$)alkyl, $C_1$-$C_6$ haloalkyl, aryl, mono($C_1$-$C_6$) alkoxyaryl, di($C_1$-$C_6$)alkoxyaryl, haloaryl, aminoaryl, mono ($C_1$-$C_6$)alkylaminoaryl, di($C_1$-$C_6$)alkylaminoaryl, phenylaminoaryl, mono- or di-($C_1$-$C_6$)alkoxy substituted phenylaminoaryl, diphenylaminoaryl, the group T, —$OR_{8'}$ or a nitrogen-containing group defined hereinbefore for graphic formula I as (b) (i), (ii) or (iii); and B and B' are the same groups defined hereinbefore for graphic formula I.

Non-limiting examples of photochromic materials represented by graphic formula VI include:
(a) 3-phenyl-3-(2-fluorophenyl)-3H-naphtho[2,1-b]pyran;
(b) 3-phenyl-3-(2-fluorophenyl)-6-acetoxy-3H-naphtho[2,1-b] pyran;
(c) 3,3-diphenyl-6-morpholino-3H-naphtho[2,1-b]pyran;
(d) 3-phenyl-3-(2-fluorophenyl)-5-hydroxymethyl-3H-naphtho[2,1-b]pyran;
(e) 3-phenyl-3-(3-trifluoromethylphenyl)-3H-naphtho[2,1-b] pyran;
(f) 3-(4-methylphenyl)-3-(2-fluorophenyl)-3H-naphtho[2,1-b] pyran or
(g) mixtures thereof.

The materials represented by graphic formula VI can be produced by methods known to those skilled in the art, for example, as disclosed in U.S. Pat. Nos. 5,520,853; 5,623,005; 5,744,070; 5,961,892; 6,022,496; 6,036,890; 6,113,814; 6,190,580; and 6,294,112.

In one non-limiting embodiment, the naphthopyran can be represented by the following graphic formula VII:

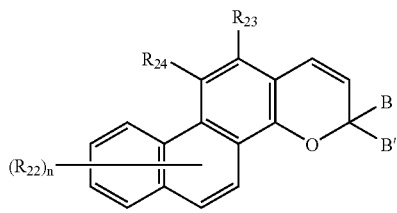

VII wherein:
each $R_{22}$, $R_{23}$, $R_{24}$, B, B' and n are the same as defined hereinbefore for graphic formulae III and IV. In another non-limiting embodiment, the substituents of the naphthopyran represented by graphic formula VII include: each $R_{22}$, $R_{23}$, $R_{24}$, B, B' and n being the same as defined hereinbefore for another non-limiting embodiment of graphic formulae I, III and IV.

A non-limiting embodiment of a photochromic material represented by graphic formulae VII is:
(a) 3,3-diphenyl-12-methoxycarbonyl-11-methyl-6-methoxy-3H-phenanthro[1,2-b]pyran.

The materials represented by graphic formulae VII can be produced by methods known to those skilled in the art, for example, as disclosed in U.S. Pat. Nos. 5,514,817 and 6,342,459B1.

In one non-limiting embodiment, the naphthopyran can be represented by the following graphic formula VIII:

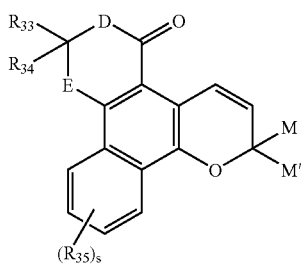

VIII wherein,
(a) $R_{33}$ and $R_{34}$ together form an oxo group or $R_{33}$ is hydrogen and $R_{34}$ is hydrogen, $C_1$-$C_6$ alkyl, $C_3$-$C_7$ cycloalkyl, allyl, phenyl, mono- or di-substituted phenyl, benzyl, mono-substituted benzyl, naphthyl, mono- or di-substituted naphthyl, $C_4$-$C_{12}$ bicycloalkyl, linear or branched $C_3$-$C_{12}$ alkenyl, $C_1$-$C_6$ alkoxy carbonyl($C_1$-$C_6$) alkyl, methacryloxy($C_1$-$C_6$)alkyl, acryloxy($C_1$-$C_6$)alkyl, $C_1$-$C_4$ acyloxy($C_1$-$C_6$)alkyl, $C_1$-$C_6$ alkoxy($C_1$-$C_6$)alkyl or an unsubstituted, mono- or di-substituted heteroaromatic group chosen from pyridyl, furanyl, benzofuran-2-yl, benzyfuran-3-yl, thienyl, benzothien-2-yl, benzothien-3-yl, dibenzofuranyl, dibenzothienyl, carbazolyl, benzopyridyl or indolyl, each of said phenyl, benzyl, naphthyl or heteroaromatic group substituents being $C_1$-$C_6$ alkyl, $C_1$-$C_6$ alkoxy, morpholino, di($C_1$-$C_6$)alkylamino, chloro or fluoro;

(b) each $R_{35}$ is independently chosen for each occurrence from $C_1$-$C_6$ alkyl, $C_1$-$C_6$ alkoxy, chloro, fluoro, phenyl, mono- or di-substituted phenyl, benzyl or mono-substituted benzyl, $C_3$-$C_7$ cycloalkyl, aryloxy, di($C_1$-$C_6$)alkylamino, morpholino, thiomorpholino, piperidino, pyridyl, tetrahydroquinolino, isoquinolino, aziridino, diarylamino, N—($C_1$-$C_6$)alkyl piperizino or N-aryl piperizino, wherein said aryl group is phenyl or naphthyl, each of said phenyl or benzyl substituents being $C_1$-$C_6$ alkyl, $C_1$-$C_6$ alkoxy, fluoro or chloro, and s is the integer 0, 1 or 2;

(c) D is oxygen or —N($R_{36}$)—, wherein $R_{36}$ is hydrogen, $C_1$-$C_6$ alkyl, $C_3$-$C_7$ cycloalkyl, allyl, vinyl, $C_1$-$C_5$ acyl, phenyl, mono- or di-substituted phenyl, benzyl, mono-substituted benzyl, $C_1$-$C_4$ alkoxycarbonyl($C_1$-$C_6$)alkyl, methacryloxy($C_1$-$C_6$)alkyl, acryloyloxy($C_1$-$C_6$)alkyl, phenyl($C_1$-$C_6$)alkyl, naphthyl, $C_4$-$C_{12}$ bicycloalkyl, $C_2$-$C_4$ acyloxy or an unsubstituted mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl or indolyl, each of said phenyl, benzyl or heteroaromatic group substituents being $C_1$-$C_6$ alkyl or $C_1$-$C_6$ alkoxy;

(d) E is oxygen, —N($R_{36}$)— or —C($R_{37}$) ($R_{38}$)—, wherein $R_{37}$ and $R_{38}$ are each independently chosen from hydrogen, $C_1$-$C_6$ alkyl or $C_3$-$C_7$ cycloalkyl, with the proviso that when E is —C($R_{37}$) ($R_{38}$)—, D is oxygen; and (e) M and M' are each chosen from:
(i) the unsubstituted, mono-, di- or tri-substituted aryl group, phenyl or naphthyl;
(ii) the unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl, indoloyl or fluorenyl, each of said aryl and heteroaromatic substituents in parts (i) and (ii) being chosen from hydroxy, aryl, e.g., phenyl or naphthyl, mono($C_1$-$C_6$)alkoxyaryl, di($C_1$-$C_6$)alkoxyaryl, mono($C_1$-$C_6$)alkylaryl, di($C_1$-$C_6$)alkylaryl, chloroaryl, fluoroaryl, $C_3$-$C_7$ cycloalkylaryl, $C_3$-$C_7$ cycloalkyl, $C_3$-$C_7$ cycloalkyloxy, $C_3$-$C_7$ cycloalkyloxy ($C_1$-$C_6$)alkyl, $C_3$-$C_7$ cycloalkyloxy($C_1$-$C_6$)alkoxy, aryl($C_1$-$C_6$)alkyl, aryl($C_1$-$C_6$)alkoxy, aryloxy, aryloxy($C_1$-$C_6$)alkyl, aryloxy($C_1$-$C_6$)alkoxy, mono- or di-($C_1$-$C_6$)alkylaryl($C_1$-$C_6$)alkyl, mono- or di-($C_1$-$C_6$)alkoxyaryl ($C_1$-$C_6$)alkyl, mono- or di-($C_1$-$C_6$)alkylaryl($C_1$-$C_6$) alkoxy, mono- or di-($C_1$-$C_6$)alkoxyaryl($C_1$-$C_6$)alkoxy, amino, mono($C_1$-$C_6$)alkylamino, di($C_1$-$C_6$)alkylamino, diarylamino, piperazino, N—($C_1$-$C_6$)alkylpiperazino, N-arylpiperazino, aziridino, indolino, piperidino, morpholino, thiomorpholino, tetrahydroquinolino, tetrahydroisoquinolino, pyrryl, $C_1$-$C_6$ alkyl, $C_1$-$C_6$ chloroalkyl, $C_1$-$C_6$ fluoroalkyl, $C_1$-$C_6$ alkoxy, mono($C_1$-$C_6$) alkoxy($C_1$-$C_4$)alkyl, acryloxy, methacryloxy, bromo, chloro or fluoro;

(iii) the group represented by one of the following graphic formulae:

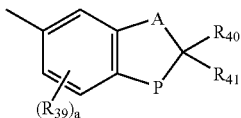

VIII A

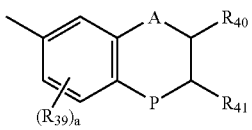

VIII B wherein A is independently chosen for each formula from carbon or oxygen and P is independently chosen for each formula from oxygen or substituted nitrogen, provided that when P is substituted nitrogen, A is carbon, said nitrogen substituents being chosen from hydrogen, $C_1$-$C_6$ alkyl or $C_2$-$C_6$ acyl; each $R_{39}$ is independently chosen for each occurrence in each formula from $C_1$-$C_6$ alkyl, $C_1$-$C_6$ alkoxy, hydroxy, chloro or fluoro; $R_{40}$ and $R_{41}$ are each independently chosen for each formula from hydrogen or $C_1$-$C_6$ alkyl; and a is the integer 0, 1 or 2;

(iv) $C_1$-$C_6$ alkyl, $C_1$-$C_6$ chloroalkyl, $C_1$-$C_6$ fluoroalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)cycloalkyl, mono($C_1$-$C_6$)alkyl($C_3$-$C_6$)cycloalkyl, chloro($C_3$-$C_6$)cycloalkyl, fluoro($C_3$-$C_6$)cycloalkyl or $C_4$-$C_{12}$ bicycloalkyl; or (v) the group represented by the following graphic formula:

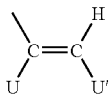

VIII C wherein U is hydrogen or $C_1$-$C_4$ alkyl and U' is chosen from naphthyl, mono-, or di-substituted naphthyl, phenyl, mono- or di-substituted phenyl, furanyl, mono- or di-substituted furanyl, thienyl, or mono- or di-substituted thienyl, each of the group substituents in this part (v) being $C_1$-$C_4$ alkyl, $C_1$-$C_4$ alkoxy, fluoro or chloro; or (vi) M and M' taken together form fluoren-9-ylidene, mono-, or di-substituted fluoren-9-ylidene, saturated $C_3$-$C_{12}$ spiro-monocyclic hydrocarbon ring, saturated $C_7$-$C_{12}$ spirobicyclic hydrocarbon ring or saturated $C_7$-$C_{12}$ spiro-tricyclic hydrocarbon ring, each of said fluoren-9-ylidene substituents being of $C_1$-$C_4$ alkyl, $C_1$-$C_4$ alkoxy, fluoro or chloro.

In another non-limiting embodiment, the substituents of the naphthopyran represented by graphic formula VIII include:

(a) $R_{33}$ is hydrogen and $R_{34}$ is chosen from hydrogen, $C_1$-$C_5$ alkyl, $C_3$-$C_6$ cycloalkyl, phenyl, mono- or di-substituted phenyl, benzyl or mono-substituted benzyl, each of said phenyl and benzyl group substituents being $C_1$-$C_4$ alkyl or $C_1$-$C_4$ alkoxy;

(b) $R_{35}$ is $C_1$-$C_4$ alkyl, $C_1$-$C_4$ alkoxy, fluoro, phenyl or aryloxy, and s is the integer 0, 1, or 2;

(c) D is oxygen or —N($R_{36}$)—, wherein $R_{36}$ is hydrogen, $C_1$-$C_3$ alkyl, methacryloxy($C_1$-$C_6$)alkyl or acryloxy($C_1$-$C_6$)alkyl;

(d) E is oxygen, —NH— or —$CH_2$—; and (e) M and M' are each independently chosen from:
  (i) phenyl, mono-substituted phenyl or di-substituted phenyl;
  (ii) an unsubstituted, mono- or di-substituted heteroaromatic group chosen from furanyl, benzofuran-2-yl, thienyl, benzothien-2-yl, or dibenzofuranyl, each of said phenyl and heteroaromatic substituents being diarylamino, di($C_1$-$C_3$)alkylamino, piperidino, aryloxy, morpholino, pyrryl, $C_1$-$C_3$ alkyl, $C_1$-$C_3$ chloroalkyl, $C_1$-$C_3$ fluoroalkyl, $C_1$-$C_3$ alkoxy, mono($C_1$-$C_3$)alkoxy ($C_1$-$C_3$)alkyl, fluoro or chloro;
  (iii) the groups represented by the graphic formulae VIII A and VIII B, wherein A is carbon and P is oxygen, each $R_{39}$ is independently chosen for each formula from $C_1$-$C_3$ alkyl or $C_1$-$C_3$ alkoxy, $R_{40}$ and $R_{41}$ are each independently chosen for each formula from hydrogen or $C_1$-$C_4$ alkyl, and a is the integer 0 or 1;
  (iv) $C_1$-$C_4$ alkyl; or
  (v) the group represented by the graphic formula VIII C wherein U is hydrogen or methyl and U' is phenyl or mono-substituted phenyl, said phenyl substituent being $C_1$-$C_3$ alkyl, $C_1$-$C_3$ alkoxy or fluoro; or
  (vi) M and M' taken together form fluoren-9-ylidene, mono-substituted fluoren-9-ylidene, saturated $C_3$-$C_8$ spiro-monocyclic hydrocarbon ring, saturated $C_7$-$C_{10}$ spiro-bicyclic hydrocarbon ring, or saturated $C_7$-$C_{10}$ spiro-tricyclic hydrocarbon ring, said fluoren-9-ylidene substituent being $C_1$-$C_3$ alkyl, $C_1$-$C_3$ alkoxy, fluoro or chloro.

Non-limiting examples of materials represented by graphic formula VIII include:

(a) 2,2,7,7-tetraphenyl-4-oxo-2,3,4,7-tetrahydro-1H-pyrimidino[5',4':3,4]naphtho[1,2-b]pyran;

(b) 7,7-diphenyl-2-pentyl-4-oxo-4H-7H-[1,3]dioxino[5',4': 3,4]naphtho[1,2-b]pyran;

(c) (2-fluorophenyl)-3-(3-methyl-4-methoxyphenyl)-2-pentyl-4-oxo-4H-7H-[1,3]dioxino[5',4':3,4]naphtho[1,2-b] pyran;

(d) 7-(4-morpholino-2-fluorophenyl)-7-(3,4-dimethoxyphenyl)-2-pentyl-4-oxo-4H-7H-[1,3]dioxino[5',4':3,4] naphtho [1,2-b]pyran; or (e) mixtures thereof.

The materials represented by graphic formula VIII can be produced by methods known to those skilled in the art, for example, as disclosed in U.S. Pat. Nos. 6,022,497 and 6,153,126.

The TDVA materials represented by graphic formulae I-VIII or a mixture thereof can be used in various non-limiting applications in which organic and inorganic photochromic materials can be employed, such as optical lenses, e.g., vision correcting ophthalmic lenses and piano lenses, face shields, goggles, visors, camera lenses, windows, automotive windshields, aircraft and automotive transparencies, e.g., T-roofs, sidelights and backlights, polymeric coatings, plastic films and sheets, textiles and pigmented liquids or pastes, e.g., paints and inks used as verification marks on security documents, e.g., documents such as banknotes, passports and drivers' licenses for which authentication or verification of authenticity may be desired.

In one non-limiting embodiment, it is contemplated that the TDVA materials of the present invention can each be used alone or in combination with other TDVA materials of the present invention, or in combination with one or more other organic or inorganic photochromic materials, e.g., photochromic compounds having at least one activated absorption maxima within the range of between about 400 and 700 nanometers, or materials containing the same, and can be incorporated, e.g., dissolved or dispersed, in a polymeric organic host material used to prepare photochromic articles, which color when activated to an appropriate hue.

In one non-limiting embodiment, the photochromic materials can include the following classes of materials: chromenes, e.g., naphthopyrans, benzopyrans, indenonaphthopyrans and phenanthropyrans; spiropyrans, e.g., spiro (benzindoline)naphthopyrans, spiro(indoline)benzopyrans, spiro(indoline)naphthopyrans, spiro(indoline)quinopyrans and spiro(indoline)pyrans; oxazines, e.g., spiro(indoline) naphthoxazines, spiro(indoline)pyridobenzoxazines, spiro (benzindoline)pyridobenzoxazines, spiro(benzindoline) naphthoxazines and spiro(indoline)benzoxazines; mercury dithizonates, fulgides, fulgimides and mixtures of such photochromic compounds.

Such photochromic compounds and complementary photochromic compounds are described in U.S. Pat. No. 4,931,220 at column 8, line 52 to column 22, line 40; U.S. Pat. No. 5,645,767 at column 1, line 10 to column 12, line 57; U.S. Pat. No. 5,658,501 at column 1, line 64 to column 13, line 17; U.S. Pat. No. 6,153,126 at column 2, line 60; U.S. Pat. No. 6,296,785 at column 2, line 47 to column 31, line 5; U.S. Pat. No. 6,348,604 at column 3, line 26 to column 17, line 15; and U.S. Pat. No. 6,353,102 at column 1, line 62 to column 11, line 64, the disclosures of the aforementioned patents are incorporated herein by reference. Spiro(indoline) pyrans are also described in the text, *Techniques in Chemistry*, Volume III, "Photochromism", Chapter 3, Glenn H. Brown, Editor, John Wiley and Sons, Inc., New York, 1971.

In another non-limiting embodiment, polymerizable photochromic materials, such as polymerizable naphthoxazines disclosed in U.S. Pat. No. 5,166,345 at column 3, line 36 to column 14, line 3; polymerizable spirobenzopyrans disclosed in U.S. Pat. No. 5,236,958 at column 1, line 45 to column 6, line 65; polymerizable spirobenzopyrans and spirobenzothiopyrans disclosed in U.S. Pat. No. 5,252,742 at column 1, line 45 to column 6, line 65; polymerizable fulgides disclosed in U.S. Pat. No. 5,359,085 at column 5, line 25 to column 19, line 55; polymerizable naphthacenediones disclosed in U.S. Pat. No. 5,488,119 at column 1, line 29 to column 7, line 65; polymerizable spirooxazines disclosed in U.S. Pat. No. 5,821,287 at column 3, line 5 to column 11, line 39; polymerizable polyalkoxylated naphthopyrans disclosed in U.S. Pat. No. 6,113,814 at column 2, line 23 to column 23, line 29; and the polymerizable photochromic compounds disclosed in WO97/05213 and application Ser. No. 09/828,260 filed Apr. 6, 2001 can be used. The disclosures of the aforementioned patents on polymerizable photochromic materials are incorporated herein by reference.

Other non-limiting embodiments of photochromic materials that can be used include organo-metal dithiozonates, e.g., (arylazo)-thioformic arylhydrazidates, e.g., mercury dithizonates which are described in, for example, U.S. Pat. No. 3,361,706 at column 2, line 27 to column 8, line 43; and fulgides and fulgimides, e.g., the 3-furyl and 3-thienyl fulgides and fulgimides, which are described in U.S. Pat. No. 4,931,220 at column 1, line 39 through column 22, line 41, the disclosures of which are incorporated herein by reference.

An additional non-limiting embodiment is a form of organic photochromic material resistant to the effects of a polymerization initiator that can also be used in the photochromic articles of the present invention. Such organic photochromic materials include photochromic compounds encapsulated in metal oxides, the latter of which are described in U.S. Pat. Nos. 4,166,043 and 4,367,170 at column 1 line 36 to column 7, line 12, which disclosure is incorporated herein by reference.

In another non-limiting embodiment, inorganic photochromic systems contemplated for use with the TDVA materials of the present invention typically contain crystallites of silver halide, cadmium halide and/or copper halide. Other non-limiting inorganic photochromic glass systems can be prepared by the addition of europium (II) and/or cerium(III) to a soda-silica glass. Such inorganic photochromic glass systems are described in Kirk Othmer Encyclopedia of Chemical Technology, 4th Edition, Volume 6, pages 322-325, which disclosure is incorporated herein by reference. In one contemplated non-limiting embodiment, the TDVA materials could be used in an at least partial coating or film interposed between the source of radiation and the inorganic photochromic system.

The photochromic materials described herein, e.g., the TDVA materials of the present invention and other photochromic materials, can be chosen from a variety of materials. Non-limiting examples include: of course, a single photochromic compound; a mixture of photochromic compounds; a material comprising at least one photochromic compound, such as a plastic polymeric resin or an organic monomeric or oligomeric solution; a material such as a monomer or polymer to which at least one photochromic compound is chemically bonded; a material comprising and/or having chemically bonded to it at least one photochromic compound, the outer surface of the material being encapsulated (encapsulation is a form of coating), for example with a polymeric resin or a protective coating such as a metal oxide that prevents contact of the photochromic material with external materials such as oxygen, moisture and/or chemicals that have a negative effect on the photochromic material, such materials can be formed into a particulate prior to applying the protective coating as described in U.S. Pat. Nos. 4,166,043 and 4,367,170; a photochromic polymer, e.g., a photochromic polymer comprising photochromic compounds bonded together; or mixtures thereof.

The organic photochromic materials and TDVA materials of the present invention to be used in a photochromic article can be associated with a polymeric organic host material or other substrate by various means. In a series of non-limiting embodiments, they can be incorporated, e.g., dissolved and/or dispersed, into the host material, polymerized with other components of the host material, e.g., in a reaction injection molding, and/or incorporated into an at least partial coating or film applied to a substrate, e.g., an at least partially cured polymeric coating or film applied to one surface of the substrate.

In one non-limiting embodiment, a photochromic article adapted to exhibit an activated optical density response loss of 50 percent or less as measured in the Photochromic Temperature Dependence Test can be prepared by a method comprising:

a) obtaining a substrate;

b) obtaining at least one photochromic material adapted to change from an unactivated form to an activated form upon exposure to actinic radiation; the activated form changing from more absorbing to less absorbing of radiation in the absorption region of the unactivated form as the temperature increases from 10° C. to 35° C.;

c) introducing the photochromic material together with the substrate by a method chosen from:
  i) introducing photochromic material (b) with the starting materials used to form the substrate;
  ii) at least partially imbibing photochromic material (b) into at least one surface of the substrate;
  iii) applying at least a partial coating of a polymeric coating composition comprising photochromic material (b) to at least one surface of the substrate;
  iv) at least partially connecting a superstrate comprising photochromic material (b) to at least one surface of the substrate; or
  v) combinations of i), ii), iii) or iv).

In another non-limiting embodiment, the aforementioned method further comprises adding a photochromic material (c) that is different from photochromic material (b), in (c) (i), (ii), (iii), (iv) or (v).

An alternate non-limiting embodiment for producing a photochromic article adapted to exhibit an unactivated state luminous transmittance of greater than 70 percent at 23° C. and a difference of 20 percent or less between the activated state luminous transmittance at saturation measured at 10° C. and the activated state luminous transmittance at saturation measured at 35° C., the photochromic article being activated by simulated sunlight from a xenon arc lamp set at 6.7 Watts/meter$^2$ UVA and 50,000 lumens/meter$^2$; the method comprising:
  a) obtaining a substrate;
  b) obtaining at least one photochromic material adapted to change from an unactivated form to an activated form upon exposure to actinic radiation; the activated form changing from more absorbing to less absorbing of radiation in the absorption region of the unactivated form as the temperature increases from 10° C. to 35° C.;
  c) introducing the photochromic material with the substrate by a method chosen from the aforementioned (c), (i), (ii), (iii), (iv) or (v). In another non-limiting embodiment, this method further comprises adding a photochromic material (c) that is different from photochromic material (b), in (c) (i), (ii), (iii), (iv) or (v).

Potential substrates for the application of coatings containing TDVA materials, a mixture of TDVA materials and other photochromic materials or a coating of TDVA materials interposed between the source of radiation and other photochromic materials include any type of material. Non-limiting examples include, paper, glass, ceramics, wood, masonry, textiles, metals and polymeric organic host materials.

Each of the TDVA materials with or without the other photochromic materials described herein can be used in amounts (or in a ratio) such that an organic host material or substrate to which the TDVA material or mixture of TDVA material and other photochromics is associated, exhibits a desired resultant color, e.g., a substantially neutral color when activated with unfiltered sunlight, e.g., as near a neutral color as possible given the colors of the activated photochromic compounds, and an optical density response loss of 50% or less as measured in the Photochromic Temperature Dependence Test and/or a difference of 20 percent or less between the activated state luminous transmittance measured at 10° C. and 35° C., when the photochromic article is activated by simulated sunlight from a xenon arc lamp set at 6.7 Watts/meter$^2$ UVA and 50,000 lumens/meter$^2$ and the article exhibits an unactivated state luminous transmittance of greater than 70 percent at 23° C. In one non-limiting embodiment, the TDVA materials could be used to produce articles having a wide range of colors, e.g., pink. Further discussion of neutral colors and ways to describe colors can be found in U.S. Pat. No. 5,645,767 column 12, line 66 to column 13, line 19.

In one non-limiting embodiment, the amount of the TDVA materials to be applied to or incorporated into a polymeric coating composition and/or polymeric host material of the photochromic article of the present invention can vary widely. Typically, a sufficient amount is used to produce the desired optical density response loss and/or difference in percent activated luminous transmittance. Generally such an amount can be described as a temperature dependent reducing amount. The particular amount used depends often upon the optical density response loss and/or difference in percent activated luminous transmittance desired upon irradiation thereof and upon the method used to incorporate or apply the TDVA materials. Typically, in one non-limiting embodiment, the more TDVA material applied or incorporated, the greater is the reduction in the optical density response loss and/or difference in percent activated luminous transmittance up to a certain limit. There is a point after which the addition of any more material will not have a noticeable effect, although more material can be added, if desired.

In another non-limiting embodiment, the amount of the other photochromic materials to be incorporated into a polymeric coating composition and/or polymeric host material can vary widely. Typically, a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate the photochromic materials. Typically, in one non-limiting embodiment, the more photochromic incorporated, the greater is the color intensity up to a certain limit. There is a point after which the addition of any more material will not have a noticeable effect, although more material can be added, if desired.

The relative amounts of the aforesaid TDVA materials or combinations of TDVA materials and other photochromic materials used will vary and depend in part upon the relative intensities of the color of the activated species of such materials, the ultimate color desired, the optical density response loss and/or difference in percent activated luminous transmittance desired and the method of application to the host material and/or substrate. In one non-limiting embodiment, the amount of total photochromic material which includes TDVA materials, other photochromic materials or both, incorporated by imbibition into a photochromic optical host material can vary widely. In alternate non-limiting embodiments, it can range from 0.01 to 2.0, or from 0.05 to 1.0, milligrams per square centimeter of surface to which the photochromic compound is incorporated or applied. The amount of total photochromic substance incorporated or applied to the host material can range between any combination of these values, inclusive of the recited range, e.g., 0.015 to 1.999 milligrams per square centimeter.

In another non-limiting embodiment, the total amount of photochromic material incorporated into a polymerizable composition for forming a coating, film or polymerizate can vary widely, e.g., it can range from 0.01 to 40 weight percent based on the weight of the solids in the polymerizable composition. In alternate non-limiting embodiments, the concentration of photochromic materials ranges from 0.1 to 30 weight percent, from 1 to 20 weight percent, from 5 to 15 weight percent, or from 7 to 14 weight percent. The amount of photochromic materials in the polymerizable composition can range between any combination of these values, inclusive of the recited range, e.g., 0.011 to 39.99 weight percent.

In one non-limiting embodiment, compatible (chemically and color-wise) fixed tint dyes can be added or applied to the host material e.g., polymeric substrate, polymeric coating and/or polymeric film, used to produce the photochromic article to achieve a more aesthetic result, for medical reasons, or for reasons of fashion. The particular dye selected will vary and depend on the aforesaid need and result to be achieved. In one non-limiting embodiment, the dye can be selected to complement the color resulting from the activated photochromic materials, e.g., to achieve a more neutral color or absorb a particular wavelength of incident light. In another non-limiting embodiment, the dye can be selected to provide a desired hue to the host material when the photochromic materials are in an unactivated state.

In various non-limiting embodiments, adjuvant materials can also be incorporated into host material used to produce the photochromic article. Such adjuvants can be used, prior to, simultaneously with or subsequent to application or incorporation of the photochromic material. For example, ultraviolet light absorbers can be admixed with photochromic materials before their addition to the composition or such absorbers can be superposed, e.g., superimposed, as a coating or film between the photochromic article and the incident light.

Further, stabilizers can be admixed with the photochromic materials prior to their addition to the composition to improve the light fatigue resistance of the photochromic materials. Non-limiting examples of stabilizers include hindered amine light stabilizers (HALS), asymmetric diaryloxalamide (oxanilide) compounds and singlet oxygen quenchers, e.g., a nickel ion complex with an organic ligand, polyphenolic antioxidants or mixtures of such stabilizers are contemplated. In one non-limiting embodiment, they can be used alone or in combination. Such stabilizers are described in U.S. Pat. Nos. 4,720,356, 5,391,327 and 5,770,115.

The TDVA materials, other photochromic materials or combinations thereof can be associated with the host material by various methods described in the art. In various non-limiting embodiments, the total amount of photochromic material can be incorporated into the host material used to form the photochromic article by various methods such as by adding the photochromic materials to one or more of the materials used to form the host material. In one non-limiting embodiment when the host material is a polymeric coating or film, the photochromic materials can be dissolved and/or dispersed in an aqueous or organic solvent prior to being incorporated into one or more of the components of the coating or film composition. Alternatively, the photochromic materials can be incorporated into the at least partially cured coating or film by imbibition, permeation or other transfer methods as known by those skilled in the art.

When at least partially cured polymers or polymerizates are used as the host material for the photochromic compounds, various non-limiting embodiments include preparation of a photochromic article by injecting a polymerizable composition with photochromic materials into a mold and polymerizing it by what, for example, is commonly referred to in the art as a cast-in-place process. Polymerizates, e.g., lenses, prepared by cast polymerization in the absence of a photochromic amount of a photochromic material can be used to prepare photochromic articles by applying or incorporating photochromic materials into the polymerizate by art-recognized methods.

Such non-limiting art-recognized methods include: (a) dissolving, dispersing and/or reacting the photochromic materials with or without polymerizable substituents with the materials used to form the polymerizate, e.g., addition of photochromic materials to a polymerizable composition or imbibition of the photochromic materials into the polymerizate by immersion of the polymerizate in a hot solution of the photochromic materials or by thermal transfer; (b) providing the photochromic material as a separate layer between adjacent layers of the polymerizate, e.g., as a part of a polymer film; and (c) applying the photochromic material as part of a coating or film placed or laminated on the surface of the polymerizate. The term "imbibition" or "imbibe" is intended to mean and include permeation of the photochromic materials individually or with other non-photochromic materials into the polymerizate, solvent assisted transfer absorption of the photochromic materials into a polymerizate, vapor phase transfer, and other such transfer mechanisms.

In the context of the present invention, the nature of the polymeric substrate, polymeric film or polymeric coating, collectively referred to as the polymeric host, can vary widely. Generally the polymeric host is such that it allows the TDVA materials of the present invention and other photochromic materials to reversibly transform between their "open" and "closed" forms. In one non-limiting embodiment, the polymeric host used to produce the photochromic articles of the present invention comprises materials adapted to provide thermoplastic or thermosetting organic polymeric materials that are described in the *Kirk-Othmer Encyclopedia of Chemical Technology*, Fourth Edition, Volume 6, pages 669 to 760, which disclosure is incorporated herein by reference.

Such polymeric host materials can be transparent, translucent or opaque; but desirably are transparent or optically clear. In another non-limiting contemplated embodiment is a polymeric material that upon curing forms an at least partially cured polymeric coating chosen from polyurethanes, aminoplast resins, poly(meth)acrylates, e.g., polyacrylates and polymethacrylates, polyanhydrides, polyacrylamides, epoxy resins and polysilanes.

The various coating compositions described below are well known and are made with components and according to methods well understood and appreciated to those skilled in the art. Suitable substrates for the application of coatings containing the TDVA materials or a mixture of the TDVA materials and other photochromic materials include any type of substrate. Non-limiting examples include, paper, glass, ceramics, wood, masonry, textiles, metals and polymeric organic host materials.

The photochromic polyurethane coatings that can be used to prepare the photochromic coated articles of the present invention, in one non-limiting embodiment, can be produced by the catalyzed or uncatalyzed reaction of an organic polyol component and an isocyanate component in the presence of photochromic compound(s). Materials and methods for the preparation of polyurethanes are described in *Ullmann's Encyclopedia of Industrial Chemistry*, Fifth Edition, 1992, Vol. A21, pages 665 to 716. Non-limiting examples of methods and materials, e.g., organic polyols, isocyanates and other components, which can be used to prepare the polyurethane coating are disclosed in U.S. Pat. Nos. 4,889, 413 and 6,187,444B1.

The photochromic aminoplast resin coating composition that can be used to produce the photochromic coated articles of the present invention, in one non-limiting embodiment, can be prepared by combining a photochromic material with the reaction product of a functional component(s) having at least two functional groups chosen from hydroxyl, carbamate, urea or a mixture thereof and an aminoplast resin, e.g., crosslinking agent as described in U.S. Pat. Nos. 4,756,973, 6,432,544B1 and 6,506,488.

Photochromic polysilane coating compositions contemplated for use in preparing the photochromic coated articles of the present invention, in one non-limiting embodiment, are prepared by hydrolyzing at least one silane monomer such as glycidoxypropyltrimethoxysilane, vinyltrimethoxysilane, methacryloxypropyltrimethoxysilane, tetramethoxysilane, tetraethoxysilane and/or methyltrimethoxysilane and combining the hydrolyzate with at least one photochromic material as described in U.S. Pat. No. 4,556,605.

Photochromic poly(meth)acrylate coating compositions contemplated for use in preparing the photochromic coated articles of the present invention can be prepared, in one non-limiting embodiment, by combining photochromic materials(s) with mono-, di- or multi-functional (meth) acrylates as described in U.S. Pat. Nos. 6,025,026 and 6,150,430 and WO publication 01/02449 A2.

The polyanhydride photochromic coating composition that can be used to prepare the photochromic coated articles of the present invention can be prepared in one non-limiting embodiment, by the reaction of a hydroxyl-functional component and a polymeric anhydride-functional component in a composition including at least one organic photochromic material as described in U.S. Pat. No. 6,432,544B1. Non-limiting examples of hydroxyl-functional components, anhydride-functional component(s) and other components that can be used to prepare the polyanhydride photochromic coatings are disclosed in U.S. Pat. Nos. 4,798,745, 4,798,746 and 5,239,012.

Photochromic polyacrylamide coating compositions contemplated for use in preparing the photochromic coated articles of the present invention, in one non-limiting embodiment, can be prepared by combining a photochromic material with the free radical initiated reaction product of a polymerizable ethylenically unsaturated composition comprising N-alkoxymethyl(meth)acrylamide and at least one other copolymerizable ethylenically unsaturated monomer as described in U.S. Pat. No. 6,060,001. Methods for preparing N-alkoxymethyl(meth)acrylamide functional polymer are described in U.S. Pat. No. 5,618,586.

The photochromic epoxy resin coating compositions that can be used to prepare the photochromic coated articles of the present invention, in one non-limiting embodiment, can be prepared by combining photochromic compound(s), epoxy resins or polyepoxides and curing agents as described in U.S. Pat. Nos. 4,756,973 and 6,268,055B1.

In another non-limiting embodiment, the types of photochromic polymeric coatings comprising the film-forming polymers and the TDVA materials of the present invention with or without other photochromic compounds include paints, e.g., a pigmented liquid or paste used for the decoration, protection and/or the identification of a substrate; and inks, e.g., a pigmented liquid or paste used for writing and printing on substrates such as in producing verification marks on security documents, e.g., documents such as banknotes, passport and drivers' licenses, for which authentication or verification of authenticity may be desired.

Application of the polymeric coating can be by any of the methods used in coating technology, non-limiting examples include, spray coating, spin coating, spin and spray coating, spread coating, curtain coating, dip coating, casting or roll-coating and methods used in preparing overlays, such as the method of the type described in U.S. Pat. No. 4,873,029. The application method selected also depends on the thickness of the desired coating.

The thickness of the coatings on the photochromic articles of the present invention can vary widely. Coating having a thickness ranging from 1 to 50 microns can be applied by the methods used in coating technology. Coating of a thickness greater than 50 microns can require the application of multiple coatings or molding methods typically used for overlays. In alternate non-limiting embodiments, the coating can range in thickness from 1 to 10,000 microns, from 5 to 1,000, from 8 to 400 or from 10 to 250 microns. The thickness of the polymeric coating can range between any combination of these values, inclusive of the recited range, e.g., a thickness of from 20 to 200 microns.

Following application of the polymeric coating to the surface of the substrate, in one non-limiting embodiment, the coating is at least partially cured. In another non-limiting embodiment, the methods used for curing the photochromic polymeric coating include the methods used for forming at least partially cured polymers. Such methods include radical polymerization, thermal polymerization, photopolymerization or a combination thereof. Additional non-limiting methods include irradiating the host material with infrared, ultraviolet, gamma or electron radiation so as to initiate the polymerization reaction of the polymerizable components. This can be followed by a heating step.

In one non-limiting embodiment, if required and if appropriate, the surface of the substrate to be coated is cleaned prior to applying the photochromic polymeric coating to produce the photochromic article of the present invention. This can be done for the purposes of cleaning and/or promoting adhesion of the coating. Effective treatment techniques for plastics and glass are known to those skilled in the art.

In some non-limiting embodiments, it may be necessary to apply a primer to the surface of the substrate before application of the photochromic polymeric coating. The primer can serve as a barrier coating to prevent interaction of the coating ingredients with the substrate and vice versa, and/or as an adhesive layer to adhere the photochromic polymeric coating to the substrate. Application of the primer can be by any of the methods used in coating technology such as, for example, spray coating, spin coating, spin and spray coating, spread coating, dip coating, casting or roll-coating.

The use of protective coatings, some of which can contain polymer-forming organosilanes, as primers to improve adhesion of subsequently applied coatings has been described in U.S. Pat. No. 6,150,430, which disclosure is incorporated herein by reference. In one non-limiting embodiment, non-tintable coatings are used. Non-limiting examples of commercial coating products include SIL-VUE® 124 and HT-GARD® coatings, available from SDC Coatings, Inc. and PPG Industries, Inc., respectively. In addition, depending on the intended use of the coated article, in one non-limiting embodiment, it can be necessary to apply an appropriate protective coating(s), such as an abrasion resistant coating and/or coatings that can serve as oxygen barriers, onto the exposed surface of the coating composition to prevent scratches from the effects of friction and abrasion and interactions of oxygen with the photochromic compounds, respectively.

In some cases, the primer and protective coatings are interchangeable, e.g., the same coating can be used as the primer and the protective coating(s). Non-limiting examples of hardcoats include those based on inorganic materials such as silica, titania and/or zirconia as well as organic hardcoats of the type that are ultraviolet light curable. In one non-limiting embodiment, such protective coatings can be applied to the surface of photochromic articles comprising at least partially cured polymers containing photochromic materials.

In another non-limiting embodiment, the article of the present invention comprises a substrate to which a primer is applied followed by the photochromic polymeric coating and a protective hardcoat. In a further non-limiting embodiment, the protective hardcoat is an organosilane hardcoat.

In additional non-limiting embodiments, other coatings or surface treatments, e.g., a tintable coating, antireflective surface, etc., can also be, applied to the photochromic articles of the present invention. An antireflective coating, e.g., a monolayer or multilayer of metal oxides, metal fluorides, or other such materials, can be deposited onto the photochromic articles, e.g., lenses, of the present invention through vacuum evaporation, sputtering, or some other method.

In a further non-limiting embodiment, the photochromic article comprising an at least partially cured polymer and at least one TDVA material with or without other photochromic material further comprises a superstrate, e.g., a film or sheet comprising at least one organic polymeric material. The photochromic material can be located in the superstrate, the at least partially cured polymer or both. The organic polymeric material of the superstrate is the same as the organic polymeric material described hereinafter as the substrate or host material. Non-limiting examples of the organic polymeric materials include thermosetting or thermoplastic materials, for example a thermoplastic polyurethane superstrate.

In a still further non-limiting embodiment, the superstrate can be connected to the polymer surface directly, but does not become thermally fused to the substrate. In another non-limiting embodiment, the superstrate can be adherently bonded to the substrate by becoming thermally fused with the subsurface of the substrate. General conditions under which superstrates are adherently bonded to a substrate are known to those skilled in the art. Non-limiting conditions for adherently laminating a superstrate to a substrate include heating to a temperature of from 250-350° F. (121-177° C.) and applying pressure of from 150 to 400 pounds per square inch (psi) (1034 to 2758 kPa). Sub-atmospheric pressures, e.g., a vacuum, can also be applied to draw down and conform the superstrate to the shape of the substrate as known to those skilled in the art. Non-limiting examples include applying at a sub-atmospheric pressure within the range of from 0.001 mm Hg to 20 mm Hg (0.13 Pa to 2.7 kPa).

After a laminate comprising a superstrate applied to as least one surface of a substrate is formed, it can further comprise a protective coating or film superposed onto the superstrate. Such a protective coating or film, in one non-limiting embodiment, serves as an at least partially abrasion resistant coating or film. Non-limiting types of protective coatings include the aforedescribed hardcoats that are curable by ultraviolet radiation and/or that contain organosilanes. The thickness of the protective coating can vary widely and include the aforementioned range for the photochromic polymeric coatings. Non-limiting types of protective films include those made of organic polymeric materials such as thermosetting and thermoplastic materials. In another non-limiting embodiment, the protective film is a thermoplastic film made of polycarbonate. The thickness of the protective film or sheet can vary widely. Typically, such films have a thickness of from 1 to 20 mils (0.025 to 0.5 mm).

The host material for the TDVA materials and/or other photochromic materials will usually be transparent, but can be translucent or even opaque. The host material need only be pervious to that portion of the electromagnetic spectrum, which activates the photochromic material, e.g., that wavelength of ultraviolet (UV) light that produces the open or colored form of the material and that portion of the visible spectrum that includes the absorption maximum wavelength of the material in its UV activated form, e.g., the open form. In one contemplated non-limiting embodiment, the host color should not be such that it masks the color of the activated form of the photochromic materials, e.g., so the change in color is readily apparent to the observer. Compatible tints may be applied to the host material as described in U.S. Pat. No. 5,645,767 in column 13, line 59 to column 14, line 3.

In one contemplated non-limiting embodiment, the polymeric organic host material can be a solid transparent or optically clear material, e.g., materials having a luminous transmittance of at least 70 percent and are suitable for optical applications, such as optical elements chosen from plano and ophthalmic lenses, ocular devices such as ophthalmic devices that physically reside in or on the eye, e.g., contact lenses and intraocular lenses, windows, automotive transparencies, e.g., windshields, aircraft transparencies, plastic sheeting, polymeric films, etc.

Non-limiting examples of polymeric organic materials which can be used as a host material for the TDVA materials of the present invention with or without other photochromic materials or as a substrate for the photochromic polymeric coating include: poly(meth)acrylates, polyurethanes, polythiourethanes, thermoplastic polycarbonates, polyesters, poly(ethylene terephthalate), polystyrene, poly(alpha methylstyrene), copoly(styrene-methyl methacrylate), copoly (styrene-acrylonitrile), polyvinylbutyral, poly(vinyl acetate), cellulose acetate, cellulose propionate, cellulose butyrate, cellulose acetate butyrate, polystyrene or polymers, such as homopolymers and copolymers prepared by polymerizing monomers chosen from bis(allyl carbonate) monomers, styrene monomers, diisopropenyl benzene monomers, vinylbenzene monomers, e.g., those described in U.S. Pat. No. 5,475,074, diallylidene pentaerythritol monomers, polyol (allyl carbonate) monomers, e.g., diethylene glycol bis(allyl carbonate), vinyl acetate monomers, acrylonitrile monomers, mono- or polyfunctional, e.g., di- or multi-functional, (meth)acrylate monomers such as ($C_1$-$C_{12}$) alkyl (meth)acrylates, e.g., methyl (meth)acrylate, ethyl (meth)acrylate, butyl (meth)acrylate etc., poly(oxyalkylene) (meth)acrylate, poly(alkoxylated phenol (meth)acrylates), diethylene glycol (meth)acrylates, ethoxylated bisphenol A (meth)acrylates, ethylene glycol (meth)acrylates, poly(ethylene glycol) (meth)acrylates, ethoxylated phenol (meth) acrylates, alkoxylated polyhydric alcohol (meth)acrylates, e.g., ethoxylated trimethylol propane triacrylate monomers, urethane (meth)acrylate monomers, such as those described in U.S. Pat. No. 5,373,033, or a mixture thereof. Further examples of polymeric organic host materials are disclosed in the U.S. Pat. No. 5,753,146, column 8, line 62 to column 10, line 34.

In another non-limiting embodiment, transparent copolymers and blends of transparent polymers are also suitable as polymeric materials. The host material can be an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483.

A further non-limiting embodiment is use of the TDVA materials of the present invention and other photochromic materials with optical organic resin monomers used to produce optically clear coatings, films and polymerizates, e.g., materials suitable for optical applications. Examples of non-limiting embodiments include polymerizates of optical resins sold by PPG Industries, Inc. as TRIVEX monomers and under the CR- designation, e.g., CR-307, CR-407 and CR-607. Further non-limiting examples include resins used to prepare hard or soft contact lenses and intraocular devices. Methods for producing both types of contact lenses are disclosed in U.S. Pat. No. 5,166,345, column 11, line 52, to column 12, line 52.

Further non-limiting embodiments of optical resins include the resins used to form soft contact lenses with high moisture content described in U.S. Pat. No. 5,965,630 and extended wear contact lenses described in U.S. Pat. No. 5,965,631.

The present invention is more particularly described in the following examples, which are intended as illustrative only, since numerous modifications and variations therein will be apparent to those skilled in the art.

FIG. 1, which shows the absorbance as a function of temperature for PM-A, was prepared using a concentration of about $4\times10^{-4}$ moles/liter of PM-A in toluene. An Ocean Optics S2000 UV-VIS spectrophotometer (200-900 nanometers(nm)) and the software that came with the system (OoiBase32) were used to collect the data. In order to measure the ultraviolet and visible spectra simultaneously, a tungsten lamp (8 Watt bulb, Ocean Optics LS-1), filtered with 0.5 neutral density filters, provided wavelengths from 500 to 800 nm and an AIS UV-2 deuterium bulb filtered with a Hoya B370 filter (1.5 millimeter (mm) thickness) provided wavelengths from about 290 to 520 nm. The output from both sources was directed through a bifurcated 2 mm optical fiber of half meter length to combine the light from sources and then into a 1 mm optical fiber that was approximately 1 meter in length and was looped to ensure complete mixing of the ultraviolet and visible wavelengths.

The ultraviolet and visible light output from the optical fiber was collimated and directed through a quartz water cell, that held a 1 mm pathlength quartz cuvette containing the photochromic solution, to a collection optical fiber connected to the Ocean Optics S2000 spectrophotometer. The temperature was controlled at 50.3° F. (10.2° C.), 70.2° F. (21.2° C.) and 90° F. (32.2° C.) (+/−0.3° F./0.16° C.). The photochromic solution was activated in the optical bench quartz cell sample holder for approximately 230 seconds at 50 and 70° F., and 180 seconds at 90° F. Activation of the sample was achieved using an Oriel Xe light source, filtered with a 3 mm KG-2 filter and neutral density filters such that the final irradiance was 5.2 Watts/m$^2$ UVA. Note that even at 50° F., 200 seconds was enough time to saturate the photochromic response of the PM-A photochromic compound.

The following photochromic materials were used in the examples described hereinafter. Photochromic materials A through W represent TDVA materials. Photochromic materials AA through HH represent other photochromic materials that were used in conjunction with the TDVA materials. Photochromic materials X, Y and Z represent other organic photochromic materials prepared by methods described in U.S. Pat. No. 5,645,767 and were used in Comparative Examples 1-3.

Photochromic Materials (PM)

PM-A 3-(4-methoxyphenyl)-3-phenyl-6,7,10,11-tetramethoxy-13-ethyl-13-hydroxy-13H-3H-indeno[2,'3,'3,4]naphtho [1,2-b]pyran PM-B 3,3-di(4-methoxyphenyl)-6,11-dimethoxy-13-butyl-13-ethoxy-13H-3H-indeno[2,'3,'3,4]naphtho[1,2-b]pyran PM-C 3-(4-methoxyphenyl)-3-phenyl-6,11-dimethoxy-13-methyl-13-(2-(2-hydroxyethoxy)ethoxy)-13H-3H-indeno[2,'3,'3,4]naphtho[1,2-b]pyran PM-D 3-(4-morpholinophenyl)-3-phenyl-11-morpholino-13,13-dimethyl-13H-3H-indeno[2,'3,'3,4]naphtho[1,2-b]pyran PM-E 3,3-di(4-methoxyphenyl)-11-morpholino-13,13-dimethyl-13H-3H-indeno[2,'3,'3,4]naphtha[1,2-b]pyran PM-F 3-(4-methoxyphenyl)-3-phenyl-10,11-dimethoxy-13,13-dimethyl-13H-3H-indeno-[2,'3,'3,4]naphtho[1,2-b]pyran PM-G 3-(4-methoxyphenyl)-3-phenyl-13,13-dimethyl-13H-3H-indeno[2,'3,'3,4]naphtha[1,2-b]pyran PM-H 3,3-di(4-methoxyethoxyphenyl)-11-morpholino-13,13-dimethyl-13H-3H-indeno[2,'3,'3,4]naphtho[1,2-b]pyran PM-I 2,2-diphenyl-5-(2-hydroxy)propyl)-8-methoxy-2H-naphtho[1,2-b]pyran PM-J 3,3-diphenyl-6,11-dimethoxy-13-acetoxy-13H-3H-indeno[2,'3,'3,4]naphtho[1,2-b]pyran PM-K 3-(4-methoxyphenyl)-3-phenyl-6,10,11-trimethoxy-13-methyl-13-hydroxy-13H-3H-indeno[2,'3,'3,4]naphtho [1,2-b]pyran PM-L 3-(4-methoxyphenyl)-3-phenyl-6,10,11-trimethoxy-13-butyl-13-hydroxy-13H-3H-indeno[2,'3,'3,4]naphtho [1,2-b]pyran PM-M 2,2-diphenyl-5-carbomethoxy-6-phenyl-9-methoxy-2H-naphtho[1,2-b]pyran PM-N 3-(3,4-dimethoxyphenyl)-3-(4-methoxyphenyl)-11-morpholino-13,13-dimethyl-13H-3H-indeno[2,'3,'3,4] naphtho[1,2-b]pyran PM-O 7-(4-morpholino-2-fluorophenyl)-7-(3,4-dimethoxyphenyl)-2-pentyl-4-oxo-4H-7H-[1,3] dioxin[5',4':3,4] naphtho[1,2-b]pyran PM-P 3-(4-methoxyphenyl)-3-(4-morpholinophenyl)-11-morpholino-13,13-dimethyl-13H-3H-indeno[2,'3,'3,4] naphtho[1,2-b]pyran PM-Q 3,3-diphenyl-13,13-dimethyl-13H-3H-indeno[2,'3,'3, 4] naphtho[1,2-b]pyran PM-R 3-(4-morpholinophenyl)-3-phenyl-6,11-dimethoxy-13-methoxy-13-methyl-13H-3H-indeno[2,'3,'3,4]naphtho [1,2-b]pyran PM-S 2,2,7,7-tetraphenyl-4-oxo-2,3,4,7-tetrahydro-1H-pyrimidino[5',4':3,4]naphtho[1,2-b]pyran PM-T 3,3 di(4-dimethoxyphenyl)-6,7,10,11-tetramethoxy-13,13-dimethyl-13H-3H-indeno[2,'3,'3,4]naphtho[1,2-b] pyran PM-U 3-(4-methoxyphenyl)-3-phenyl-6,11-dimethoxy-13-ethyl-13-hydroxy-13H-3H-indeno[2,'3,'3,4]naphtho[1,2-b]pyran;

PM-V 2,2 diphenyl-5-(2-(2-hydroxyethoxy)ethoxy) carbolic,6-(4-methoxyphenyl)-9-methoxy-2H-naphtho[1,2.6]pyran;

PM-W 3-phenyl-3-(2-fluorophenyl)-3H-naphtho[2,1-b]pyran.

PM-X 2,2 diphenyl-5-(2-ethoxy-2-oxo-ethoxycarbonyl)8-methyl-2H-naphtho[1,2-b]pyran PM-Y 2,2 diphenyl-5-methoxycarbonyl-8-methyl-2H-naphtho-[1,2-b]pyran PM-Z 3,3-di(4methoxyphenyl)-6,11-dimethyl-13-(1-methylethyl)-13-hydroxy-indeno[2,'3,'3,4]naphtho[1,2-b]pyran PM-AA A naphtho[1,2-b]pyran that exhibits a blue-purple color when irradiated with ultraviolet light.

PM-BB A naphtho[1,2-b]pyran that exhibits a orange color when irradiated with ultraviolet light.

PM-CC A naphtho[1,2-b]pyran that exhibits a yellow-orange color when irradiated with ultraviolet light.

PM-DD A naphtho[1,2-b]pyran that exhibits a yellow-green color when irradiated with ultraviolet light.

PM-EE A naphtho[1,2-b]pyran that exhibits a red color when irradiated with ultraviolet light.

PM-FF A naphtho[1,2-b]pyran that exhibits a purple color when irradiated with ultraviolet light.

PM-GG A naphtho[1,2-b]pyran that exhibits a red-orange color when irradiated with ultraviolet light.

PM-HH A naphtho[1,2-b]pyran that exhibits a purple color when irradiated with ultraviolet light.

PM-II A naphtho[1,2-b]pyran that exhibits a greenish-blue color when irradiated with ultraviolet light.

Examples 1-42 are of photochromic compositions used to produce articles demonstrating an optical density response loss of 50 percent or less as measured in the Photochromic Temperature Dependence Test described in Example 43. Specifically, Examples 1 through 5 are of imbibition coatings each having a single TDVA material; Examples 6 through 11 are of acrylic coating compositions having an individual TDVA material for application to a non-photochromic substrate; Examples 12 through 17 each have an acrylic coating applied at different thicknesses to provide increasing concentrations of TDVA materials to substrates imbibed with a proprietary formulation of photochromic materials; Examples 18A and 18B are of a polyurethane coatings containing TDVA materials applied to a non-photochromic lens; Examples 19 through 22 are of a cast-in-place photochromic acrylic chip having applied thereto an acrylic coating containing TDVA materials; Examples 23 to 40 are of imbibition coatings having a mixture of photochromic materials and TDVA materials and Examples 41 and 42 are the articles resulting from the use of the imbibition compositions of Examples 39 and 40 to which an acrylic coating containing a single TDVA material was applied thereto.

Comparative Examples 1-3 represent Compositions 1-3 described in Table 2 of U.S. Pat. No. 5,753,146 with the photochromic materials imbibed into the test substrate. Comparative Examples 4-11 represent commercially available plastic lenses that incorporate organic photochromic compounds and activate to a grey color.

Acrylic Coating #1

The following materials were added in the order described to a suitable vessel equipped with an agitator and means for heating.

| Materials | Weight Percent* |
|---|---|
| Charge 1 | |
| Irgacure ® 819[1] | 0.10 |
| TPO[2] | 0.14 |
| Tinuvin ® 622LD[3] | 0.91 |
| Irganox ® 245[4] | 1.35 |
| NMP[5] | 6.82 |
| Charge 2 | |
| TMPTMA[6] | 9.05 |
| BPA 2EO DMA[7] | 7.33 |
| BPA 10EO DMA[8] | 74.30 |

*Weight Percent is based on the total weight of the coating composition.
[1] A photoinitiator reported to be phenylbis (2,4,6-trimethyl benzoyl) phosphine oxide available from Ciba Specialty Chemicals Corp.
[2] 2,4,6-trimethyl benzoyl diphenyl phosphine oxide.
[3] A hindered amine ultraviolet light stabilizer available from Ciba Specialty Chemicals Corp.
[4] An antioxidant/stabilizer reported to be triethylene glycol bis [3-(3-(tert)-butyl-4-hydroxy-5-methylphenyl)] propionate available from Ciba Specialty Chemicals Corp.
[5] N-methylpyrrolidone solvent of 99 percent purity.
[6] Trimethylolpropane trimethacrylate.
[7] Bisphenol A ethoxylated (IEO/phenol) dimethacrylate.
[8] Bisphenol A ethoxylated (5EO/phenol) dimethacrylate.

After Charge 1 was added to the vessel, the agitator was turned on and the solution was heated to about 60° C. to dissolve the components. Charge 2 was added and the resulting solution was maintained at about 60° C. and mixed for 1½ hours.

Acrylic Coating #2

The following materials were added in the order described to a suitable vessel equipped with an agitator and means for heating.

| Materials | Weight Percent |
|---|---|
| Charge 1 | |
| NMP[5] | 12.24 |
| Irganox ® 245[4] | 2.44 |
| Tinuvin ® 622LD[3] | 3.26 |
| Charge 2 | |
| TPO[2] | 0.24 |
| BAPO[9] | 0.16 |
| Charge 3 | |
| BPA 2EODMA[7] | 14.68 |
| BPA 10EODMA[8] | 58.68 |
| TMPTMA[6] | 8.14 |
| Fluorad ® FC-431[10] | 0.16 |

[9] Bis (2,6-dimethoxybenzoyl)phenylphosphine oxide.
[10] A flourinated surfactant available from 3M.

After Charge 1 was added, the agitator was turned on and the solution was mixed for 15 minutes. Charge 2 was added and the solution was mixed for 15 minutes. Charge 3 was added and the solution was mixed for 30 minutes.

Imbibition Coating

The following materials were added in the order and manner described to a vessel equipped with an agitator and means for heating.

| Materials | Weight Percent |
|---|---|
| Charge 1 | |
| Tetrahydrofurfuryl alcohol | 25 |
| Diethylene glycol dimethyl ether | 29 |
| NMP | 12 |
| Dowanol ® PNB[11] | 16 |
| Hydroxypropyl cellulose | 10 |
| Silica | 2 |
| Charge 2 | |
| Photochromic Composition | 4 |
| Stabilizers: Tinuvin ® 144 and Irganox ® 3114A in a 70/30 weight ratio | 2 |

[11] Reported to be propylene glycol n-butyl ether and is available from Dow Chemical Co.

Charge 1 was added to the vessel and the solution was mixed until the components dissolved. Charge 2 was added and the resulting mixture was heated and mixed until the materials were dissolved.

EXAMPLE 1

Photochromic N was used as the photochromic composition in the Imbibition Coating except that Tinuvin® 144 was used as the only stabilizer at a concentration of 2 weight percent.

EXAMPLE 2

The procedure of Example 1 was followed except that Photochromic 0 was used as the photochromic composition in the Imbibition Coating.

EXAMPLE 3

The procedure of Example 1 was followed except that Photochromic E was used as the photochromic composition in the Imbibition Coating.

EXAMPLE 4

The procedure of Example 1 was followed except that Photochromic H was used as the photochromic composition in the Imbibition Coating.

EXAMPLE 5

The procedure of Example 1 was followed except that Photochromic P was used as the photochromic composition in the Imbibition Coating.

EXAMPLE 6

Photochromic compound C (PM-C), approximately 1.0 weight percent, based on the total weight of the coating composition, was added to a vessel containing Acrylic Coating #1 with one drop of FC-431 surfactant. The resulting mixture was heated with stirring until the photochromic compound dissolved.

EXAMPLE 7

The process of Example 6 was followed except that PM-J was used.

EXAMPLE 8

The process of Example 6 was followed except that PM-G was used.

EXAMPLE 9

The process of Example 6 was followed except that PM-B was used.

EXAMPLE 10

The process of Example 6 was followed except that PM-K was used.

Example 11

The process of Example 6 was followed except that PM-L was used.

EXAMPLE 12

The coating composition of Example 6 was applied at increasing thicknesses (indicated by increasing levels of absorbance @ 390 nm) to test samples imbibed with a proprietary combination of photochromic compounds.

EXAMPLE 13

The process of Example 12 was followed except that the coating composition of Example 7 was used.

EXAMPLE 14

The process of Example 12 was followed except that the coating composition of Example 8 was used.

EXAMPLE 15

The process of Example 12 was followed except that the coating composition of Example 9 was used.

EXAMPLE 16

The process of Example 12 was followed except that the coating composition of Example 10 was used.

EXAMPLE 17

The process of Example 12 was followed except that the coating composition of Example 11 was used.

EXAMPLE 18A

The procedure of Example 9 of U.S. Pat. No. 6,187,444 B1 was followed except that photochromic compounds Nos. 1, 2 and 3 in Charge 1 were replaced by PM-C used at a concentration of about 3.6 percent in Example 18A1 and about 7.0 percent in Example 18A2, and a proprietary polyurethane composition was used in Charges 2 and 3. The percent weight of photochromics in the coating composition was based on the total weight of the polyurethane forming resins in Charges 2 and 3.

EXAMPLE 18B

The procedure of Example 9 of U.S. Pat. No. 6,187,444B1 was followed except that Photochromic compounds Nos. 1, 2 and 3 were replaced by PM-U and PM-V in a 66/34 weight ratio at a concentration of about 10 weight percent, based on the total weight of the polyurethane composition.

EXAMPLE 19

Part A

A quantity of PM-II, calculated to yield a 1.5×10-3 molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold at 60° C. for 16 hours. After the mold was opened, the polymer sheet was cut using a diamond blade saw into 2 inch (5.1 centimeters) test squares.

Part B

PM-I, approximately 2 weight percent, was added to a vessel containing Acrylic Coating #2. The resulting mixture was heated with stirring until the photochromic compound dissolved.

EXAMPLE 20

The procedure of Example 19 was followed except that in Part B, approximately 3 weight percent of PM-I was used.

EXAMPLE 21

The procedure of Example 19 was followed except that in Part B, approximately 2 weight percent of PM-W was used.

EXAMPLE 22

The procedure of Example 19 was followed except that in Part B, approximately 3 weight percent of PM-W was used.

EXAMPLE 23

PM-C, PM-DD, PM-BB, PM-B, PM-G and PM-CC in a 30/26/18/15/7/4 weight ratio were used as a Photochromic Composition in the Imbibition Coating.

EXAMPLE 24

PM-N, PM-BB, PM-CC, PM-B, PM-DD and PM-C in a 10/15/5/17/27/25 weight ratio were used as the Photochromic Composition in the Imbibition Coating.

EXAMPLE 25

PM-CC, PM-D, PM-E, PM-EE and PM-FF in a 30/22/18/15/15 weight ratio were used as the Photochromic Composition in the Imbibition Coating designated Example 25A. In the imbibition coating designated Example 25B, the fixed tints Keyplast Morplast Blue B (blue-green) and Keystone Magentan RB (blue-red) were added at a level of 0.03 weight percent. In the imbibition coating designated Example 25C, the fixed tints Keystone Blue RR (blue-green) and Keystone Magentan RB (blue-red) were added at a level of 0.03 weight percent.

EXAMPLE 26

PM-CC, PM-E and PM-EE in a 25/45/30 weight ratio were used as the Photochromic Composition in the Imbibition Coating.

EXAMPLE 27

PM-CC, PM-HH, PM-D, PM-E, and PM-GG in a 7/25/15/30/23 weight ratio were used as the Photochromic Composition in the Imbibition Coating.

EXAMPLE 28

PM-CC, PM-G, PM-DD, PM-EE and PM-H in a 24/2/4/25/45 weight ratio were used as the Photochromic Composition in the Imbibition Coating.

EXAMPLE 29

PM-M, PM-C and PM-A in a 53/33.5/13.5 weight ratio were used as the Photochromic Composition in the Imbibition Coating.

EXAMPLE 30

The photochromic compounds of Example 29 were used in the same weight ratio as the Photochromic Composition in the Imbibition Coating except that the time for imbibition was 7 hours instead of 6 hours.

EXAMPLE 31

PM-AA, PM-BB, PM-CC, PM-B, PM-T, PM-C and PM-Q in a 17/15/03/10/20/24/11 weight ratio were used as the Photochromic Composition in the Imbibition Coating.

EXAMPLE 32

PM-AA, PM-BB, PM-CC, PM-T, PM-C, PM-Q and PM-R in a 17/13/03/20/25/12/10 weight ratio were used as the Photochromic Composition in the Imbibition Coating.

EXAMPLE 33

PM-CC, PM-S, and PM-D in a 10/30/60 weight ratio were used as the Photochromic Composition in the Imbibition Coating.

EXAMPLE 34

PM-CC, PM-E, PM-D, and PM-EE in a 25/25/20/30 weight ratio were used as the Photochromic Composition in the Imbibition Coating.

EXAMPLE 35

PM-CC, PM-DD, PM-E, and PM-EE in a 25/05/45/25 weight ratio were used as the Photochromic Composition in the Imbibition Coating.

EXAMPLE 36

PM-CC, PM-DD, PM-E, and PM-O in a 25/05/45/25 weight ratio were used as the Photochromic Composition in the Imbibition Coating.

EXAMPLE 37

PM-CC, PM-DD, PM-D, and PM-FF in a 35/08/35/22 weight ratio were used as the Photochromic Composition in the Imbibition Coating.

EXAMPLE 38

PM-CC, PM-DD, PM-N, and PM-O in a 25/05/25/45 weight ratio were used as the Photochromic Composition in the Imbibition Coating.

EXAMPLE 39

PM-CC, PM-E and PM-FF in a 30/35/35 weight ratio were used as the Photochromic Composition in the Imbibition Coating.

EXAMPLE 40

PM-CC, PM-D and PM-FF in a 32/35/33 weight ratio were used as the Photochromic Composition in the Imbibition Coating.

EXAMPLE 41

The process of Example 6 was followed except that Acrylic Coating #2 and PM-I at a level of 3 weight percent, based on the total weight of the coating composition; were used. This coating was applied to the test sample imbibed with Example 39.

EXAMPLE 42

The process of Example 41 was followed except that the coating was applied to the imbibed test sample of Example 40.

COMPARATIVE EXAMPLES 1-3

Compositions 1,2 and 3 from Table 2 of U.S. Pat. No. 5,753,146 were used as the Photochromic Composition in the Imbibition Coating except that Tinuvin® 144 was used as the only stabilizer at a concentration of 2 weight percent. In Comparative Example 1, PM-Z and PM-X in a 60/40 weight ratio were used as the Photochromic Composition in the Imbibition Coating. In Comparative Example 2, PM-Z and PM-Y in a 60/40 weight ratio were used as the Photochromic Composition in the Imbibition Coating. In Comparative Example 3, PM-Z and PM-X in a 35/65 weight ratio were used as the Photochromic Composition in the Imbibition Coating.

COMPARATIVE EXAMPLES 4-11

The commercially available plastic lenses described and listed below were used as Comparative Examples. Each lens was a plano type lens that reportedly activated to a grey color. Each lens was tested in duplicate and the average of the result was reported hereinafter in Table 5.

| CE # | Lens Description | Thickness |
|---|---|---|
| 4 | Corning SunSensors ® | 1.8 mm |
| 5 | Hoya Hilux ® | 2.0 mm |
| 6 | Transitions ® Next Generations | 2.0 mm |
| 7 | Optical Dynamics ® | 2.1 mm |
| 8 | Transitions ® Polycarbonate | 2.0 mm |
| 9 | Rodenstock ® ColorMatic Extra | 1.9 mm |
| 10 | Transitions ® III 1.50 | 2.0 mm |
| 11 | Sola ® Velocity | 2.0 mm |

EXAMPLE 43

The Photochromic Temperature Dependence Test is described herein. Part A describes the preparation of the samples having the TDVA materials with or without other photochromic materials. Part B describes the testing of the examples.

Part A

The test samples used for imbibition of photochromic compounds were prepared using CR-607® monomer available from PPG Industries, Inc. The text samples were prepared in a manner similar to that suggested in the PPG CR-607 Monomer-Product Bulletin using 2.5 parts per hundred of monomer (pph) of diisopropyl peroxydicarbonate, a thermal initiator. After the initiator was dissolved in the monomer by mixing, the monomer was poured into glass molds measuring 12 inches by 12 inches by 0.08 inch (30.5 cm by 30.5 cm by 0.2 cm). The molds were cured according to the following cycle. Hold for 6 hours at 36° C.; ramp up to 56° C. over 8 hours at 56° C., ramp up to 72° C.; after 8 hours at 72° C., remove sample and cool to 60° C. and demold.

Afterwards, the cured sheets were cut into two inch (5.1 centimeters) test squares. For Examples 1-5, the test squares were imbibed with single photochromic materials, and for Examples 12-17, the test squares were imbibed with the proprietary photochromic formulation as the photochromic combination in the imbibition coating. The imbibition coating was applied to the test samples by dispensing a quantity of imbibition coating on the test sample and spinning at about 1500 rpm's for four seconds to produce a wet film-weight of about 0.27 to about 0.29 grams. The resulting films were dried under an infrared light for about 20 minutes and placed in an oven at 135° C. for the time indicated hereinafter. Afterward, the imbibed test samples were washed with soap and rinsed with water.

The photochromic compositions of Examples 6-11 were applied by spin coating to 76 mm diameter lenses. The lenses were made of CR-39® monomer by SOLA USA and were not photochromic. The lenses were wiped with an acetone soaked lint-free paper tissue and treated with oxygen plasma in a PLASMA TECH/PLASMA finish microwave gas plasma system. The treatment conditions were as follows: power set to 100 watts; gas pressure was 42 pascals; a gas flow rate of 100 mL/minute was used; and the processing time was 60 seconds. The coatings were applied to the lenses at various spin speeds and time intervals in order to produce a particular absorbance of the cured film. For example, the coating composition of Example 6 was spun at 2000 rpm for 4 seconds to produce a cured coated lens having an absorbance at 390 nanometers of 0.53.

The coatings of Examples 6-11 were applied at different spin speeds and times to produce the desired absorbance in Examples 12-17. For example, the coating of Example 6 was spun at 2000 rpm for 17 seconds to produce a cured coating having an absorbance of 0.21 in Example 12. Prior to the application of the acrylic coating, the test samples were treated with oxygen plasma for one minute using the same treatment conditions previously listed.

The coated lenses of Examples 6-17 were cured in one pass on a conveyor belt at a speed of 2.3 feet per minute, four inches beneath a 10 inch long ultraviolet light "Type V" lamp from Eye Ultraviolet, Inc. rated at an output of 160 Watts/cm—(400 watts/inch). The ultraviolet light line was purged with nitrogen to less than 100 parts per million of oxygen.

The photochromic polyurethane compositions of Examples 18A1 and A2 were applied by spin coating at about 2000 rpm for 3, 8and seconds for A1 and 3 and 6 seconds for A2 to non-photochromic polycarbonate lenses obtained from Gentex, Inc. and prepared as done hereinabove for Examples 6-17. The coated lenses were cured at 140° C. for 1 hour and 15 minutes. The coating composition of Example 18B was applied using the same procedure as Example 18A except that the solution was dispensed for 3 to 4 seconds.

The photochromic acrylic compositions of Examples 19B, 20, 21 and 22 were applied to the photochromic chips of Example 19A by dispensing the solutions for the time necessary while the lens was spinning to result-in a cured coating having a thickness of about 20 microns. The coated lenses were cured as previously described in the conveyor at a speed of 2.3 feet per minute.

Examples 1-5, 12-17, 23-40 and CE1-3 were prepared using the imbibition composition with the appropriate photochromic combination and were imbibed at 135° C. for the times listed below.

| Example # | Time |
| --- | --- |
| 27A | 1 hour |
| 27B | 2 hours |
| 27C | 3 hours |
| 23, 27D | 4 hours |
| 24-26, 28, 31-33, and 39-40 | 4.5 hours |
| 29 | 6 hours |
| 30 | 7 hours |
| 12-17 | 7.5 hours |
| 1-5, 34-38 and CE1-3 | 8 hours |

The coated samples of Examples 41-42 were prepared in the same manner as Examples 19B-22 except that the photochromic test samples of Examples 39 and 40 were used. Comparative Examples 1-3 were prepared using the photochromic combinations of U.S. Pat. No. 5,753,146 and the same methods for imbibition as described herein above.

Part B

The photochromic coated and imbibed lenses prepared in Part A were screened for ultraviolet absorbance and lenses having comparable UV absorbance at 390 nanometers for each example were tested in duplicate, unless indicated otherwise, for photochromic response in the Photochromic Temperature Dependence Test as described herein on a Bench for Measuring Photochromics (BMP) optical bench made by Essilor, France.

Prior to testing on the optical bench, the photochromic lenses were exposed to 365 nanometer ultraviolet light for about 10 minutes at a distance of about 14 centimeters to activate the photochromic compounds. The UVA (315 to 380 nm) irradiance at the sample was measured with a Licor Model Li-1800 spectroradiometer and found to be 22.2 watts per square meter. The lens samples were placed under a high intensity halogen lamp for about 10 minutes at a distance of about 36 centimeters to bleach (inactivate) the photochromic compounds. The illuminance at the sample was measured with the Licor spectroradiometer and found to be 21.9 Klux. The coated lenses were then kept covered for at least 1 hour prior to testing on an optical bench.

The BMP comprises a flat metal surface to which was fitted two 150 watt Xenon arc lamps positioned 90° apart (one lamp to provide UV/VIS light and one to provide the additional contribution of visible light). The somewhat collimated output beams from the xenon arc lamps were combined and directed toward the sample cell and toward irradiance detectors through a 50/50 beam splitter. Each lamp was filtered and shuttered individually and also shuttered after blending, prior to entering the sample cell. Each lamp was filtered with a Schott 3 mm KG-2 band-pass filter. The lamp for supplemental visible light was additionally filtered with a 400 nm cutoff filter.

The software supplied with the equipment, i.e., BMPSoft version 2.1e, was used to control timing, irradiance, air cell and sample temperature, shuttering, filter selection and response measurement. The software program provided for irradiance adjustments within established set limits through a photofeedback unit, that in turn, made slight adjustments to the lamp wattage and subsequent lamp output. If a selected irradiance could not be achieved within the limits of the photofeedback unit, the program indicated the need for a change in selection of neutral density filters for each light path. For single photochromic systems, response measurements for temperature dependence were collected at the visible lambda max of the compound. Photopic response measurements were collected when multiple photochromic compounds were used.

Set up of the BMP software required correlation factors between spectroradiometric measurements at the sample with a Licon Model 1800 spectroradiometer and a Graseby Model 5380 dual channel optometer fitted with a Model #268UVA UVA detector and a Model #268P visible light detector. The optometer detectors were mounted on an optical rail carrier and received one-half of the split and combined light beams from the xenon arc lamps. The BMP software used the correlation factors to set the operating irradiance on the optical bench. The lens sample cell was fitted with a quartz window and self-centering sample holder. The temperature in the sample cell was controlled at 10° C. or 35° C.) through the software with a modified Facis, Model FX-10, environment simulator.

The power output of the optical bench, e.g., the dosage of light that the sample lens would be exposed to, was adjusted to 5.0 or 6.7 Watts per square meter (W/m$^2$). Visible light output was always maintained at 50 kilolux. The lower power output was used to avoid off-scale or high variability readings due to detection limits or light scatter on the instrument. Off scale readings can also be avoided by using a lower concentration of photochromic compounds and/or ultraviolet light absorbers in the test sample or lens. The higher power output should not be exceeded in the photochromic Temperature Dependence Test described herein. A Zeiss spectrophotometer, Model MCS 501, with fiber optic cables for light delivery from a tungsten halogen lamp and through the sample was used for photochromic response and color measurements. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was ≈20° from perpendicular.

Response measurements, in terms of a change in optical density (ΔOD) from the unactivated or bleached state to the activated or darkened state were determined by establishing the initial unactivated transmittance, opening the shutter from the Xenon lamp(s) and measuring the transmittance through activation at selected intervals of time. Change in optical density is determined according to the formula: $\Delta OD = \log(\% Tb/\% Ta)$, where % Tb is the percent transmittance in the bleached state, % Ta is the percent transmittance in the activated state and the logarithm is to the base 10. Optical density measurement can be per specific wavelength, as indicated, or photopic.

The temperature dependence of the lenses was determined by measuring the change in optical density (ΔOD) from the bleached to the darkened state at two temperatures, 10 and 35° C. The measure used for determining the temperature dependence was the percent loss of lambda max response for single photochromics or percent loss of photopic response for multiple photochromic compounds between the two temperatures, % $\Delta OD Loss = 100*(1 - \Delta OD_{35}/\Delta OD_{10})$. The activation time at 35° C. was 15 minutes. The activation times for 10° C. were either 15 or 30 minutes, depending upon the photochromic system (very fast responding photochromic articles were activated for 15 minutes where slower responding photochromic articles were activated for 30 minutes). Different activation times were used to ensure complete activation, e.g., activation to a steady state optical density of the photochromic article while reducing the total measurement time. The % ΔOD loss results may vary by ±2.5.

An alternate method for determining the temperature dependence of the test samples was to determine the difference between the activated state luminous transmittance at saturation for the sample at 10° C. and the activated state luminous transmittance at saturation 35° C. using the transmittance data collected during the aforementioned response measurements. Articles of the present invention exhibit a difference of 20 percent or less and an unactivated percent luminous transmittance of greater than 70 percent.

Results for single samples of Examples 1-5 are in Table 1. Averaged results for duplicate samples: of Examples 6-11 are in Table 2; of Examples 12-17 are in Tables 3 and 3A; of Examples 18A1 and 18A2 are in Table 4; and of Examples 18B-22 are in Table 5. Results for single samples: of Examples 23-42 are in Table 6; and of Comparative Examples 1-11 are in Tables 7 and 7A.

TABLE 1

| Example No. | Wavelength Tested (nm) | ΔOD after 30 minutes @ 10° C. | ΔOD after 15 minutes @ 35° C. | % ΔOD Loss |
|---|---|---|---|---|
| 1 | 600 | 2.17 | 1.35 | 38 |
| 2 | 520 | 1.79 | 0.94 | 47 |
| 3 | 600 | 1.45 | 0.94 | 35 |
| 4 | 600 | 2.14 | 1.22 | 43 |
| 5 | 600 | 1.95 | 1.08 | 45 |

Table 1 shows that photochromic articles imbibed with the compositions of Examples 1-5 demonstrate an optical density response loss of from 35 to 47 percent in the Photochromic Temperature Dependence Test.

TABLE 2

| Example No. | Absorbance @ 390 nm | Wavelength tested (nm) | ΔOD after 30 minutes @ 10° C. | ΔOD after 15 minutes @ 35° C. | % Δ OD Loss |
|---|---|---|---|---|---|
| 6 | 0.53 | 590 | 0.92 | 0.63 | 32 |
| 7* | 0.53 | 570 | 0.43 | 0.34 | 21 |
| 8 | 0.50 | 540 | 1.25 | 0.74 | 41 |
| 9 | 0.26 | 590 | 0.37 | 0.25 | 32 |
| 10 | 0.48 | 590 | 0.67 | 0.47 | 30 |
| 11 | 0.42 | 590 | 0.56 | 0.37 | 34 |

*Single lens tested, all others tested in duplicate.

Table 2 shows that photochromic articles prepared using the compositions of Examples 6-11 demonstrate an optical density response loss of from 21 to 41 percent in the Photochromic Temperature Dependence Test.

TABLE 3

| Example No. | Absorbance @ 390 nm | ΔOD after 30 minutes @ 10° C. | ΔOD after 15 minutes @ 35° C. | % ΔOD Loss |
|---|---|---|---|---|
| 12 | 0.11 | 0.97 | 0.42 | 57 |
|  | 0.21 | 0.95 | 0.43 | 55 |
|  | 0.29 | 0.91 | 0.46 | 49 |
|  | 0.52 | 0.92 | 0.53 | 42 |
| 13 | 0.10 | 1.03 | 0.40 | 62 |
|  | 0.20 | 0.97 | 0.39 | 60 |
|  | 0.30 | 0.90 | 0.40 | 56 |
|  | 0.52 | 0.83 | 0.47 | 43 |
| 14 | 0.10 | 1.10 | 0.48 | 56 |
|  | 0.20 | 1.14 | 0.52 | 54 |
|  | 0.32 | 1.19 | 0.58 | 51 |
|  | 0.51 | 1.31 | 0.66 | 50 |
| 15 | 0.11 | 0.97 | 0.40 | 59 |
|  | 0.21 | 0.93 | 0.40 | 57 |
|  | 0.44 | 0.89 | 0.40 | 55 |
| 16 | 0.18 | 1.00 | 0.41 | 59 |
|  | 0.28 | 0.92 | 0.40 | 57 |
|  | 0.50 | 0.80 | 0.44 | 45 |
| 17 | 0.14 | 1.01 | 0.43 | 57 |
|  | 0.22 | 0.95 | 0.40 | 58 |
|  | 0.32 | 0.89 | 0.39 | 56 |
|  | 0.52 | 0.79 | 0.39 | 51 |

Table 3 shows that the optical density response loss for Examples 12-17 is improved or reduced by increasing the concentration, as measured by the absorbance, of the TDVA materials to a temperature dependent reducing amount in the coating applied to the surface of the test sample having the other photochromic compounds imbibed therein. Based on the results for Examples 15 and 17, a higher concentration of the TDVA material would be necessary to reduce the % ΔOD loss to 50 or less.

TABLE 3A

| Example No. | Absorbance @ 390 nm | Percent Transmittance after 30 minutes @ 10° C. | Percent Transmittance after 15 minutes @ 35° C. | Difference in Percent Transmittance between 10 and 35° C. |
|---|---|---|---|---|
| 12 | 0.11 | 9.0 | 34.0 | 25.0 |
|  | 0.21 | 10.0 | 32.0 | 22.0 |
|  | 0.29 | 11.0 | 30.0 | 19.0 |
|  | 0.52 | 10.0 | 25.0 | 15.0 |
| 13 | 0.10 | 8.0 | 35.0 | 27.0 |
|  | 0.20 | 9.2 | 35.2 | 26.0 |
|  | 0.30 | 10.6 | 34.6 | 24 |
|  | 0.52 | 12.2 | 27.8 | 15.6 |
| 14 | 0.10 | 7.0 | 29.3 | 22.3 |
|  | 0.20 | 6.4 | 26.5 | 20.1 |
|  | 0.32 | 5.6 | 22.9 | 17.3 |
|  | 0.51 | 4.2 | 19.2 | 15.0 |
| 15 | 0.11 | 9.2 | 34.8 | 25.6 |
|  | 0.21 | 10.2 | 34.7 | 24.5 |
|  | 0.44 | 11.2 | 34.4 | 23.2 |
| 16 | 0.18 | 8.9 | 33.9 | 25.0 |
|  | 0.28 | 10.5 | 34.6 | 24.1 |
|  | 0.50 | 13.0 | 31.5 | 18.5 |
| 17 | 0.14 | 8.6 | 32.7 | 24.1 |
|  | 0.22 | 9.8 | 34.6 | 24.8 |
|  | 0.32 | 11.2 | 35.4 | 24.2 |
|  | 0.52 | 14.2 | 35.0 | 20.8 |

Table 3A shows that the difference in the activated luminous percent transmittance measured at 10 and 35° for Examples 12-17 is improved or reduced by increasing the concentration, as measured by the absorbance, of the TDVA compounds to a temperature dependent reducing amount in the coating applied to the surface of the test sample having the other photochromic compounds imbibed therein. Based on the results for Examples 15 and 17, a higher concentration of the TDVA compound would be necessary to reduce the difference in the percent transmittance between 10 and 35° C. to 20 or less.

TABLE 4

| Example No. | Absorbance @ 390 nm | ΔOD After 30 minutes @ 10° C. | ΔOD After 15 minutes @ 35° C. | % ΔOD Loss |
|---|---|---|---|---|
| 18A1 | 0.58 | 0.61 | 0.51 | 16 |
| 18A1 | 0.80 | 0.81 | 0.62 | 23 |
| 18A1 | 1.26 | 1.13 | 0.79 | 30 |
| 18A2 | 1.90 | 1.22 | 0.86 | 30 |
| 18A2 | 2.50 | 1.29 | 0.88 | 32 |

In Table 4, the results show that as the concentration of PM-C in the coatings was decreased, as measured by absorbance at 390 nm, there was a decrease in the % ΔOD Loss measured at 590 nm, except when the absorbance of 1.90 was decreased to 1.26.

TABLE 5

| Example No. | ΔOD after 30 minutes @ 10° C. | ΔOD after 15 minutes @ 35° C. | % ΔOD Loss |
|---|---|---|---|
| 18 | 1.09 | 0.62 | 43 |
| 19A | 1.35 | 0.64 | 53 |
| 19B | 0.64 | 0.35 | 45 |
| 20 | 0.45 | 0.27 | 40 |
| 21 | 0.60 | 0.33 | 45 |
| 22 | 0.50 | 0.30 | 40 |

In Table 5, Example 18B having PM-U and PM-V in a polyurethane coating applied to a non-photochromic lens demonstrated a % ΔOD Loss of 43%. Example 19A represents the cast in place photochromic chip of PM-II which demonstrated a % ΔOD Los of 53%. Examples 19B and 20 show that by applying an acrylic coating containing PM-I to the chip of 19A the % ΔOD Loss decreases to 45% and 40% when 2% and 3%, respectively, of PM-I was used. Similar results were obtained in Examples 21 and 22 using PM-W.

TABLE 6

| Example No. | ΔOD after 30 minutes @ 10° C. | ΔOD after 15 minutes @ 35° C. | % ΔOD Loss |
|---|---|---|---|
| 23 | 1.16 | 0.63 | 46 |
| 24 | 1.15 | 0.63 | 45 |
| 25A | 1.16 | 0.72 | 38 |
| 25B | 0.95 | 0.62 | 35 |
| 25C | 1.00 | 0.64 | 36 |
| 26 | 1.21 | 0.69 | 43 |
| 27A | 0.68 | 0.47 | 31 |
| 27B | 1.01 | 0.66 | 35 |
| 27C | 1.17 | 0.75 | 36 |
| 27D | 1.35 | 0.83 | 39 |
| 28 | 1.06 | 0.63 | 41 |
| 29 | 1.14 | 0.63 | 45 |
| 30 | 1.15 | 0.65 | 43 |
| 31 | 1.39 | 0.76 | 45 |
| 32 | 1.48 | 0.80 | 46 |
| 33 | 1.70 | 1.04 | 39 |
| 34 | 1.21 | 0.75 | 38 |
| 35 | 1.27 | 0.72 | 43 |
| 36 | 1.25 | 0.71 | 43 |
| 37 | 1.45 | 0.89 | 39 |
| 38 | 1.06 | 0.63 | 41 |
| 39 | 1.59 | 0.93 | 42 |
| 40 | 1.38 | 0.76 | 45 |
| 41 | 1.07 | 0.74 | 31 |
| 42 | 0.96 | 0.62 | 35 |

In Table 6, Examples 23-40 demonstrate that articles having TDVA compounds imbibed therein can be produced with an optical density response loss of less than 50 percent in the Photochromic Temperature Dependence Test. Examples 41 and 42 demonstrate that further reductions in the optical density response loss are achievable using a TDVA compound in a coating applied to the surface of the imbibed test sample.

TABLE 7

| Comparative Example # | ΔOD after 30 minutes @ 10° C. | ΔOD after 15 minutes @ 35° C. | % OD Loss |
|---|---|---|---|
| 1 | 0.92 | 0.34 | 63 |
| 2 | 0.76 | 0.27 | 64 |
| 3 | 0.93 | 0.34 | 63 |
| 4 | 1.04 | 0.30 | 71 |
| 5 | 0.82 | 0.31 | 62 |
| 6 | 1.19 | 0.51 | 57 |
| 7 | 0.86 | 0.21 | 76 |
| 8 | 0.90 | 0.40 | 56 |
| 9 | 0.90 | 0.33 | 63 |
| 10 | 0.89 | 0.32 | 64 |
| 11 | 1.08 | 0.42 | 61 |

Table 7 shows that all of the commercially available plastic photochromic lenses evaluated, demonstrated an optical density response loss of 55 percent or higher in the Photochromic Temperature Dependence Test.

TABLE 7A

| Comparative Example # | Percent Transmittance after 30 minutes @ 10° C. | Percent Transmittance after 15 minutes @ 35° C. | Difference in Percent Transmittance between 10 and 35° C. |
|---|---|---|---|
| 1 | 11.1 | 41.5 | 30.4 |
| 2 | 15.5 | 47.7 | 32.2 |
| 3 | 10.8 | 41.3 | 30.5 |
| 4 | 8.0 | 45.0 | 37.0 |
| 5 | 13.0 | 42.0 | 29.0 |
| 6 | 6.0 | 28.0 | 22.0 |
| 7 | 12.0 | 51.0 | 39.0 |
| 8 | 12.0 | 35.0 | 23.0 |
| 9 | 11.0 | 40.0 | 29.0 |
| 10 | 10.0 | 41.0 | 31.0 |
| 11 | 7.0 | 33.0 | 26.0 |

Table 7A shows that all of the commercially available plastic photochromic lenses evaluated, demonstrated a difference in the activated luminous percent transmittance measured at 10 and 35°, of 22 percent or higher in the Photochromic Temperature Dependence Test.

The present invention has been described with reference to specific details of particular embodiments thereof. It is not intended that such details be regarded as limitations upon the scope of the invention except insofar as to the extent that they are included in the accompanying claims.

We claim:

1. A photochromic article demonstrating consistent photochromic response over a broad temperature range comprising:

a) a substrate;

b) a temperature dependent reducing amount of at least one organic photochromic material associated with said substrate, said photochromic material having a temperature dependent variable absorbance that changes from more absorbing to less absorbing of radiation in its activating spectral absorbance as the temperature increases from 10° C. to 35° C.; and c) at least one other organic photochromic material (c) associated with said substrate that is different from photochromic material (b); said photochromic material (b) being used in a coating or film on the surface of the substrate and interposed between photochromic material (c) and a source of activating radiation, wherein the substituent groups of photochromic material (b) are chosen such that said photochromic article exhibits an activated optical density response loss of 50 percent or less as measured in the Photochromic Temperature Dependence Test, said photochromic material (b) being chosen from:

(1) a naphthopyran compound represented by the following graphic formula I:

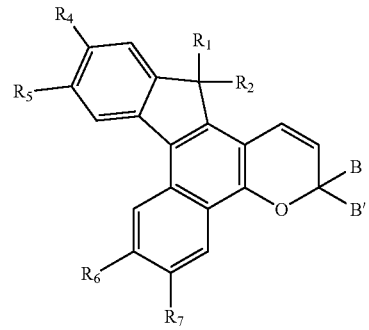

wherein (a) $R_1$ and $R_2$ are each independently chosen from:

(i) hydrogen, hydroxy, $C_1$-$C_6$ alkyl, $C_1$-$C_8$ haloalkyl, $C_3$-$C_7$ cycloalkyl, or the group, —C(O)W, wherein W is hydroxy, $C_1$-$C_6$ alkyl, $C_1$-$C_6$ alkoxy, di($C_1$-$C_6$) alkylamino, morpholino or piperidino;

(ii) the group, —$OR_8$ wherein $R_8$ is $C_1$-$C_6$ alkyl, $C_1$-$C_6$ acyl, $C_1$-$C_8$ haloalkyl, phenyl($C_1$-$C_3$)alkyl or the group —CH($R_9$)Q, wherein $R_9$ is hydrogen or $C_1$-$C_3$ alkyl and Q is —$COOR_{10}$, and $R_{10}$ is hydrogen or $C_1$-$C_3$ alkyl;

(iii) the group —CH($R_{12}$)G, wherein $R_{12}$ is hydrogen or $C_1$-$C_6$ alkyl, and G is —$COOR_{11}$, wherein $R_{11}$ is hydrogen or $C_1$-$C_6$ alkyl; or (iv) the group T represented by the formula:

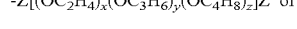

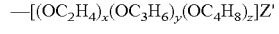

wherein -Z is —C(O)— or —$CH_2$—, Z' is $C_1$-$C_3$ alkoxy or a polymerizable group, x, y and z are each a number between 0 and 50, and the sum of x, y and z is between 2 and 50; or (v) $R_1$ and $R_2$ together form $R_3$ chosen from a substituted or unsubstituted spiro-carbocyclic ring containing 5 to 6 carbon atoms, said spiro-carbocyclic ring being annellated with 0, 1 or 2 benzene rings, said substituents being hydrogen or $C_1$-$C_6$ alkyl;

(b) $R_4$ and $R_7$ are each independently chosen from hydrogen, provided that both are not hydrogen, the group T, —$OR_7$, wherein $R_7$ is chosen from $C_1$-$C_6$ alkyl, phenyl ($C_1$-$C_6$)alkyl or $C_1$-$C_6$ alkoxy($C_1$-$C_6$)alkyl or $R_4$ and $R_7$ are each independently a nitrogen-containing group chosen from:

(i) —N($R_{15}$)$R_{16}$ wherein $R_{15}$ and $R_{16}$ are each independently chosen from hydrogen, $C_1$-$C_8$ alkyl or $R_{15}$ and $R_{16}$ come together with the nitrogen atom to form a $C_3$-$C_{20}$ hetero-bicycloalkyl ring or a $C_4$-$C_{20}$ hetero-tricycloalkyl ring;

(ii) a nitrogen containing ring represented by the following graphic formula:

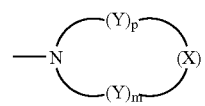

wherein each Y is —$CH_2$—, and X is chosen from —Y—, —O—, —S—, —S(O)—, —$S(O_2)$—, —NH—, —N($R_{17}$)— or —N(aryl)-, wherein $R_{17}$ is $C_1$-$C_6$ alkyl, said aryl is phenyl or naphthyl, m is the integer 1, 2 or 3, and p is the integer 0, 1, 2, or 3 and when p is O, X is Y; or (iii) a group represented by one of the following graphic formulae:

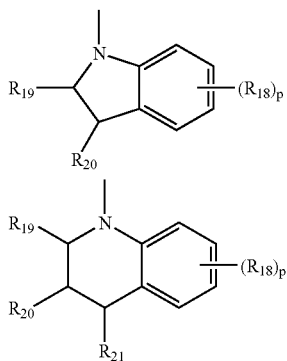

wherein $R_{19}$, $R_{20}$ and $R_{21}$ are each independently chosen for each occurrence in each formula from hydrogen or $C_1$-$C_6$ alkyl, or the groups $R_{19}$ and $R_{20}$ together form a ring of 5 to 8 carbon atoms and each $R_{18}$ is $C_1$-$C_6$ alkyl and p being the integer 0, 1, 2 or 3;

(c) $R_5$ and $R_6$ are each independently chosen from hydrogen, $C_1$-$C_6$ alkyl, $C_1$-$C_6$ haloalkyl, the group T, —$OR_{7'}$, described hereinbefore in (b) or nitrogen-containing group (b) (i), (ii) or (iii); and (d) B and B' are each independently chosen from:
(i) mono-T-substituted phenyl;
(ii) the unsubstituted, mono-, di-, or tri-substituted aryl groups, phenyl or naphthyl, each of said aryl substituents being chosen from hydroxy, aryl, morpholino, $C_1$-$C_8$ alkoxy ($C_1$-$C_8$)alkoxy, aryl($C_1$-$C_6$) alkyl, aryloxy, $C_1$-$C_6$ alkyl, $C_1C_6$ haloalkyl, $C_1$-$C_6$ alkoxy, acryloxy, methacryloxy, halogen, —$CF_3$, —CN or —$COOR_{11}$; wherein $R_{11}$ is the same as described hereinbefore; or
(iii) mono-substituted phenyl, said substituent located at the para position being —($CH_2$)$_t$— or —O—($CH_2$)$_t$—, wherein t is the integer 1, 2, 3, 4, 5 or 6, said substituent being connected to an aryl group on another photochromic material;

(2) a naphthopyran compound represented by the following graphic formula II:

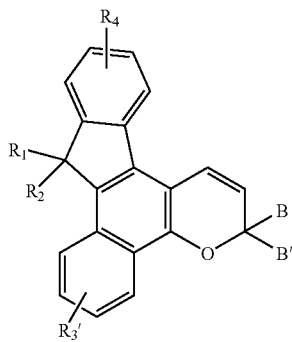

wherein;
$R_1$, $R_2$, $R_4$, B and B' are the same groups described hereinbefore in (1) (a), (b) and (d); $R_3$ is —$OR_{8'}$, wherein $R_{8'}$ is $C_1$-$C_6$ alkyl or phenyl($C_1$-$C_3$)alkyl; or $R_{3'}$ is chosen from hydrogen, $C_1$-$C_6$ alkyl or $C_1$-$C_6$ haloalkyl;

(3) a naphthopyran compound represented by graphic formula III:

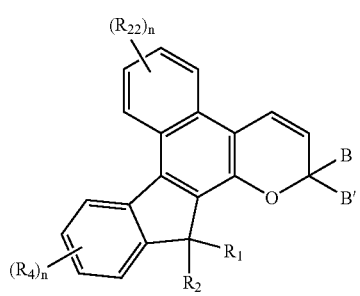

wherein;
$R_1$, $R_2$, $R_4$, B and B' are the same groups described hereinbefore in (1) (a), (b) and (d); each $R_{22}$ is independently chosen from hydrogen, $C_1$-$C_6$ alkyl, $C_3$-$C_7$ cycloalkyl, $C_1$-$C_6$ haloalkyl or —$OR_{8'}$, which was described hereinbefore in (2), and n is the integer 0, 1, 2, or 3;

(4) a naphthopyran compound represented by the following graphic formula IV:

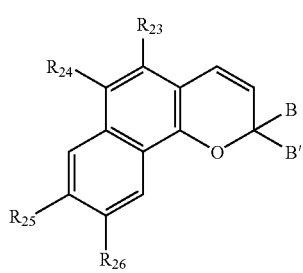

wherein;
(a) $R_{23}$ is —C(O)L, or —C($R_{27}$) ($R_{28}$)$OR_{11}$, wherein L is —$OR_{11}$, —N($R_{15}$)$R_{16}$, (2-(2-hydroxyethoxy)ethoxy) or an unsubstituted, mono-substituted or di-substituted heterocyclic ring chosen from 1-indolinyl, morpholino, piperidino, 1-pyrrolidyl or 1-piperazinyl, said heterocyclic ring substituents being $C_1$-$C_6$ alkyl; $R_{11}$, $R_{15}$, and $R_{16}$ are the same as described hereinbefore in (1) (a) (iii) and (b) (i); $R_{27}$ and $R_{28}$ are each independently chosen from $C_1$-$C_6$ alkyl, $C_3$-$C_7$ cycloalkyl, $C_1$-$C_6$ haloalkyl or phenyl;
(b) $R_{24}$ is hydrogen, $C_1$-$C_6$ alkyl, $C_3C_7$ cycloalkyl, mono- or di- ($C_1$-$C_6$)alkylaryl, mono- or di-($C_1$-$C_6$) alkoxyaryl, $C_1$-$C_6$ haloalkyl, phenyl or naphthyl;
(c) $R_{25}$ and $R_{26}$ are each independently chosen from hydrogen, $C_1$-$C_6$ alkyl, $C_3$-$C_7$ cycloalkyl, $C_1$-$C_6$ haloalkyl, the group T, described hereinbefore in (1) (a) (iv) —$OR_{8'}$, described hereinbefore in (2) or said nitrogen-containing group (1) (b) (i), (ii), or (iii) described hereinbefore or $R_{25}$ and $R_{26}$ together form one of the following graphic formulae:

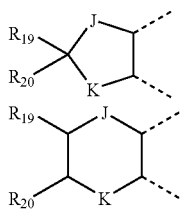

wherein J and K are each independently chosen for each occurrence in each formula from oxygen or the group —N($R_{15}$)—, $R_{15}$, $R_{19}$ and $R_{20}$, are the same groups described hereinbefore in (1) (b) (i) and (iii); and (d) B and B' are the same roups described hereinbefore in (1) (d);

(5) a naphthopyran represented by the following graphic formula V:

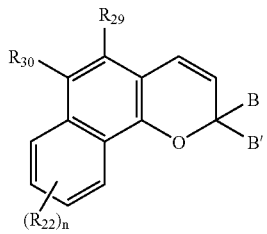

wherein;

(a) $R_{22}$ and n are the same as described hereinbefore in (3); $R_{29}$ is hydroxy, $C_1$-$C_6$ alkyl, $C_3$-$C_7$ cycloalkyl, $C_1$-$C_6$ haloalkyl, aryl, mono($C_1$-$C_6$)alkoxyaryl, di($C_1$-$C_6$)alkoxyaryl, mono($C_1$-$C_5$)alkylaryl, di($C_1$-$C_6$)alkylaryl, haloaryl, di($C_1$-$C_6$)alkylaminoaryl, the group T described hereinbefore in (1) (a) (iv), —$OR_8$, described hereinbefore in (2), or said nitrogen-containing group (1) (b) (i), (ii) or (iii) described hereinbefore;

(b) $R_{30}$ is hydrogen or $R_{23}$ described hereinbefore in (4) (a); and (c) B and B' are the same groups described hereinbefore in (1) (d);

(6) a naphthopyran compound represented by the following graphic formula VI:

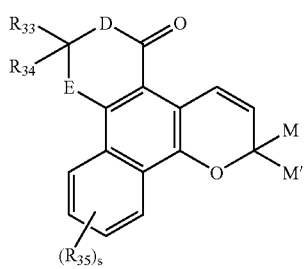

wherein (a) $R_{31}$ is hydrogen or $R_{29}$ described hereinbefore in (5) (a);

(b) $R_{32}$ is $C_1$-$C_6$ alkyl, $C_1$-$C_6$ alkoxy or $C_1$-$C_6$ haloalkyl, n is the same as described hereinbefore in (3); and (c) B and B' are the same groups described hereinbefore in (1) (d); and (7) a naphthopyran represented by the following graphic formula VII:

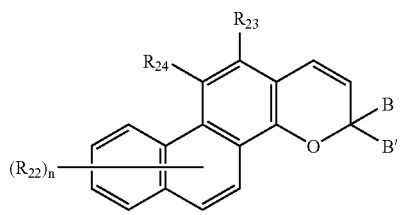

wherein:

each $R_{22}$ and n are the same as described hereinbefore in (3); $R_{23}$ and $R_{24}$ are the same as described hereinbefore in (4) (a) and (b); B and B' are the same as described hereinbefore in (1) (d);

(8) a naphthopyran represented by the following graphic formula VIII:

wherein, (a) $R_{33}$ and $R_{34}$ together form an oxo group or $R_{33}$ is hydrogen and $R_{34}$ is hydrogen, $C_1$-$C_6$ alkyl, $C_3$-$C_7$ cycloalkyl, allyl, phenyl, mono- or di-substituted phenyl, benzyl, mono-substituted benzyl, linear or branched $C_3$-$C_{12}$ alkenyl, $C_1$-$C_6$ alkoxy carbonyl ($C_1$-$C_6$) alkyl, methacryloxy($C_1$-$C_6$)alkyl, acryloxy($C_1$$C_6$) alkyl, $C_1$-$C_4$ acyloxy($C_1$-$C_6$)alkyl, each of said phenyl or benzyl substituents being $C_1$-$C_6$ alkyl, $C_1$-$C_6$ alkoxy, morpholino, di($C_1$-$C_6$)alkylamino, chioro or fluoro;

(b) each $R_{35}$ is independently chosen for each occurrence from $C_1$-$C_6$ alkyl, $C_1$-$C_6$ alkoxy, chloro, fluoro, phenyl, $C_3$-$C_7$ cycloalkyl, di($C_1$-$C_6$)alkylamino, morpholino, thiomorpholino, piperidino, pyridyl, N—($C_1$-$C_6$)alkyl piperizino or N-phenyl piperizino, and s is the integer 0, 1 or 2;

(c) D is oxygen or —N($R_{36}$)—, wherein $R_{36}$ is hydrogen, $C_1$-$C_6$ alkyl, $C_3$-$C_7$ cycloalkyl, $C_1$-$C_5$ acyl or phenyl;

(d) E is oxygen, —N($R_{36}$)— or —C($R_{37}$) ($R_{38}$)—, wherein $R_{37}$ and $R_{38}$ are each independently chosen from hydrogen, $C_1$-$C_6$ alkyl or $C_3$-$C_7$ cycloalkyl, with the proviso that when E is —C($R_{37}$) ($R_{38}$)—, D is oxygen; and (e) M and M' are each chosen from the urisubstituted, mono—, di- or tri-substituted aryl group, phenyl or naphthyl; each of said aryl substituents being chosen from hydroxy, phenyl, morpholino, naphthylaryl($C_1$-$C_6$)alkyl, aryloxy, $C_1$-$C_6$ alkyl, $C_1$-$C_6$ chloroalkyl, $C_1$-$C_6$ fluoroalkyl, $C_1$-$C_6$ alkoxy, acryloxy, methacryloxy, bromo, chloro or fluoro; or (9) mixtures thereof.

2. The photochromic article of claim 1 wherein the photochromic article is adapted to exhibit an activated optical density response loss of 35 percent or less as measured in the Photochromic Temperature Dependence Test.

3. The photochromic article of claim 2 wherein the photochromic article is adapted to exhibit an activated optical density response loss of 20 percent or less as measured in the Photochromic Temperature Dependence Test.

4. The photochromic article of claim 1 wherein photochromic material (b) is chosen from:

(1) the naphthopyran represented by graphic I wherein, (a) $R_1$ and $R_2$ are each independently chosen from:

(i) hydrogen, hydroxy, $C_1$-$C_6$ alkyl, $C_1$-$C_6$ haloalkyl, or $C_3$-$C_7$ cycloalkyl, (ii) the group, —$OR_8$ wherein $R_8$ is $C_1$-$C_6$ alkyl, $C_1$-$C_6$ acyl, or $R_8$ is the group —$CH(R_9)Q$, wherein $R_9$ is hydrogen or $C_1$-$C_3$ alkyl and Q is —$COOR_{10}$, and $R_{10}$ is $C_1$-$C_3$ alkyl;

(iii) the group —$CH(R_{12})G$, wherein $R_{12}$ is hydrogen or $C_1$-$C_6$ alkyl, and G is —$COOR_{11}$, wherein $R_{11}$ is $C_1$-$C_6$ alkyl; or (iv) the group T represented by the formula:

-Z[(OC$_2$H$_4$)$_x$(OC$_3$H$_6$)$_y$(OC$_4$H$_8$)$_z$]Z' or

—[(OC$_2$H$_4$)$_x$(OC$_3$H$_6$)$_y$(OC$_4$H$_8$)$_z$]Z' wherein -Z is —$CH_2$—, Z' is $C_1$-$C_3$ alkoxy or a polymerizable group, x, y and z are each a number between 0 and 50, and the sum of x, y and z is between 2 and 50; or (viii) $R_1$ and $R_2$ together form $R_3$ chosen from a substituted or unsubstituted spiro-carbocyclic ring containing 5 to 6 carbon atoms, said spiro-carbocyclic ring being annellated with 0, 1 or 2 benzene rings, said substituents being hydrogen or $C_2$-$C_6$ alkyl;

(b) $R_4$ and $R_7$ are each independently chosen from hydrogen and, the group —$OR_{7'}$ wherein $_{7'}$ is chosen from $C_1$-$C_3$ alkyl, phenyl($C_1$-$C_2$)alkyl, or $C_1$-$C_3$ alkoxy($C_1$-$C_3$)alkyl, or $R_4$ and $R_7$ are each independently a nitrogen-containing group chosen from:

(i) —$N(R_{15})R_{16}$ wherein $R_{15}$ and $R_{16}$ are each independently chosen from $C_1$-$C_8$ alkyl, (ii) a nitrogen containing ring represented by the following graphic formula:

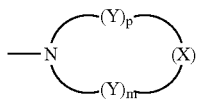

wherein each Y is independently chosen for each occurrence from —$CH_2$—, and X is chosen from —Y—, O—, —S—, —NH—, —$N(R_{17})$— or —N(aryl)-, wherein $R_{17}$ is $C_1$-$C_6$ alkyl, said aryl group being phenyl or naphthyl, m is the integer 1, 2 or 3, and p is the integer 0, 1, 2, or 3 and when p is O, X is Y; or (iii) a group represented by the following graphic formulae:

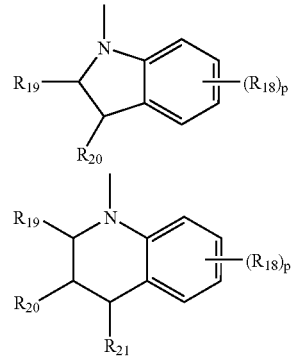

wherein $R_{19}$, $R_{20}$ and $R_{21}$ are each independently chosen for each occurrence in each formula from hydrogen or $C_1$-$C_6$ alkyl, each $R_{18}$ is independently chosen for each occurrence from $C_1$-$C_3$ alkyl, and p is the same as described hereinbefore in (ii), provided that both $R_4$ and $R_7$ are not hydrogen;

(c) $R_5$ and $R_6$ are each independently chosen from hydrogen, $C_1$-$C_6$ alkyl, the group T, described hereinbefore in (a) (iv), —$OR_{7'}$, described hereinbefore in (b) or nitrogen-containing group (b) (i) (ii) or (iii); and (d) B and B' are each chosen from:

(i) mono-T-substituted phenyl (ii) the unsubstituted, mono-, or di-substituted aryl groups, phenyl or naphthyl, each of said aryl substituents being chosen from aryl, morpholino $C_1$-$C_6$ alkyl, $C_1$-$C_6$ haloalkyl, $C_1$-$C_6$ alkoxy, acryloxy, methacryloxy, halogen, —$CF_3$,—CM or —$COOR_{11}$;

(iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group on another photochromic material;

(2) the naphthopyran represented by graphic formula II wherein: $R_1$, $R_2$, $R_4$, B and B' are the same groups described hereinbefore in (1) (a) (b) and (d); $R_{3'}$ is —$OR_{8'}$, wherein $R_{8'}$ is $C_1$-$C_3$ alkyl, or phenyl($C_1$-$C_2$) alkyl, or $R_{3'}$ is hydrogen, $C_1$-$C_6$ alkyl, or $C_1$-$C_6$ haloalkyl;

(3) the naphthopyran represented by graphic formula III wherein: $R_1$, $R_2$, $R_4$, B and B' are the same groups described hereinbefore in (i) (a) (b) and (d); each $R_{22}$ is independently chosen for each occurrence from hydrogen, $C_1$-$C_6$ alkyl, $C_3$-$C_7$ cycloalkyl, or —$OR_{8'}$, which was described hereinbefore, and n is the integer 0, 1, 2, or 3;

(4) the naphthopyran represented by graphic formula TV wherein:

(a) $R_{23}$ is —C(O)L, or —(CR$_{27}$)(R$_{28}$)OR$_{11}$, wherein L is —$OR_{11}$, —$N(R_{15})R_{16}$ or (2-(2-hydroxyethoxy)ethoxy); $R_{11}$, $R_{15}$, and $R_{16}$ are the same as described hereinbefore in (1) (a) (iii) and (b) (i); $R_{27}$ and $R_{28}$ are each independently chosen from $C_1$-$C_6$ alkyl, $C_3$-$C_7$ cycloalkyl, or;

(b) $R_{24}$ is hydrogen, $C_1$-$C_6$ alkyl, $C_3$-$C_7$ cycloalkyl, $C_1$-$C_6$ haloalkyl or phenyl;

(c) $R_{25}$ and $R_{26}$ are each independently chosen from hydrogen, $C_1$-$C_6$ alkyl, $C_1$-$C_6$ haloalkyl, the group —OR$_{8'}$ described hereinbefore in (2) or nitrogen-containing group (1) (b) (i), (ii) or (iii) described hereinbefore;

(d) B and B' are the same groups described hereinbefore in (1) (d);

(5) the naphthopyran represented by graphic formula V wherein:

(a) R$_{22}$ and n are the same as described hereinbefore in (3), R$_{29}$ is hydroxy, C$_1$-C$_6$ alkyl, C$_3$-C$_7$ cycloalkyl, C$_1$-C$_6$ haloalkyl, aryl, mono(C$_1$-C$_6$)alkoxyaryl, di(C$_1$-C$_6$)alkoxyaryl, haloaryl, di(C$_1$-C$_6$)alkylaminoaryl, the group T, described hereinbefore in (1) (a) (iv) —OR$_{8'}$, described hereinbefore in (2) or nitrogen-containing group (1) (b) (i), (ii) or (iii) described hereinbefore:

(b) R$_{30}$ is hydrogen or R$_{23}$ described hereinbefore in (4) (a); and (c) B and B' are the same groups described hereinbefore in (1) (d);

(6) the naphthopyran represented by graphic formula VI wherein:

(a) R$_{31}$ is hydrogen or R$_{29}$ described hereinbefore in (5) (a);

(b) R$_{32}$ is hydrogen; and (c) B and B' are the same groups described hereinbefore in (1) (d);

(7) the naphthopyran represented by graphic formula VII wherein: each a$_{22}$ and n are the same as described hereinbefore in (3); R$_{23}$ and R$_{24}$ are the same as described hereinbefore in (4) (a) and (b); B, and B' are the same as described hereinbefore in (1) (d);

(8) the naphthopyran represented by graphic formula VIII wherein:

(a) R$_{33}$ is hydrogen and R$_{34}$ is chosen from hydrogen, C$_1$-C$_5$ alkyl, C$_3$-C$_6$ cycloalkyl, phenyl, mono- or di-substituted phenyl, benzyl or mono-substituted benzyl, each of said phenyl and benzyl group substituents being C$_1$-C$_4$ alkyl or C$_1$-C$_4$ alkoxy;

(b) R$_{35}$ is C$_1$-C$_4$ alkyl, C$_1$-C$_4$ alkoxy, fluoro, or phenyl, and s is the integer 0, 1, or 2;

(c) D is oxygen or —N(R$_{36}$)—, wherein H$_{36}$ is hydrogen, or C$_1$-C$_3$ alkyl;

(d) E is oxygen, —NH— or —CH$_2$—; and (e) M and M' are each independently chosen from:

(i) phenyl, mono-substituted phenyl or di-substituted phenyl, each of said phenyl substituents being aryloxy, morpholino, C$_1$-C$_3$ alkyl, C$_1$-C$_3$ chloroalkyl, C$_1$-C$_3$ fluoroalkyl, C$_1$-C$_3$ alkoxy, fluoro or chioro; or (9) mixtures thereof.

5. The photochromic article of claim 1 wherein photochromic material (b) is chosen from:

(1) a photochromic material represented by graphic formula I chosen from:

(a) 3-(4-methoxyphenyl)-3-phenyl-6,7,10,11-tetramethoxy-13-ethyl-13-hydroxyl3H-3H-indeno[2,'3'3,4]naphtho[1,2-b]pyran;

(b) 3,3-di(4-methoxyphenyl)-6,11-dimethoxy-13-butyl-13-ethoxy-13H-31H-indeno[2,'3,'3,4]naphtho[1,2-b]pyran;

(c) 3-(4-methoxyphenyl)-3-phenyl-6,11-dimethoxy-13-methyl-13-(2-(2hydroxyethoxy)ethoxy)-13H-3H-indeno[2,'3,'3,4]naphtho[1,2-b]pyran;

(d) 3,3-di(4-methoxyphenyl)-11-morpholino-13,13-dimethyl-13H-3H-indeno[2,'3,'3,4)naphtho[1,2-b]pyran;

(e) 3-(4-morpholinophenyl)-3-phenyl-11-morpholino -13,13-dimethyl-13H-3H-indeno[2,'3,'3,4]naphtho[1,2-b]pyran;

(f) 3-(4-methoxyphenyl)-3-phenyl-10,11-dimethoxy -13,13-dimethyl-13H-3H-indeno[2,'3,'3,4]naphtho[1,2-b]pyran;

(g) 3-(4-methoxyphenyl)-3-phenyl-13,13-dimethyl-13H3H-indeno[2,'3,'3,4]naphtho[1,2-b]pyran;

(h) 3,3-di(4-methoxyethoxyphenyl)-11-morpholino -13,13-dimethyl-13H-3H-indeno[2,'3,'3,4]naphtho[1,2-b]pyran;

(i) 3,3-diphenyl-6,11-dimethoxy-13-acetoxy-13H-3H-indeno[2,'3,'3,4]naphtho[1,2-b]pyran;

(j) 3-(4-methoxyphenyl)-3-phenyl-6,10,11-trimethoxy-13-methyl-13-hydroxy-13H-3H-indeno[2,'3,'3,4]naphtho[1,2-b]pyran;

(k) 3-(4-morpholinophenyl)-3-(4-methoxyphenyl)11-morpholino-13,13 -dimethyl-13H-3H-indeno[2,'3,'3,4]naphtho[1,2-b]pyran;

(l) 3-(3,4-dimethoxyphenyl)-3-(4-methoxyphenyl)-11-morpholino-13,13-dimethyl-13H-3H-indeno[2,'3,'3,4]naphtho[1,2-b]pyran;

(m) 3-(4-methoxyphenyl)-3-phenyl-6,7,10,11-tetramethoxy-13-13-dimethyl-13H-3H-indeno[2,'3,'3,4]naphtho[1,2-b]pyran;

(n) 3-(4-methoxyphenyl)-3-phenyl-6,7,10,11-tetramethoxy-13-trifluromethyl-13-hydroxy-13H-3H-indeno[2,'3,'3,4]naphtho[1,2b]pyran;

(o) 3(4methoxyphenyl)-3-phenyl-6,10,11-trimethoxy-13-butyl-13-hydroxy-13H-3H-indeno[2,'3,'3,4]naphtho[1,2-b]pyran;

(p) 3-(4-morpholinophenyl)-3-phenyl-6,11-dimethoxy-13-methoxy-13-methyl-13H-3H-indeno(2,'3,'3,4]naphtho[1,2-b]pyran;

(q) 3,3-di(4-dimethoxyphenyl)6,7,10,11-tetramethoxy-13,13-dimethyl-13H-3H-indeno[2,'3,'3,4]naphtho[1,2-b]pyran;

(r) 3,3-diphenyl-13,13-dimethyl-13H-3H-indeno[2,'3,'3,4]naphtho[1,2-b]pyran; or (s) 3-(4-methoxyphenyl)-3-phenyl-G,11-dimethoxy-13-ethyl-13-hydroxy-13H-3H-indeno[2,'3,'3,4]naphtho[1,2-b]pyran;

(2) a photochromic material represented by graphic formula II chosen from:

(a) 3,3diphenyl-9-methyl-11-methoxy-311-9H-indeno[3',2':3,4]naphtho[1,2-b]pyran;

(b) 3,3-diphenyl-9,9-dimethyl-11,6-dimethoxy-3H-9H-indeno[3',2':3,4]naphtho[1,2-b]pyran;

(c) 3-(4-methoxyphenyl)-3-phenyl-9,9-dimethyl-11,6-dimethoxy-3H-9H-indeno[3',2':3,4]naphtho[1,2-b]pyran;

(d) 3-(3-trifluoromethylphenyl)-3-phenyl-9-methyl-9-phenyl-11-dimethoxy-3H-9H-indeno[3',2':3,4]naphtho[1,2-b]pyran; or (e) 3,3-diphenyl-9-phenyl-3H-9H-indeno[3',2':3,4]naphtho [1,2-b]pyran;

(3) a photochromic material represented by graphic formula III chosen from:

(a) 2,2-diphenyl-6,7-dimethoxy-2H-13H-indeno[1',2':4,3]naphtho[2,1-b]pyran;

(b) 2,2-diphenyl-6,7-dimethoxy-13-methyl-2H-3H-indeno [1',2':4,3]naphtho[2,1-b]pyran;

(c) 2,2-diphenyl-6-methoxy-13,13-dimethyl-2H-13H-indeno [1',2':4,3]naphtho[2,1-b]pyran;

(d) 2-(3-trifluoromethylphenyl)-2-phenyl-6-methoxy-13,13-dimethyl-2H-13H-indeno[1',2':4,3]naphtho[2,1-b]pyran;

(e) 2-(3-methoxyphenyl)-2-phenyl-6,7,11-trimethoxy-13-methyl-13-hydroxy-2H-13H-indeno[1',2':4,3]naphtho[2,1-b]pyran;
(f) 2-(3-methoxyphenyl)-2-phenyl-6,7-dimethoxy-13,13-dimethyl-2H-13H-indeno[1',2':4,3]naphtho[2,1-b]pyran; or
(g) 2-(3-methoxyphenyl)-2-phenyl-6,7-dimethoxy-13-methyl-13-hydroxy-2H-13H-indeno[1',2':4,3]naphtho[2,1-b]pyran;
(4) a photochromic material represented by graphic formula IV chosen from:
(a) 2,2-diphenyl-5-(2-hydroxy)propyl)-8-methoxy-2H-naphtho[1,2-b]pyran;
(b) 2,2-phenyl-5-(2-(hydroxy)propyl)-6-phenyl-8,9-dimethoxy-2H-naphtho[1,2-b]pyran;
(c) 2,2-phenyl-5-carbomethoxy-6-phenyl-8,9-dimethoxy-2H-naphtho[1,2-b]pyran;
(d) 2-(3-trifluoromethylphenyl)-2-phenyl-5-carbomethoxy-6-methyl-9-methoxy-2H-naphtho[1,2-b]pyran;
(h) 2,2-di(3-trifluoromethylphenyl)-5-carbomethoxy-6-methyl-9-methoxy-2H-naphtho[1,2-b]pyran;
(i) 2,2-diphenyl-5-carbomethoxy-6-(4-methoxyphenyl)-9-methoxy-2H-naphtho[1,2-b]pyran;
(j) 2,2-di(4-fluorophenyl)-5-carbomethoxy-6-methyl-9-methoxy-2H-naphtho[1,2-b]pyran;
(k) 2,2-di(3-trifluoromethylphenyl)-5-(2-(hydroxy)propyl)-6-methyl-9-methoxy-2H-naphtho[1,2-b]pyran;
(l) 2,2-diphenyl-5-carbomethoxy-6-phenyl-9-methoxy-2H-naphtho[1,2-b]pyran; or
(m) 2,2-diphenyl-5-(2-(2-hydroxyethoxy)ethoxy) carbonyl-6-(4-methoxyphenyl)-9-methoxy-2H-naphtho[1,2-b]pyran;
(5) a photochromic material represented by graphic formula V chosen from:
(a) 2,2-phenyl-5-methyl-2H-naphtho[1,2-b]pyran;
(b) 2,2-phenyl-5-phenyl-2H-naphtho[1,2-b]pyran;
(c) 2,2-phenyl-6-carbomethoxy-5-(4-morpholinophenyl)-2H-naphtho[1,2-b]pyran;
(d) 2,2-phenyl-6-carbomethoxy-5-hydroxy-2H-naphtho[1,2-b]pyran;
(e) 2,2-phenyl-6-carbomethoxy-5-methoxy-2H-naphtho[1,2-]pyran;
(f) 2,2-phenyl-6-carbomethoxy-5-8-dimethoxy-2H-naphtho[1,2-b]pyran;
(g) 2-phenyl-2-(3-trifluorophenyl)-6-phenyl-5-hydroxy-2H-naphtho[1,2-b]pyran;
(h) 2-phenyl-2-(4-methoxyphenyl)-6-(2-(hydroxy)propyl)-5-morpholino-2H-naphtho[1,2b]pyran;
(j) morpholinophenyl)-2H-naphtho[1,2-b]pyran;
(6) a photochromic material represented by graphic formula VI chosen from:
(a) 3-phenyl-3-(2-fluorophenyl)-3H-naphtho[2,1-b]pyran;
(b) 3-phenyl-3-(2-fluorophenyl)-6-acetoxy-3H-naphtho[2,1-b]pyran;
(c) 3,3-diphenyl-6-morpholino-3H-naphtho[2,1-b]pyran;
(d) 3-phenyl-3-(2-fluorophenyl)-5-hydroxymethyl-3H-naphtho[2,1-b]pyran;
(e) 3-phenyl-3-(3-trifluoromethylphenyl)-3H-naphtho[2,1-b]pyran; or
(f) 3-(4-methylphenyl)-3-(2-fluorophenyl)-3H-naphtho[2,1-b]pyran;
(7) a photochromic material represented by graphic formula VII chosen from:
(a) 3,3-diphenyl-12-methoxycarbonyl-11-methyl-6-methoxy-3H-phenanthro[1,2-b]pyran;

(8) a photochromic material represented by graphic formula VIII chosen from:
(a) 2,2,7,7-tetraphenyl-4-oxo-2,3,4,7-tetrahydro-1H-pyrimidino[5'4':3,4]naphtho[1,2-b]pyran;
(b) 7,7-diphenyl-2-pentyl-4-oxo-4H-7H-[1,3]dioxino[5',4':3,4]naphtho[1,2-b]pyran;
(c) (2-fluorophenyl)-3-(3-methyl-4-methoxyphenyl)-2-pentyl-4-oxo-4H-7H-[1,3]dioxino[5',4':3,4]-naphtho[1,2-b]pyran; or
(d) 7-(4-morpholino-2-fluorophenyl)-7-(3,4-dimethoxyphenyl)-2-pentyl-4-oxo-4H-7H-[1,3]dioxino[5',4':3,4]naphtho[1,2-b]pyran; or
(9) mixtures thereof.
6. The photochromic article of claim 5 wherein photochromic material (b) is chosen from:
(a) 3-(4-methoxyphenyl)-3-phenyl-6,7,10,11-tetramethaxy-13-ethyl-13-hydroxy-13H-3H-indeno[2,'3,'3,4]naphtho[1,2-b]pyran;
(b) 3,3-di(4-methoxyphenyl)-6,11-dimethoxy-13-butyl-13-ethoxy-13H-3H-indeno[2,'3,'3,4]naphtho[1,2-b]pyran;
(c) 3-(4-methoxyphenyl)-3-phenyl-6,11-dimethoxy-13-methyl-13-(2-(2-hydroxyethoxy)ethoxy)-13H-3H-indeno[2,'3,'3,4]naphtho[1,2-b]pyran;
(d) 3,3-di(4-methoxyphenyl)-11-morpholino-13,13-dimethyl-13H-3H-indeno[2,'3,'3,4]naphtho[1,2-b]pyran;
(e) 3-(4-morpholinophenyl)-3-phenyl-11-morpholino-13,13-dimethyl-13H-3H-indeno[2,'3,'3,4]naphtho[1,2-b]pyran;
(f) 3-(4-methoxyphenyl)-3-phenyl-10,11-dimethoxy-13,13dimethyl-13H-3H-indeno[2,'3,'3,4]naphtho[1,2-b]pyran;
(g) 3-(4-methoxyphenyl)-3-phenyl-13,13-dimethyl-13H-3H-indeno[2,'3,'3,4]naphtho[1,2-b]pyran;
(h) 3,3-di(4-methoxyethoxyphenyl)-11-morpholino-13,13-dimethyl-13H-3H-indeno[2,'3,'3,4]naphtho[1,2-b]pyran;
(i) 3,3-diphenyl-6,11-dimethoxy-13-acetoxy-13H-3H-indeno[2,'3,'3,4]naphtho[1,2-b]pyran;
(j) 3-(4-methoxyphenyl)-3-phenyl-6,10,11-trimethoxy-13-methyl-13-hydroxy-13H-3H-indeno[2,'3,'3,4]naphtho([1,2-b]pyran;
(k) 3-(4-methoxyphenyl)-3-phenyl1-6,10,11-trimethoxy-13-butyl-13-hydroxy-13H-3H-indeno[2,'3,'3,4]naphtho[1,2-b]pyran;
(l) 2,2-diphenyl-5-(2-hydroxy)propyl)-8-methoxy-2H-naphtho[1,2-b]pyran;
(m) 2,2-diphenyl-5-carbomethoxy-6-phenyl-9-methoxy-2H-naphtho[1,2-b]pyran;
(n) 3-(3,4-dimethoxyphenyl)-3-(4-methoxyphenyl)-11-morpholino-13,13-dimethyl-13H-3H-indeno[2,'3,'3,4]naphtho[1,2-b]pyran;
(o) 7-(4-morpholino-2-fluorophenyl)-7-(3,4-dimethoxyphenyl)-2-pentyl-4-oxo-4H-7H-[1,3]dioxino[5',4':3,4]naphtho[1,2b]pyran;
(p) 3-(4-methoxyphenyl)-3-(4-morpholinophenyl)-11-morpholino-13,13-dimethyl-13H-3H-indeno(2,'3',3,4)naphtho[1,2-b]pyran;
(q) 3,3-diphenyl-13,13-dimethyl-13H-3H-indeno[2,'3,'3,41naphtho[1,2-b]pyran;
(r) 3-(4-morpholinophenyl)-3-phenyl-6,11-dimethoxy-13-methoxy-13-methyl-13H-3H-indeno[2,'3,'3,4]naphtho[1,2-b]pyran;
(s) 2,2,7,7-tetraphenyl-4-oxo-2,3,4,7-tetrahydro-1H-pyrimidino[5',4':3,4]naphtho[1,2-b]pyran;

(t) 3,3di(4-dimethoxyphenyl)-6,7,10,11-tetramethoxy-13, 13-dimethyl-13H-3H-indeno[2,'3,'3,4]naphtho[1,2-b]pyran;
(u) 3-(4-methoxyphenyl)-3-phenyl-6,11-dimethoxy-13-ethyl-13-hydroxy-13H-3H-indeno[2,'3,'3,4]naphtho[1,2-b]pyran;
(v) 2,2diphenyl-5-(2-(2-hydroxyethoxy)ethoxy) carbonyl-6-(4-methoxyphenyl)-9-methoxy-2H-naphtho(1,2-b]pyran;
(w) 3-phenyl-3-(2-fluorophenyl)-3H-naphtho[2,1-b]pyran; or
(x) mixtures thereof.

7. The photochromic article of claim 1 further comprising at least one fixed tint dye.

8. The photochromic article of claim 1 wherein said photochromic article is adapted to exhibit a neutral activated color.

9. The photochromic article of claim 1 wherein photochromic material (c) is an organic photochromic material and is chosen from naphthopyrans, benzopyrans, phenanthropyrans, indenonaphthopyrans, oxazines, metal-dithiozonates, fulgides, fulgimides, spiro(indoline)pyrans or mixtures thereof.

10. The photochromic article of claim 1 further comprising an at least partial coating of an at least partially abrasion resistant coating applied to at least one surface of the substrate.

11. The photochromic article of claim 10 further comprising an at least partial coating of an at least partially antireflective coating applied to said abrasion resistant coating.

12. The photochromic article of claim 1 further comprising an at least partial coating of an at least partially cured polymeric coating applied to at least one surface of the substrate wherein said polymeric coating comprises photochromic material (b) and the substrate comprises photochromic material (c).

13. The photochromic article of claim 12 wherein the at least partially cured polymeric coating is a polymeric coating of thermoplastic or thermosetting materials.

14. The photochromic article of claim 13 wherein the at least partially cured polymeric coating is a polymeric coating of thermosetting materials chosen from polyurethanes, aminoplast, poly(meth)acrylates, polyanhydrides, polyacrylamides, epoxy resins or polysilanes.

15. The photochromic article of claim 12 further comprising an at least partial coating of primer interposed between the at least partially cured polymeric coating and the substrate.

16. The photochromic article of claim 15 further comprising an at least partial coating of an at least partially abrasion resistant coating applied to the surface of the at least partially cured polymeric coating.

17. The photochromic article of claim 16 further comprising an at least partial coating of an at least partially antireflective coating applied to the at least partial coating of an at least partially abrasion resistant coating applied to the surface of the at least partially cured polymeric coating.

18. The photochromic article of claim 1 wherein the substrate is chosen from paper, glass, ceramic, wood, masonry, textile, metal or organic polymeric material.

19. The photochromic article of claim 18 wherein the substrate is organic polymeric material and said organic polymeric material is chosen from poly(C1-C12 alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral or is polymerized from monomers chosen from bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bis methacrylate monomers, alkoxylated polyhydric alcohol polyacrylate monomers, styrene monomers, urethane acrylate monomers, glycidyl acrylate monomers, glycidyl methacrylate monomers, diallylidene pentaerythritol monomers or mixtures thereof.

20. The photochromic article of claim 19 wherein said organic polymeric material is an optical element.

21. The photochromic article of claim 20 wherein said optical element is an ophthalmic lens.

22. The photochromic article of claim 1 further comprising a superstrate connected to at least a portion of the substrate, said superstrate comprising at least one organic polymeric material.

23. The photochromic article of claim 22 wherein the superstrate comprises photochromic material (b) and the substrate comprises photochromic material (c).

24. The photochromic article of claim 23 wherein the superstrate is connected by being adherently bonded to at least a portion of the substrate.

25. The photochromic article of claim 23 wherein the superstrate is an organic polymeric material chosen from thermosetting or thermoplastic materials.

26. The photochromic article of claim 25 wherein the superstrate is a thermoplastic material and is polyurethane.

27. The photochromic article of claim 23 further comprising an at least partially abrasion resistant film superposed on at least a portion of the superstrate.

28. The photochromic article of claim 27 wherein the at least partially abrasion resistant film is an organic polymeric material chosen from thermoplastic and thermosetting materials.

29. The photochromic article of claim 28 wherein the at least partially abrasion resistant film is a thermoplastic material and is polycarbonate.

30. The photochromic article of claim 27 further comprising an at least partial coating of an at least partially antireflective coating applied to said abrasion resistant film superposed on said superstrate.

31. The photochromic article of claim 1 wherein photochromic material (b) is chosen from:
    (a) a single photochromic compound,
    (b) a mixture of photochromic compounds;
    (c) a material comprising at least one photochromic compound;
    (d) a material to which at least one photochromic compound is chemically bonded;
    (e) material (c) or (d) further comprising a coating to substantially prevent contact of the at least one photochromic compound with external materials;
    (f) a photochromic polymer; or
    (g) mixtures thereof.

32. The photochromic article of claim 9 wherein photochromic material (c) is chosen from:
    (a) a single photochromic compound;
    (b) a mixture of photochromic compounds;

(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

33. A photochromic article demonstrating consistent photochromic response over a broad temperature range comprising:
a) a substrate;
b) a temperature dependent reducing amount of at least one organic photochromic material associated with said substrate, said photochromic material having a temperature dependent variable absorbance that changes from more absorbing to less absorbing of radiation in its activating spectral absorbance as the temperature increases from 10° C. to 35° C.; and
c) at least one other photochromic material (c) associated with said substrate that is different from photochromic material (b); said photochromic material (b) being used in a coating or film on the surface of the substrate and interposed between photochromic material (c) and a source of activating radiation wherein the substituent groups of photochromic material (b) are chosen such that said photochromic article exhibits an unactivated state luminous transmittance of greater than 70 percent at 23° C. and a difference of 20 percent or less between the activated state luminous transmittance at saturation measured at 10° C. and the activated state luminous transmittance at saturation measured at 35° C., said photochromic article being activated by simulated sunlight from a xenon arc lamp set at 6.7 Watts/meter$^2$ UVA and 50,000 lumens/meter$^2$, said photochromic material (b) being chosen from:

(1) a naphthopyran compound represented by the following graphic formula I:

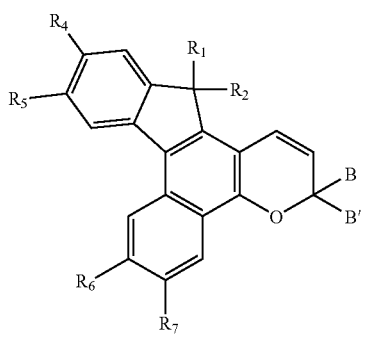

I wherein,
(a) $R^1$ and $R_2$ are each independently chosen from:
(i) hydrogen, hydroxy, $C_1$-$C_6$ alkyl, $C_1$-$C_8$ haloalkyl, $C_3$-$C_7$ cycloalkyl, or the group, —C(O)W, wherein W is hydroxy, $C_1$-$C_6$ alkyl, $C_1$-$C_6$ alkoxy, di($C_1$-$C_6$)alkylamino, morpholino or piperidino;
(ii) the group, —OR$^8$ wherein $R_8$ $C_1$-$C_6$ alkyl, $C_1$-$C_8$ haloalkyl, phenyl($C_1$-$C_3$)alkyl or the group —CH($R_9$)Q, wherein $R_9$ is hydrogen or $C_1$-$C_3$ alkyl and Q is —COOR$_{10}$, and $R_{10}$ is hydrogen or $C_1$-$C_3$ alkyl;
(iii) the group —CH($R_{12}$)G, wherein $R_{12}$ is hydrogen or $C_1$-$C_6$ alkyl, and G is —COOR$_{11}$, wherein $R_{11}$ is hydrogen or $C_1$-$C_6$ alkyl; or
(iv) the group T represented by the formula:

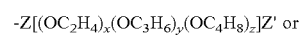

wherein -Z is —C(O)— or —CH$_2$—, Z' is $C_1$-$C_3$ alkoxy or a polymerizable group, x, y and z are each a number between 0 and 50, and the sum of x, y and z is between 2 and 50; or
(v) $R_1$ and $R_2$ together form $R_3$ chosen from a substituted or unsubstituted spiro-carbocyclic ring containing 5 to 6 carbon atoms, said spiro-carbocyclic ring being annellated with 0, 1 or 2 benzene rings, said substituents being hydrogen or $C_1$-$C_6$ alkyl;
(b) $R_4$ and $R_7$ are each independently chosen from hydrogen, provided that both are not hydrogen, the group T, —OR$_7'$ wherein $R_7'$ is chosen from $C_1$-$C_6$ alkyl, phenyl($C_1$-$C_6$)alkyl or $C_1$-$C_6$ alkoxy($C_1$-$C_6$)alkyl or $R_4$ and $R_7$ are each independently a nitrogen-containing group chosen from:
(i) —N($R_{15}$)$R_{16}$ wherein $R_{15}$ and $R_{16}$ are each independently chosen from hydrogen, $C_1$-$C_8$ alkyl or $R_{15}$ and $R_{16}$ come together with the nitrogen atom to form a $C_3$-$C_{20}$ hetero-bicycloalkyl ring or a $C_4$-$C_{20}$ hetero-tricycloalkyl ring;
(ii) a nitrogen containing ring represented by the following graphic formula:

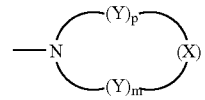

wherein each Y is —CH$_2$—, and X is chosen from —Y—, —O—, —S—, —S(O)—, —S(O$_2$)—, —NH—, —N($R_{17}$)— or —N(aryl)-, wherein $R_{17}$ is $C_1$-$C_6$ alkyl, said aryl is phenyl or naphthyl, m is the integer 1, 2 or 3, and p is the integer 0, 1, 2, or 3 and when p is O, X is Y; or
(iii) a group represented by one of the following graphic formulae:

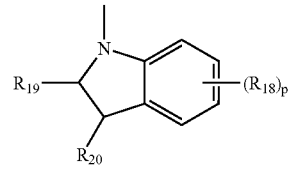

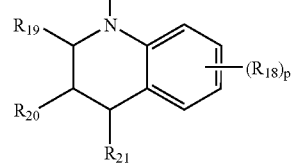

wherein $R_{19}$, $R_{20}$ and $R_{21}$ are each independently chosen for each occurrence in each formula from hydrogen or $C_1$-$C_6$ alkyl, or the groups $R_{19}$ and $R_{20}$ together form a ring of 5 to 8 carbon atoms and each $R_{18}$ is $C_1$-$C_6$ alkyl and p being the integer 0, 1, 2 or 3;

(c) $R_5$ and $R_6$ are each independently chosen from hydrogen, $C_1$-$C_6$ alkyl, $C_1$-$C_6$ haloalkyl, the group T, —$OR_7$, described hereinbefore in (b) or nitrogen-containing group (b) (i), (ii) or (iii); and (d) B and B' are each independently chosen from:
  (i) mono-T-substituted phenyl;
  (ii) the unsubstituted, mono-, di-, or tri-substituted aryl groups, phenyl or naphthyl, each of said aryl substituents being chosen from hydroxy, aryl, $C_1$-$C_8$ alkoxy ($C_1$-$C_8$)alkoxy, aryl($C_1$-$C_6$)alkyl, aryloxy, $C_1$-$C_6$ alkyl, $C_1$-$C_6$ haloalkyl, $C_1$-$C_6$ alkoxy, acryloxy, methacryloxy, halogen, —$CF_3$, —CN or —$COOR_{11}$; wherein $R_{11}$ is the same as described hereinbefore; or
  (iii) mono-substituted phenyl, said substituent located at the para position being —$(CH_2)_t$— or —O—$(CH_2)_t$—, wherein t is the integer 1, 2, 3, 4, 5 or 6, said substituent being connected to an aryl group on another photochromic material;

(2) a naphthopyran compound represented by the following graphic formula II:

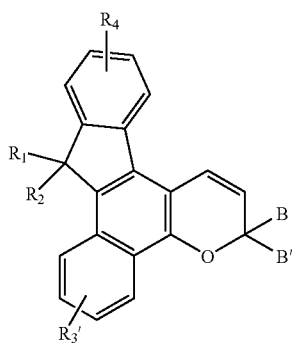

II wherein
  $R_1$, $R_2$, $R_4$, B and B' are the same groups described hereinbefore in (1) (a), (b) and (d); $R_{3'}$ is —$OR_{8'}$, wherein $R_{8'}$ is $C_1$-$C_6$ alkyl or phenyl($C_1$-$C_3$)alkyl, or $R_{3'}$ is chosen from hydrogen, $C_1$-$C_6$ alkyl or $C_1$-$C_6$ haloalkyl;

(3) a naphthopyran compound represented by graphic formula III:

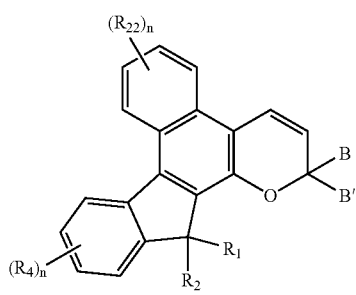

III wherein;
  $R_1$, $R_2$, $R_4$, B and B' are the same groups described hereinbefore in (1) (a), (b) and (d); each $R_{22}$ is independently chosen from hydrogen, $C_1$-$C_6$ alkyl, $C_3$-$C_7$ cycloalkyl, $C_1$-$C_6$ haloalkyl or —$OR_{8'}$, which was described hereinbefore in (2), and n is the integer 0, 1, 2, or 3;

(4) a naphthopyran compound represented by the following graphic formula IV:

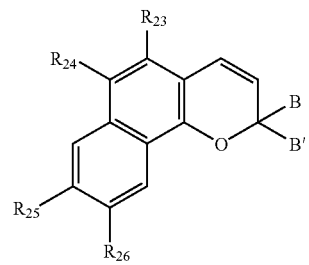

IV wherein,
  (a) $R_{23}$ is —C(O)L, or —$C(R_{27})(R_{28})OR_{11}$, wherein L is —$OR_{11}$, —$N(R_{15})R_{16}$ or an unsubstituted, mono-substituted or di-substituted heterocyclic ring chosen from 1-indolinyl, morpholino, piperidino, 1-pyrrolidyl or 1-piperazinyl, said heterocyclic ring substituents being $C_1$-$C_6$ alkyl; $R_{11}$, $R_{15}$, and $R_{16}$ are the same as described hereinbefore in (1) (a) (iii) and (b) (i); $R_{27}$ and $R_{28}$ are each independently chosen from $C_1$-$C_6$ alkyl, $C_3$-$C_7$ cycloalkyl, $C_1$-$C_6$ haloalkyl or phenyl;
  (b) $R_{24}$ is hydrogen, $C_1$-$C_6$ alkyl, $C_3$-$C_7$ cycloalkyl, mono- or di-($C_1$-$C_6$)alkylaryl, mono- or di-($C_1$-$C_6$) alkoxyaryl, $C_1$-$C_6$ haloalkyl, phenyl or naphthyl;
  (c) $R_{25}$ and $R_{26}$ are each independently chosen from hydrogen, $C_1$-$C_6$ alkyl, $C_3$-$C_7$ cycloalkyl, $C_1$-$C_6$ haloalkyl, the group T, described hereinbefore in (1) (a) (iv) —$OR_{8'}$, described hereinbefore in (2) or said nitrogen-containing group (1) (b) (i), (ii), or (iii) described hereinbefore or $R_{25}$ and $R_{26}$ together form one of the following graphic formulae:

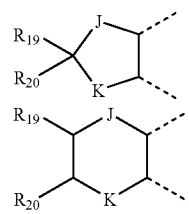

wherein J and K are each independently chosen for each occurrence in each formula from oxygen or the group —$N(R_{15})$—, $R_{15}$, $R_{19}$ and $R_{20}$, are the same groups described hereinbefore in (1) (b) (i) and (iii); and
  (d) B and B' are the same groups described hereinbefore in (1) (d);

(5) a naphthopyran represented by the following graphic formula V:

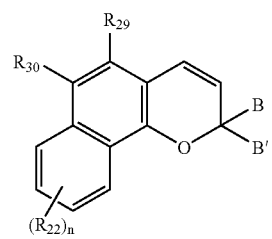

V wherein;
(a) $R_{22}$ and n are the same as described hereinbefore in (3); $R_{29}$ is hydroxy, $C_1$-$C_6$ alkyl, $C_3$-$C_7$ cycloalkyl, $C_1$-$C_6$ haloalkyl, aryl, mono($C_1$-$C_6$)alkoxyaryl, di($C_1$-$C_6$)alkoxyaryl, mono($C_1$-$C_6$)alkylaryl, di($C_1$-$C_6$)alkylaryl, haloaryl, di($C_1$-$C_6$)alkylaminoaryl, the group T described hereinbefore in (1) (a) (iv), —$OR_8$, described hereinbefore in (2), or said nitrogen-containing group (1) (b) (i), (ii) or (iii) described hereinbefore;
(b) $R_{30}$ is hydrogen or $R_{23}$ described hereinbefore in (4) (a); and
(c) B and B' are the same groups described hereinbefore in (1) (d);
(6) a naphthopyran compound represented by the following graphic formula VI:

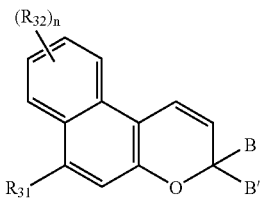

VI wherein;
(a) $R_{31}$ is hydrogen or $R_{29}$ described hereinbefore in (5) (a)
(b) $R_{32}$ is $C_1$-$C_6$ alkyl, $C_1$-$C_6$ alkoxy or $C_1$-$C_6$ haloalkyl, n is the same as described hereinbefore in (3); and
(c) B and B' are the same groups described hereinbefore in (1) (d); and
(7) a naphthopyran represented by the following graphic formula VII:

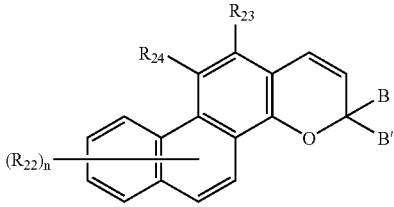

VII wherein:
each $R_{22}$ and n are the same as described hereinbefore in (3); $R_{23}$ and $R_{24}$ are the same as described hereinbefore in (4) (a) and (b); B and B' are the same as described hereinbefore in (1) (d);
(8) a naphthopyran represented by the following graphic formula VIII:

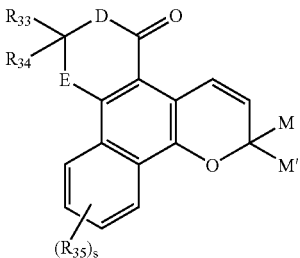

VIII wherein,
(a) $R_{33}$ and $R_{34}$ together form an oxo group or $R_{33}$ is hydrogen and $R_{34}$ is hydrogen, $C_1$-$C_6$ alkyl, $C_3$-$C_7$ cycloalkyl, allyl, phenyl, mono- or di-substituted phenyl, benzyl, mono-substituted benzyl, linear or branched $C_3$-$C_{12}$ alkenyl, $C_1$-$C_6$ alkoxy carbonyl($C_1$-$C_6$)alkyl, methacryloxy($C_1$-$C_6$)alkyl, acryloxy($C_1$-$C_6$)alkyl, $C_1$-$C_4$ acryloxy($C_1$-$C_6$)alkyl, each of said phenyl or benzyl substituents being $C_1$-$C_6$ alkyl, $C_1$-$C_6$ alkoxy, morpholino, di($C_1$-$C_6$)alkylamino, chloro or fluoro;
(b) each $R_{35}$ is independently chosen for each occurrence from $C_1$-$C_6$ alkyl, $C_1$-$C_6$ alkoxy, chloro, fluoro, phenyl, $C_3$-$C_7$ cycloalkyl, di($C_1$-$C_6$) alkylamino, morpholino, thiomorpholino, piperidino, pyridyl, N—($C_1$-$C_6$)alkyl piperizino or N-phenyl piperizino, and s is the integer 0, 1 or 2;
(c) D is oxygen or —N($R_{36}$)—, wherein $R_{36}$ is hydrogen, $C_1$-$C_6$ alkyl, $C_3$-$C_7$ cycloalkyl, $C_1$-$C_5$ acyl or phenyl;
(d) E is oxygen, —N($R_{36}$)— or —C($R_{37}$) ($R_{38}$)—, wherein $R_{37}$ and $R_{38}$ are each independently chosen from hydrogen, $C_1$-$C_6$ alkyl or $C_3$-$C_7$ cycloalkyl, with the proviso that when E is —C($R_{37}$) ($R_{38}$)—, D is oxygen; and
(e) M and M' are each chosen from the unsubstituted, mono, di or tri-substituted aryl group, phenyl or naphthyl; each of said aryl substituents being chosen from hydroxy, phenyl, naphthylaryl($C_1$-$C_6$)alkyl, aryloxy, $C_1$-$C_6$ alkyl, $C_1$-$C_6$ chloroalkyl, $C_1$-$C_6$ fluoroalkyl, $C_1$-$C_6$ alkoxy, acryloxy, methacryloxy, bromo, chloro or fluoro; or
(9) mixtures thereof.

34. The photochromic article of claim 33 wherein the photochromic article is adapted to exhibit an unactivated state luminous transmittance of greater than 80 percent at 23° C., and a difference of 10 percent or less between the activated state luminous transmittance at saturation measured at 10° C. and the activated state luminous transmittance at saturation measured at 35° C.

35. The photochromic article of claim 33 further comprising at least one fixed tint dye.

36. The photochromic article of claim 33 wherein said photochromic article is adapted to exhibit a neutral activated color.

37. The photochromic article of claim 33 further comprising an at least partial coating of an at least partially abrasion resistant coating.

38. The photochromic article of claim 37 further comprising an at least partial coating of an at least partially antireflective coating.

39. The photochromic article of claim 33 further comprising an at least partial coating of an at least partially cured polymeric coating applied to at least one surface of the substrate wherein said polymeric coating comprises photochromic material (b) and the substrate comprises photochromic material (c).

40. The photochromic article of claim 39 wherein the at least partially cured polymeric coating is a polymeric coating of thermoplastic or thermosetting materials.

41. The photochromic article of claim 40 wherein the at least partially cured polymeric coating is a polymeric coating of thermosetting materials chosen from polyurethanes, aminoplast resins, poly(meth)acrylates, polyanhydrides, polyacrylamides, epoxy resins or polysilanes.

42. The photochromic article of claim 39 further comprising an at least partial coating of primer interposed between the at least partially cured polymeric coating and the substrate.

43. The photochromic article of claim 42 further comprising an at least partial coating of an at least partially abrasion resistant coating applied to the surface of the at least partially cured polymeric coating.

44. The photochromic article of claim 43 further comprising an at least partial coating of an at least partially antireflective coating.

45. The photochromic article of claim 33 wherein the substrate is paper, glass, ceramic, wood, masonry, textile, metal or organic polymeric material.

46. The photochromic article of claim 45 wherein the substrate is organic polymeric material and said organic polymeric material is chosen from poly(C1-C12 alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral or is polymerized from monomers chosen from bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bis methacrylate monomers, alkoxylated polyhydric alcohol polyacrylate monomers, styrene monomers, urethane acrylate monomers, glycidyl acrylate monomers, glycidyl methacrylate monomers, diallylidene pentaerythritol monomers or mixtures thereof.

47. The photochromic article of claim 46 wherein said organic polymeric material is an optical element.

48. The photochromic article of claim 47 wherein said optical element is an ophthalmic lens.

49. The photochromic article of claim 47 wherein said optical element is an ocular device.

50. The photochromic article of claim 33 further comprising a superstrate connected to at least a portion of the substrate, said superstrate comprising at least one organic polymeric material wherein the superstrate comprises photochromic material (b) and the substrate comprises photochromic material (c).

51. The photochromic article of claim 50 wherein the superstrate is an organic polymeric material chosen from thermosetting or thermoplastic materials.

52. The photochromic article of claim 51 wherein the superstrate is a thermoplastic material and is polyurethane.

53. The photochromic article of claim 50 further comprising an at least partially abrasion resistant film superposed on at least a portion of the superstrate.

54. The photochromic article of claim 53 wherein the at least partially abrasion resistant film is an organic polymeric material chosen from thermoplastic and thermosetting materials.

55. The photochromic article of claim 54 wherein the at least partially abrasion resistant film is a thermoplastic material and is polycarbonate.

56. The photochromic article of claim 54 further comprising an at least partial coating of an at least partially antireflective coating.

* * * * *

UNITED STATES PATENT AND TRADEMARK OFFICE
Certificate

Patent No. 7,320,826 B2

Patented: January 22, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Anil Kumar, Allegheny County, PA (US); Barry Van Gemert, Westmoreland County, PA (US); Forrest R. Blackburn, Allegheny County, PA (US); Clara E. Nelson, Allegheny County, PA (US); Olga G. Goncharova, Acton, MA (US); and Anu Chopra, Pittsburgh, PA (US).

Signed and Sealed this Thirtieth day of November 2010.

CALLIE SHOSHO
*Supervisory Patent Examiner*
Art Unit 1787
Technology Center 1700